(12) United States Patent
Mensah

(10) Patent No.: US 10,563,272 B2
(45) Date of Patent: Feb. 18, 2020

(54) **COMPOSITIONS COMPRISING *METARHIZIUM* FUNGI AND USE THEREOF AS A PESTICIDE**

(71) Applicants: Cotton Research and Development Corporation, New South Wales (AU); The Crown in right of the State of New South Wales acting through the Department of Primary Industries, as office of the NSW Department of Industry, Skills and Regional Development, New South Wales (AU)

(72) Inventor: Robert Mensah, New South Wales (AU)

(73) Assignees: Cotton Research and Development Corporation, New South Wales (AU); The Crown in right of the State of New South Wales acting through the Department of Primary Industries, as office of the NSW Department of Industry, Skills and Regional Development, New South Wales (AU)

( * ) Notice: Subject to any disclaimer, the term of this patent is extended or adjusted under 35 U.S.C. 154(b) by 0 days.

(21) Appl. No.: 15/763,264

(22) PCT Filed: Sep. 23, 2016

(86) PCT No.: PCT/AU2016/050890
§ 371 (c)(1),
(2) Date: Mar. 26, 2018

(87) PCT Pub. No.: WO2017/049355
PCT Pub. Date: Mar. 30, 2017

(65) Prior Publication Data
US 2018/0274046 A1    Sep. 27, 2018

(30) Foreign Application Priority Data

Sep. 25, 2015 (AU) .................. 2015903924

(51) Int. Cl.
*C12R 1/645* (2006.01)
*A01N 63/04* (2006.01)

(52) U.S. Cl.
CPC .............. *C12R 1/645* (2013.01); *A01N 63/04* (2013.01)

(58) Field of Classification Search
CPC .................. C12R 1/645; A01N 63/04
See application file for complete search history.

(56) References Cited

U.S. PATENT DOCUMENTS

| 2010/0112060 A1 | 5/2010 | Maor et al. |
| 2013/0156740 A1 | 6/2013 | Leland |

FOREIGN PATENT DOCUMENTS

| KR | 1020150057124 A | 5/2015 |
| WO | 0228189 A2 | 4/2002 |
| WO | 2014079719 A1 | 5/2014 |

OTHER PUBLICATIONS

Meyling et al., Biological Control 43:145-155, 2007.*
Fang et al., Plant Physiology 154:1549-1557, Sep. 13, 2010.*
Surulivelu T. et al. "Evaluation of fungal pathogens for the management of mealybugs in Bt cotton" 2012, Journal of Biological Control, 26: 92-96.

* cited by examiner

*Primary Examiner* — Delia M Ramirez
(74) *Attorney, Agent, or Firm* — Riverside Law LLP

(57) ABSTRACT

The present disclosure relates generally to an entomopathogenic fungi, *Metarhiziuim* spp, and its use to control invertebrate pests of agricultural crops, in particular, invertebrate pests which affect cotton crops.

15 Claims, 31 Drawing Sheets

Figure 1:

Specification includes a Sequence Listing.

COMPOSITIONS COMPRISING *METARHIZIUM* FUNGI AND USE THEREOF AS A PESTICIDE

CROSS-REFERENCE TO RELATED APPLICATIONS

This application is the U.S. national phase application filed under 35 U.S.C. § 371 claiming benefit to International Patent Application No. PCT/AU16/50890, filed on Sep. 23, 2016, which claims priority to Australian Patent Application Ser. No. 2015903924, filed Sep. 25, 2015, the entire contents of all of which are incorporated herein by reference in their entireties.

FIELD

The present disclosure relates to the use of *Metarhiziuim* spp. as a fungal pesticide e.g., an insecticide, to control invertebrate pests, in particular, invertebrate pests which affect cotton crops.

BACKGROUND

Agriculture is an important industry with considerable research and investment into improving processes and efficiencies. One important area of research is into ways of controlling pests which may cause significant damage to crops. Crops can be attacked by a wide range of pests and various strategies have been employed to control, kill or deter them.

One such approach involves synthetic insecticides which have been used over the last 50 years to control insect pests. Heavy use of these insecticides can exert a strong selection pressure on individual insects with mutations and this has led to increasing insect resistance to the insecticides.

An alternative approach was developed by incorporating the use of insecticidal proteins, for example *Bacillus thuringiensis* (Bt), in both sprays and genetically engineered crops e.g., Bt cotton. Transgenic crops, especially cotton, are now grown in many countries to control insect pests and their introduction has reduced synthetic insecticide use against some pests to a high degree. For example, in the Australian cotton industry, transgenic cotton crops (Bollgard II®) are planted in 95% of the area to manage *Helicoverpa* spp. By contrast, only 5% is planted to conventional cotton crops.

The introduction and adoption of transgenic cotton crops has reduced the importance of *Helicoverpa* spp. as major cotton pests in Australia. Furthermore, the sustained control of *Helicoverpa* spp. by various transgenic cotton crops has also significantly reduced the need to use synthetic insecticide against these pests. However, since the synthetic insecticides previously used to control *Helicoverpa* spp. also inadvertently suppressed sucking pest populations, the reduced reliance on insecticides for control of *Helicoverpa* spp. i.e., as a result of widespread adoption of transgenic cotton crops, has increased the threat posed by sucking pests such as, for example, green mirids (*Creontiades dilutus*), aphids (*Aphis gossypii*), green vegetable bug (*Nezara viridula*) and silverleaf whitefly (*Bemisia tabaci*). As such, the transition from conventional to transgenic cotton has led to an increase in the presence of pests that are unaffected by the toxin in the transgenic plants, which in turn has led to increased use of synthetic insecticides to control them.

Currently, cotton growers still face the problem of *Helicoverpa* spp. resistance, and the emergence of silverleaf whiteflies, green mirids, green vegetable bugs, aphids, two-spotted mites, and mealybugs etc. as more prevalent pests has resulted in yield loss. Soil pests such as wireworms are still an issue in most growing areas. Pupae busting is also a major issue for growers in order to comply with the Bollgard II® resistance management plan. The use of cheaper broad spectrum insecticides such as pyrethroids has increased partly due to the endosulfan ban and the high cost of cotton production. This increase in use of broad spectrum insecticides can cause disruption of beneficial insect populations and be counter-productive to integrated pest management (IPM) efforts, offsetting the benefits of IPM typically enabled by transgenic cotton lines. Thus, there is a continued need to develop new approaches as part of an IPM strategy to control agricultural pests, such as those affecting cotton crops.

SUMMARY

The present inventors performed field trials to determine the effect of application of different isolates of entomopathogenic fungi on the development, survival and control of invertebrate pests affecting agricultural crops. In doing so, the inventors have shown that an isolate of *Metarhizium* designated DAT 511 (deposited under Accession No. V15/001452) can be used as an entomopathogenic agent to control invertebrate pests, particularly those insect pests affecting cotton crops.

For example, the inventors identified that the application of entomopathogenic fungus DAT511 to cotton plants and the surrounding soil (i) prevented a significant proportion of cotton bollworm, *Helicoverpa armigera*, larvae in the soil from developing into pupae, and (ii) for those larvae that did develop into pupae, prevented the emergence of moths. Overall, the inventors observed greater than 80% mortality of *Helicoverpa armigera* in plants treated with fungus DAT 511, demonstrating the utility of this entomopathogenic fungus as a spray on cotton to prevent the development and survival of *Helicoverpa armigera* larvae and pupae in the soil.

The inventors have also shown that the entomopathogenic fungus DAT511 can be used as an entomopathogenic agent to control a range of other invertebrate pests affecting agricultural crops, whilst not significantly affecting populations of beneficial insects. For example, the inventors have shown that DAT511 is particularly efficacious in controlling populations of wireworm, cutworms, aphids, thrips, green vegetable bugs, mirids, apple dimpling bugs, silverleaf whiteflies and cotton bollworm, whilst not effecting beneficial insects, such as predatory beetles, predatory bugs, predatory lacewings and spiders. As such, the inventors have demonstrated the broad utility of DAT511 as an entomopathogenic agent for control of insect pests in agriculturally important crops, in particular, cotton.

Accordingly, the present disclosure provides an isolated strain of *Metarhizium* spp. or a spore thereof, wherein the strain of *Metarhizium* spp. comprises a nucleotide sequence having at least 95% identity to the sequence set forth in SEQ ID NO: 1. In one example, the isolated strain of *Metarhizium* spp. or a spore thereof comprises the nucleotide sequence set forth in SEQ ID NO: 1. Preferably, the isolated strain or spore of *Metarhizium* spp. is as deposited with the National Measurement Institute under accession number V15/001452.

The present disclosure also provides a composition comprising a strain of *Metarhizium* spp. or a spore thereof of the disclosure. In one example, the composition comprises the strain of *Metarhizium* spp. or a spore thereof and at least one diluent, carrier and/or excipient.

In one example, the composition may comprise the strain of *Metarhizium* spp. or the spore thereof in oil. For example, the spores of the strain of *Metarhizium* spp. may be provided in the form of a dry powder suspended in an oil.

In another example, the composition may comprise spores of the strain of *Metarhizium* spp. suspended in an oil-in-water emulsion.

The oil for use in accordance with the composition of the disclosure may be any suitable oil known in the art for such a purpose. Examples include, but are not limited to, petroleum based oil, DC Tron oil ($nC_{21}$ and $nC_{24}$ oils), Canopy oil ($nC_{27}$ oil), Biopest oil ($nC_{24}$ oils), dormant oil, a horticultural oil, a low molecular weight oil, olive oil, soy oil, corn oil, sunflower oil, canola oil, linseed oil, castor oil, fish oil, tung oil, sesame oil and/or MCT oils.

In one example, the composition comprises spores at a concentration of at least 10 spores/mL. For example, the composition may comprise spores at a concentration of at least $10^2$ spores/mL, or at a concentration of at least $10^3$ spores/mL, or at a concentration of at least $10^4$ spores/mL, or at a concentration of at least $10^5$ spores/mL, or at a concentration of at least $10^6$ spores/mL, or at a concentration of at least $10^7$ spores/mL. Preferably, the composition comprises spores at a concentration of $1\times10^7$ spores/mL or more.

The composition may further comprise one or more additives selected from emulsifiers, wetting agents, surfactants, stabilizers and/or spreaders. Such additional additives are known in the art.

The composition may also further comprise one or more additional substances having insecticidal or pesticidal activity. For example, the composition may comprise one or more additional substances having insecticidal or pesticidal activity selected from the group consisting of abamectin, acetamiprid, alpha-cypermethrin, amitraz, amorphous silica, *Bacillus thuringiensis*, bifennthrin, chloropyrifos, chlorantraniliprole, chlorantraniliprole/thiamethoxam, clothianidin, cyantraniliprole, cypermethrin, deltamethrin, diafenthiuron, mimethoate, emamectin benzoate, esfenvalerate, fipronil, gamma-cyhalothrin, imidacloprid, indoxocarb, lambda-cyhalothrin, helicoverpa NPV, magnet, methoyl, omethoate, paraffinic oil, phorate, piperonyl butoxide, pirimicarb, pymetrozine, pyriproxyfen, spirotetramat, sulfoxaflor and thiodicarb. Further substances having insecticidal or pesticidal activity which are suitable for inclusion in the composition disclosed herein are known in the art.

The present disclosure also provides a method of controlling one or more invertebrate pests by contacting the invertebrate pest with a strain of *Metarhizium* spp. and/or a spore thereof of the disclosure. Preferably, the strain or spore of *Metarhizium* spp. comprises a nucleotide sequence having at least 95% identity to the sequence set forth in SEQ ID NO: 1. For example, the strain or spore of *Metarhizium* spp. comprises the nucleotide sequence set forth in SEQ ID NO: 1. More preferably, the strain or spore of *Metarhizium* spp. is as deposited with the National Measurement Institute under accession number V15/001452.

The present disclosure also provides a method of protecting a plant, plant propagation material and/or animal from one or more invertebrate pests by contacting the plant, plant propagation material, soil or other growth medium surrounding roots of the plant, the animal and/or the habitat or breeding ground of the invertebrate pest, with a fungus, spore or composition of the present disclosure. Preferably, the invertebrate pest(s) is(are) exposed to, or brought in contact with, the fungus, spore or composition. Preferably, the strain or spore of *Metarhizium* spp. comprises a nucleotide sequence having at least 95% identity to the sequence set forth in SEQ ID NO: 1. More preferably, the strain or spore of *Metarhizium* spp. comprises the nucleotide sequence set forth in SEQ ID NO: 1. Even more preferably, the strain or spore of *Metarhizium* spp. is as deposited with the National Measurement Institute under accession number V15/001452.

In one example, the strain of *Metarhizium* spp. is provided in the form of reproductively-viable spores e.g., in the form of a dry powder.

In one example, at least one of the one or more invertebrate pests is a plant pest. In such an example, the method comprises applying the strain of *Metarhizium* spp. or the spore thereof to the plant and/or its surrounding and/or a propagation material of the plant and/or a breeding ground or habitat of the pest. For example, the method comprises applying the strain of *Metarhizium* spp. or the spore thereof directly to the plant. Alternatively, or in addition, the method may comprise applying the strain of *Metarhizium* spp. or the spore thereof to a propagation material of the plant e.g., a seed. Alternatively, or in addition, the method may comprise applying the strain of *Metarhizium* spp. or the spore thereof to an area near or surrounding a plant e.g., soil or irrigation ditch/channel. Alternatively, or in addition, the method may comprise applying the strain of *Metarhizium* spp. or the spore thereof to a breeding ground or habitat of the pest.

In one example, the plant pest may be an insect or arachnid e.g., such as belonging to an order selected from Lepidoptera, Coleoptera, Hemiptera, Thysanoptera, Trombidiformes, Orthoptera and Diptera. In one example, the plant pest is an insect e.g., such as belonging to an order selected from Lepidoptera, Coleoptera, Hemiptera, Thysanoptera, Orthoptera and Diptera. In one example, the plant pest is an arachnid e.g., such as belonging to the order Trombidiformes.

In one example, at least one of the one or more invertebrate pests is selected from the group consisting of *Helicoverpa armigera, Helicoverpa punctigera, Helicoverpa zea, Heliothis virescens*, diamondback moth (*Plutella xylostella*), *Pectinophora scutigera* (pink spotted bollworm), *Earias huergeliana* (rough bollworm), *Anthonomus grandis* (boll weevil), colorado potato beetle, fall armyworm, southern armyworm, beet armyworm, loopers including cabbage looper, soybean looper, saltmarsh caterpillar, European corn borer, cotton leaf perforator, omnivorous leafroller, citrus peelminer, cotton stainer, cluster caterpillar, cutworms, red shouldered leaf beetle, *Creontiades dilutus* (green mirids), *Nezara viridula* (green vegetable bug), nematodes including cereal cyst nematode (*Heterodera avenae*), root-knot nematode (*Meloidogyne* spp.), root-lesion nematode (*Pratylenchus* spp.), citrus nematode (*Tylenchulus* spp.), dagger nematode (*Xiphinema* spp.), stem nematode (*Ditylenchus dispaci*) and *Anguina agrostis, Agrypnus variabilis* (true wire worm), *Pterohelaeus darlingensis* (Eastern false wire worm), *Gonocephalum macleayi* (southern false wireworm), Saragus spp. (false wireworms), *Agrotis* spp. (cutworms), *Smynthurodes betae* (bean root aphids), *Spodoptera exigua* (lesser armyworm), *Epiphyas postvittana* (light brown apple moth), *Thrips tabaci* (tobacco thrip), *Frankliniella schultzi* (tomato thrip), *Frankliniella occidentalis* (western flower thrip), *Chaetocnema* spp. (brown flea beetle), *Nisotra* spp. (redheaded fleabeetle), *Austroasca viridigrisea* (vegetable leafhopper), *Amrasca terraereginae* (cotton leafhopper), *Taylorilygus pallidulus* (brokenbacked bug), *Campylomma liebknechti* (apple dimpling bug), *Crocidosema plebejana* (cotton tipworm), *Bucculatrix gossypii* (cotton leafperforator), *Aphis gossypii* (cotton aphid), *Anomis flava* (cotton looper), *Tetranychus ludeni* (bean spider mite), *Tetranychus lambi* (straweberry spider mite), *Myzus persicae* (green peach aphid), *Trialeurodes vaporariorum* (greenhouse whitefly), *Bemisia tabaci* (silverleaf whitefly) including B type and Q types, *Dysdercus sidae* (cotton stainer), *Tectocoris diophthalmus* (cotton harlequin bug), *Oxycarenus luctuosus* (cotton seed bug), *Spodoptera littura* (cluster caterpillar), *Heliothis zea*, rice stem borer, brown plant hopper, two spotted mites, larval wood moth, a red coffee borer, a larval bag worm or case moth, a caterpillar of *Cryptothelia* or *Pteroma*, a cutworm, an army worm, a Pieridae butterfly, the family Lymantriidae, *Lymantria ninayi, L. rosa, L. novaguinensis, Calliteara queenslandica, Dasychira wandammena*, a looper caterpillar, a Millionaire Moth, from the genus *Milionia* spp, *Alcis papuensis, Paradromulia nigrocellata, Terminalias, Kamarere, Hyposidera talcata, Anthela ekeikei*, from the genus *Anthelidae*, from the genus *Syntherata* spp, a Thyrididae, a Limacodidae, a Pyralidae moth *Hypsipyla robusta*, a Hyblaeidae, a diamondback moth (*Plutella xylostella*), fall armyworm, a southern armyworm, a beet armyworm, saltmarsh caterpillar, scales, psyllids, cicadas, treehoppers, planthoppers, *Aphis gossypii* (Cotton aphid), *Austroaqsca viridigrisea* (vegetable leaf hopper), *Amrasca terraereginae* (cotton leaf hopper), *Bemisia tabaci* (silver leaf white flies), *Trialeurodes vaporariorum* (Greenhouse white flies), tarnished and western tarnished plant bug, *Helopeltis* spp., honeylocust plant bug, *Tetranychus urticae* (two-spotted mites), spider mite and their relatives (Tetranychoidea), earth mites (Penthaleidae), thread-footed mites (Tarsonemidae), gall mites, rust mites (Eriophyidae), *Pectinophora gossypiella* (Pink bollworm), *Creontiades pacificus* (Brown mirid), *Dictyotus caenosus* (Brown shield bug), *Halticinae* (Flea beetle), *Plautia affinis* (green stink bug), *Piezodorus hybneri* (Red banded shield bug), *Gonocepphalun macleayi* (False wireworm), *Austroasca viridigrisea* (Green jassid), *Amrasca terraereginae* (brown jassids), *Phenacoccus solenopsis* (*Solenopsis* mealybugs), *Nomadacris guttulosa* (Spur-throated locust) and *Bactrocera tryoni* (Queensland Fruit fly).

In one example, at least one of the one or more invertebrate pests is selected from the group consisting of *Helicoverpa* spp. (e.g., *Helicoverpa armigera* and/or *Helicoverpa punctigera*), mirids (e.g., green mirid and/or brown mirid), wireworm (e.g., true wireworm and/or false wireworm), cutworms, apple dimpling bugs, aphids, green vegetable bug, boll weevil, Rutherglen bug, nematodes, thrips (e.g., Tobacco thrip, Tomato thrip and/or western flower thrip), mites (e.g., two-spotted mite), silverleaf whitefly, bollworm (e.g., pink bollworm, pink spotted bollworm and/or rough bollworm), armyworm (e.g., lesser armyworm), light brown apple moth, cluster caterpillar, cotton looper, cotton tipworm, cotton leaf perforator, broken backed bug, shield bugs (e.g., brown shield bug and/or red banded shield bug), cotton seed bug, flea beetle, stink bugs, jassids (e.g., green jassid and/or brown jassid), mealybugs, locust (e.g., spur-throated locust), fruit fly (e.g., Queensland fruit fly), and pale cotton stainer.

In one example, at least one of the one or more invertebrate pests is selected from *Helicoverpa* spp. (e.g., *Helicoverpa armigera* and/or *Helicoverpa punctigera*), mirids (e.g., green mirid and/or brown mirid), wireworm, cutworms, apple dimpling bugs, aphids, green vegetable bug, boll weevil, Rutherglen bug, nematodes, thrips (e.g., Tobacco thrip, Tomato thrip and/or western flower thrip), mites (e.g., two-spotted mite) and/or silverleaf whitefly.

In one example, the one or more invertebrate pests comprises a *Helicoverpa* spp. e.g., *Helicoverpa armigera* or *Helicoverpa punctigera*. In one example, the one or more invertebrate pests comprises a mirid e.g., a green mirid or a brown mirid. In one example, the one or more invertebrate pests comprises a wireworm e.g., a true wireworm or a false wireworm. In one example, the one or more invertebrate pests comprises a cutworm. In one example, the one or more invertebrate pests comprises an apple dimpling bug. In one example, the one or more invertebrate pests comprises an aphid. In one example, the one or more invertebrate pests comprises a green vegetable bug. In one example, the one or more invertebrate pests comprises a boll weevil. In one example, the one or more invertebrate pests comprises a Rutherglen bug. In one example, the one or more invertebrate pests comprises a nematode. In one example, the one or more invertebrate pests comprises a thrip e.g., a tobacco thrip, a tomato thrip or a western flower thrip. In one example, the one or more invertebrate pests comprises a mite e.g., a two-spotted mite. In one example, the one or more invertebrate pests comprises a silverleaf whitefly. In one example, the one or more invertebrate pests comprises a bollworm e.g., a pink bollworm, a pink spotted bollworm or a rough bollworm. In one example, the one or more invertebrate pests comprises a armyworm e.g., a lesser armyworm. In one example, the one or more invertebrate pests comprises a light brown apple moth. In one example, the one or more invertebrate pests comprises a cluster caterpillar. In one example, the one or more invertebrates pest comprises a cotton looper. In one example, the one or more invertebrate pests comprises a cotton tipworm. In one example, the one or more invertebrate pest comprises a cotton leaf perforator. In one example, the one or more invertebrate pests comprises a broken backed bug. In one example, the one or more invertebrate pests comprises a shield bug e.g., a brown shield bug or a red banded shield bug. In one example, the one or more invertebrate pests comprises a cotton seed bug. In one example, the one or more invertebrate pests comprises a flea beetle. In one example, the one or more invertebrate pests comprises a stink bug. In one example, the one or more invertebrate pests comprises a jassid e.g., a green jassid or a brown jassid. In one example, the one or more invertebrate pests comprises a mealybug. In one example, the one or more invertebrate pests comprises a locust e.g. a spur-throated locust. In one example, the one or more invertebrate pests comprises a fruit fly e.g., Queensland fruit fly. In one example, the one or more invertebrate pests comprises a pale cotton stainer.

In a particularly preferred example, the invertebrate pest is a *Helicoverpa* spp.

In another example, the invertebrate pest is a soft-bodied insect.

Alternatively, or in addition, the invertebrate pest is a pest of a plant selected from the group consisting of cotton, a grain crop, a cereal crop, an oil-seed plant, a fruit, a vegetable, a nut, a flower, turf, pasture, a vine and a legume.

For example, the invertebrate pest may be a pest of a cereal crop selected from wheat, maize, rice, oats, rye, barley, millet and sorghum. For example, the invertebrate pest may be a pest of wheat. The invertebrate pest may be a pest of maize. The invertebrate pest may be a pest of rice. The invertebrate pest may be a pest of oats. The invertebrate pest may be a pest of rye. The invertebrate pest may be a pest of barley. The invertebrate pest may be a pest of millet. The invertebrate pest may be a pest of sorghum.

In another example, the invertebrate pest is a pest of a cotton plant.

In yet another example, the invertebrate pest is a pest of a plant which is transgenic e.g., transgenic cotton. For example, the invertebrate pest may be a pest of a transgenic plant which expresses a transgene encoding a *Bacillus thuringiensis* toxin selected from a Cry toxin and a VIP toxin e.g., Bt cotton. Accordingly, as used herein, the term, "Bt cotton" will be understood to encompass transgenic cotton which express an insecticidal protein from *Bacillus thuringiensis*.

In another example, the invertebrate pest is an animal pest i.e., a pest of an animal. In such an example, the method may comprise applying the strain of *Metarhizium* spp. or the spore thereof to an animal directly. Alternatively, or in addition, the method may comprise applying the strain of *Metarhizium* spp. or the spore thereof to an area housing or containing an animal e.g., an animal shed, stall, stable, bedding material and/or paddock. Alternatively, or in addition, the method may comprise applying the strain of *Metarhizium* spp. or the spore thereof to a breeding ground or habitat of the pest.

In one example, the animal pest is an insect or arachnid e.g., such as a tick, a louse, a fly or a flea. For example, the invertebrate pest may be a tick. The invertebrate pest may be a louse. The invertebrate pest may be a fly. The invertebrate pest may be a flea.

The methods disclosed herein may be used to protect a plant or animal against, or control, multiple invertebrate pest described herein. Furthermore, it will be understood that methods disclosed herein will generally be effective against invertebrate pests during different stages of the life-cycle e.g., eggs, larvae, pupae, nymphs and/or adults.

In any of the methods disclosed herein, the strain of *Metarhizium* spp. or spore thereof may be provided in the form of a composition of the disclosure. Furthermore, the composition may be admixed with water before it is applied e.g., to a plant or its surrounding, a plant propagation material, an animal and/or a breeding ground or habitat of the invertebrate pest.

In addition, the methods disclosed herein may be performed in conjunction with the application of one or more furthers substance having insecticidal or pesticidal activity. Accordingly, any of the methods disclosure herein may comprise applying the strain of *Metarhizium* spp., spore or composition of the disclosure to a plant or its surrounding, a plant propagation material, an animal and/or a breeding ground or habitat of the invertebrate pest, in conjunction with a further substance having insecticidal or pesticidal activity. Further additional substances having insecticidal or pesticidal activity may be selected from the group consisting of abamectin, acetamiprid, alpha-cypermethrin, amitraz, amorphous silica, *Bacillus thuringiensis*, bifennthrin, chloropyrifos, chlorantraniliprole, chlorantraniliprole/thiamethoxam, clothianidin, cyantraniliprole, cypermethrin, deltamethrin, diafenthiuron, mimethoate, emamectin benzoate, esfenvalerate, fipronil, gamma-cyhalothrin, imidacloprid, indoxocarb, lambda-cyhalothrin, helicoverpa NPV, magnet, methoyl, omethoate, paraffinic oil, phorate, piperonyl butoxide, pirimicarb, pymetrozine, pyriproxyfen, spirotetramat, sulfoxaflor and thiodicarb. Further substances having insecticidal or pesticidal activity which are suitable for use in the method disclosed herein are known in the art.

The present disclosure also provides for a method of improving crop yield for a plant variety, comprising treating at least one plant and/or its surrounding e.g., soil, and/or a propagation material from which the plant is to grow and/or a breeding ground or habitat of a pest of the plant with a strain of *Metarhizium* spp. or a spore thereof. The improved crop yield is to be determined relative to a yield of a crop of the same plant variety which has not received treatment with the strain of *Metarhizium* spp. or a spore thereof. Preferably, the method of improving crop yield for a plant variety comprises performing a method of controlling an invertebrate pest as described herein. Alternatively, or in addition, the method of improving crop yield for a plant variety comprises performing a method of protecting a plant from an invertebrate pest as described herein.

In addition, the present disclosure also provides the use of a strain of *Metarhizium* spp. or spore thereof to control invertebrate pests. For example, the strain of *Metarhizium* spp. or spore thereof may be used to control invertebrate pests by applying the strain of *Metarhizium* spp. or spore thereof to a plant, its surrounding and/or a propagation material of the plant and/or to an animal and/or a to a breeding ground or habitat of the invertebrate pest e.g., in accordance with a method disclosed herein.

The present disclosure also provides the use of a strain of *Metarhizium* spp. or spore thereof to improve crop yield of a plant variety. For example, the strain of *Metarhizium* spp. or spore thereof may be used to improve crop yield of a plant variety by applying the strain of *Metarhizium* spp. or spore thereof to a plant, its surrounding and/or a propagation material of the plant and/or a to a breeding ground or habitat of the invertebrate pest e.g., in accordance with a method disclosed herein.

Preferably, the strain of *Metarhizium* spp. or the spore thereof which is provide for use is a strain or spore as disclosed herein. Even more preferably, the strain of *Metarhizium* spp. or the spore thereof which is provide for use is in the form of a composition of the present disclosure.

The present disclosure also provides a seed or plant propagation material treated with a strain of *Metarhizium* spp. or a spore thereof or a composition of the disclosure.

In one example, the seed or plant propagation material treated with a strain of *Metarhizium* spp., spore or composition of the disclosure is selected from the group consisting of cotton, a grain crop, a cereal crop, an oil-seed plant, a fruit, a vegetable, a nut, a flower, turf, pasture, a vine and a legume.

For example, the treated seed or propagation material may be from a cereal crop selected from wheat, maize, rice, oats, rye, barley, millet and sorghum. For example, the treated seed or propagation material may be from wheat. The treated seed or propagation material may be from maize. The treated seed or propagation material may be from oats. The treated seed or propagation material may be from rye. The treated seed or propagation material may be from barley. The treated seed or propagation material may be from millet. The treated seed or propagation material may be from sorghum.

In another example, the treated seed or propagation material is from a cotton plant.

The treated seed or propagation material may be from a plant which is transgenic e.g., transgenic cotton. For example, the treated seed or propagation material may be from a transgenic plant which expresses a transgene encoding a *Bacillus thuringiensis* toxin selected from a Cry toxin and a VIP toxin e.g., Bt cotton.

Each feature of any particular aspect or embodiment or example of the present disclosure may be applied mutatis mutandis to any other aspect or embodiment or example of the present disclosure.

BRIEF DESCRIPTION OF THE ACCOMPANYING DRAWINGS

FIG. 1. *Helicoverpa* $5^{th}$ instar larvae treated with fungal isolate DAT 511 turned into pupae but the pupae were then killed by the fungus.

Figure 2:
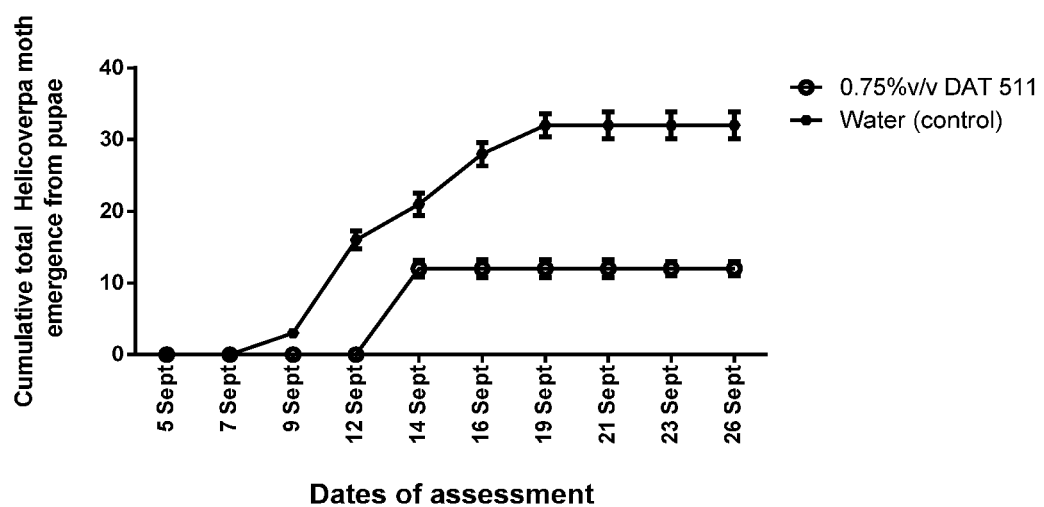

FIG. 2. Effect of varying rates of DAT 511 on adult *Helicoverpa armnigera* emergence from pupae on potted cotton plants in the mesh house.

Figure 3:
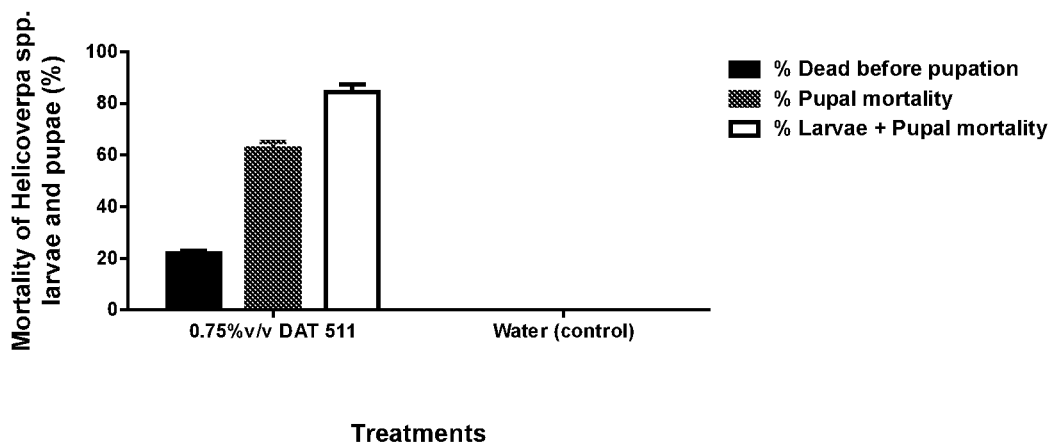

FIG. 3. Mortalities of *Helicoverpa armnigera* 5th instar larvae and pupae treated with varying rates of DAT 511 on potted cotton plants in the mesh house.

Figure 4:
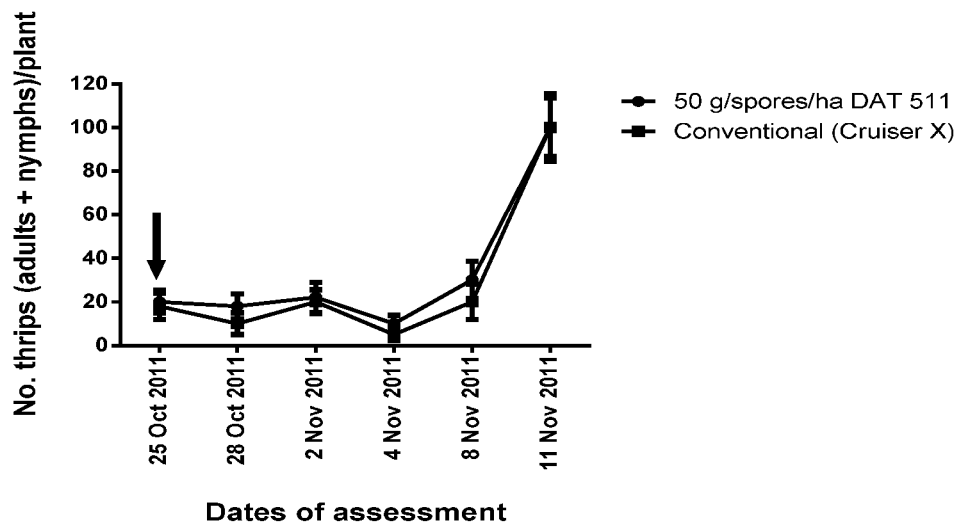

FIG. 4. Efficacy of different seed treatments in reducing the number of thrips per plant on a commercial cotton farm at Spring Ridge, NSW, 2011

Figure 5:
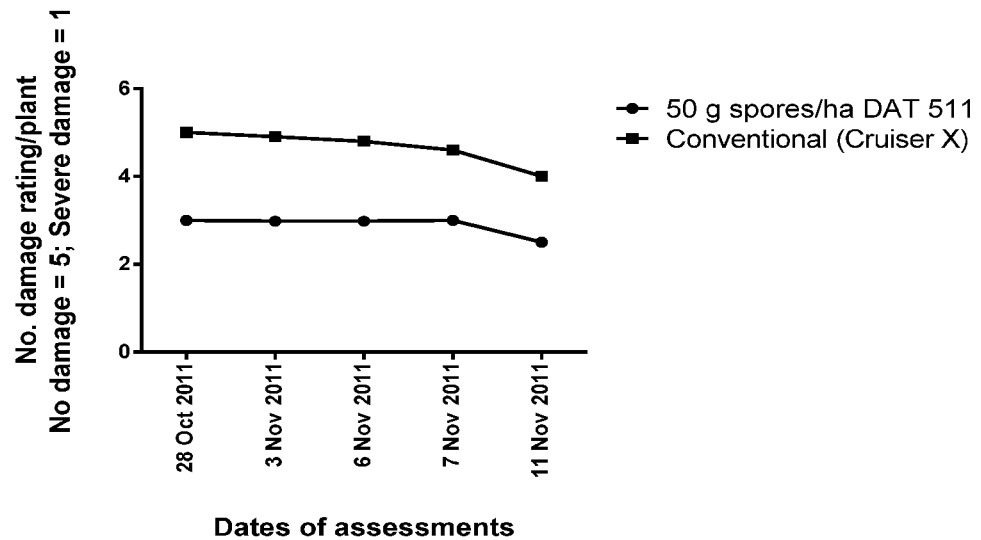

FIG. 5. Damage of seedlings in plots treated with DAT 511 and Cruiser X on a commercial cotton farm at Spring Ridge, N S W, 2011 (no damage=5; severe damage=1)

Figure 6:
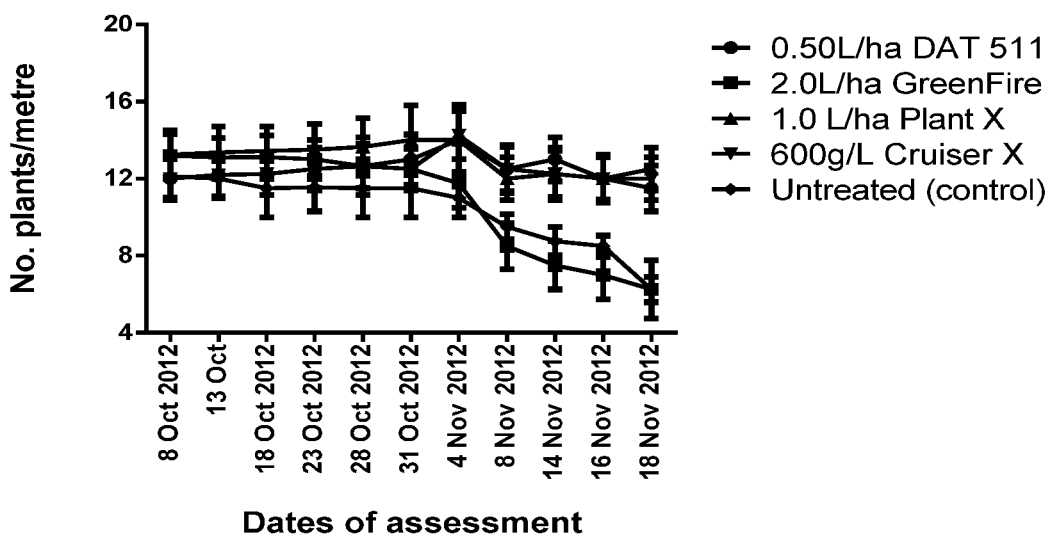

FIG. 6. Efficacy of biological and insecticidal seed treatments on cotton plant stand (germinability) on a commercial cotton farm at Norwood, Moree, September-November 2012

Figure 7:
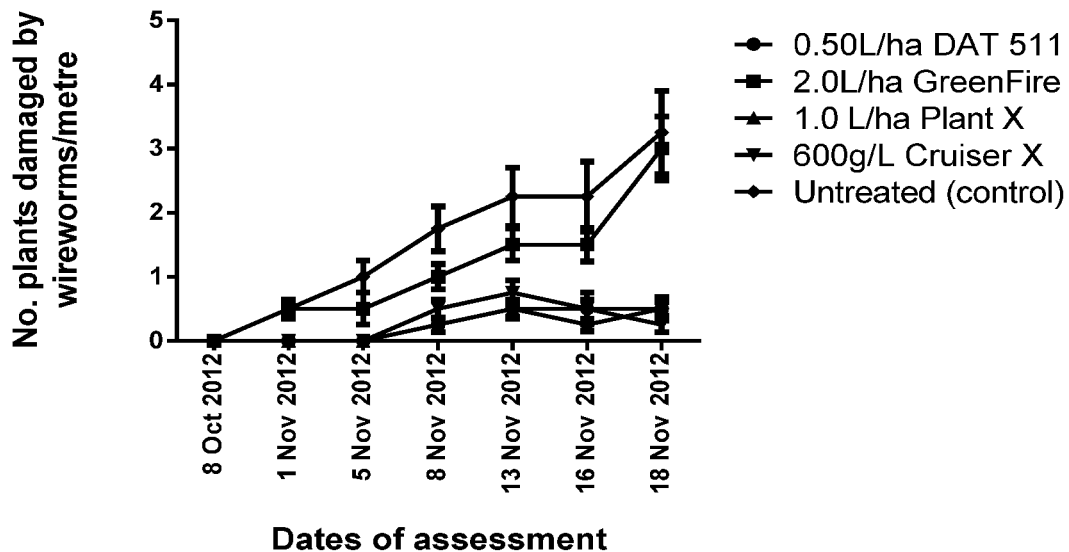

FIG. 7. Efficacy of biological and insecticidal seed treatments in reducing wireworm damage to cotton plants on a commercial cotton farm at Norwood, Moree, September-November 2012

Figure 8:
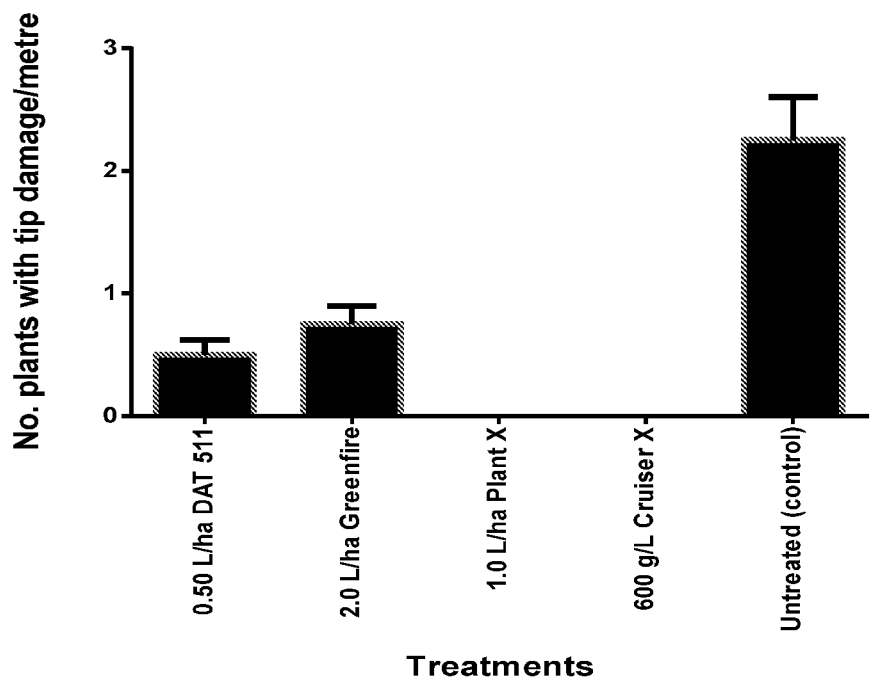

FIG. 8. Efficacy of biological and insecticidal seed treatments in reducing thrips damage to cotton plants on a commercial cotton farm at Norwood, Moree, 2012.

Figure 9:
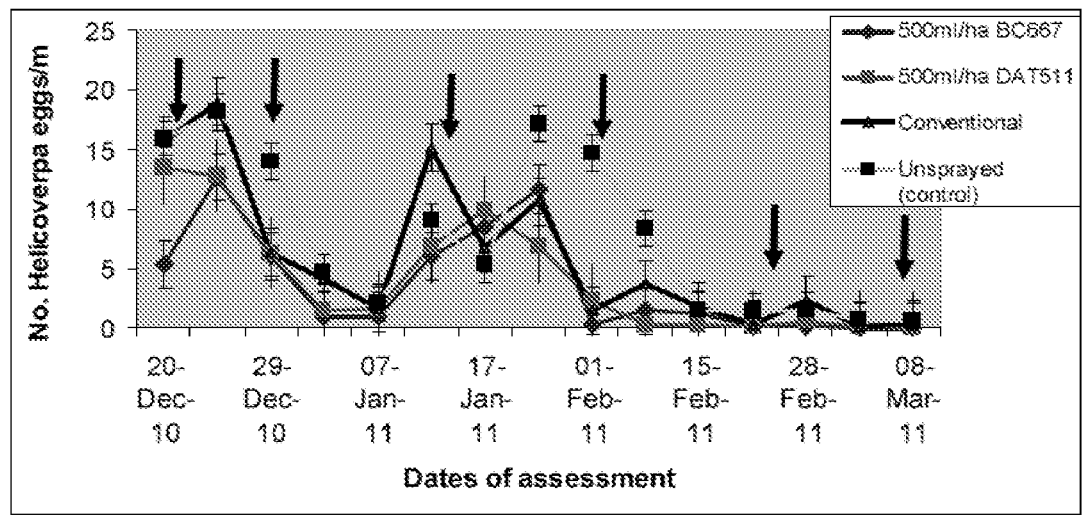

FIG. 9. Efficacy of BC 667 and DAT 511 against *Helicoverpa* spp. eggs on conventional cotton crops at Australian Cotton Research Institute (ACRI) during the 2010-2011 season. Arrows indicate spray dates. In the BC 667 and DAT 511 plots, the spray applied on 1 Feb. 2011 was mixed with Indoxacarb (half rate) to reduce the number of medium and large *Helicoverpa* spp. larvae.

Figure 10:
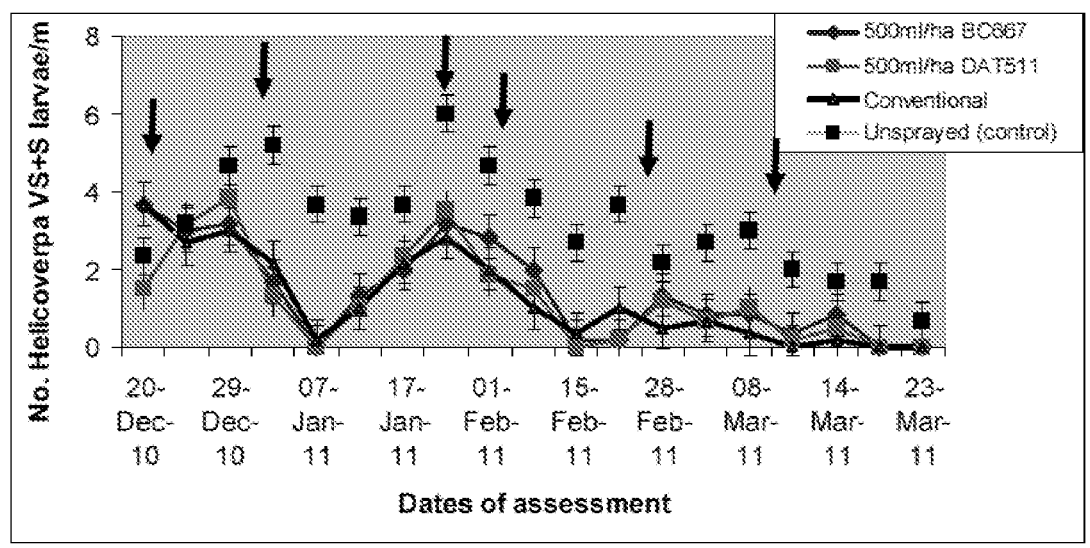

FIG. 10. Efficacy of BC 667 and DAT 511 against *Helicoverpa* spp. very small and small larvae on conventional cotton crops at Australian Cotton Research Institute (ACRI) during the 2010-2011 season. Arrows indicate spray dates. On the BC 667 and DAT 511 plots, the spray applied on 1 Feb. 2011 was mixed with Indoxacarb (half rate) to reduce the number of medium and large *Helicoverpa* spp. larvae.

Figure 11:
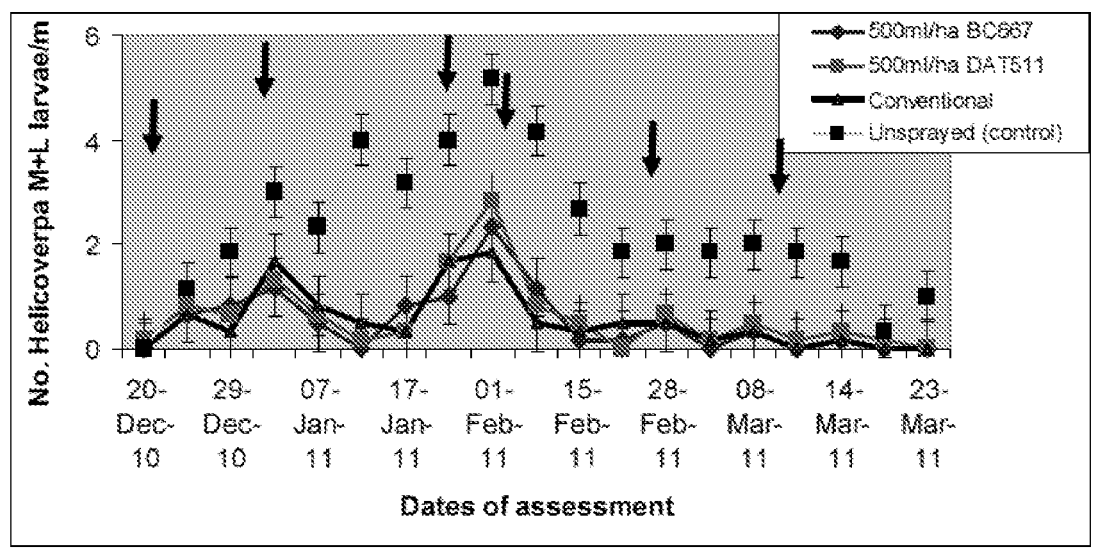

FIG. 11. Efficacy of BC 667 and DAT 511 against *Helicoverpa* spp. medium and large larvae on conventional cotton crops at Australian Cotton Research Institute (ACRI) during the 2010-2011 season. Arrows indicate spray dates. On the BC 667 and DAT 511 plots, the spray applied on 1 Feb. 2011 was mixed with Indoxacarb (half rate) to reduce number of medium and large *Helicoverpa* spp. larvae.

Figure 12:
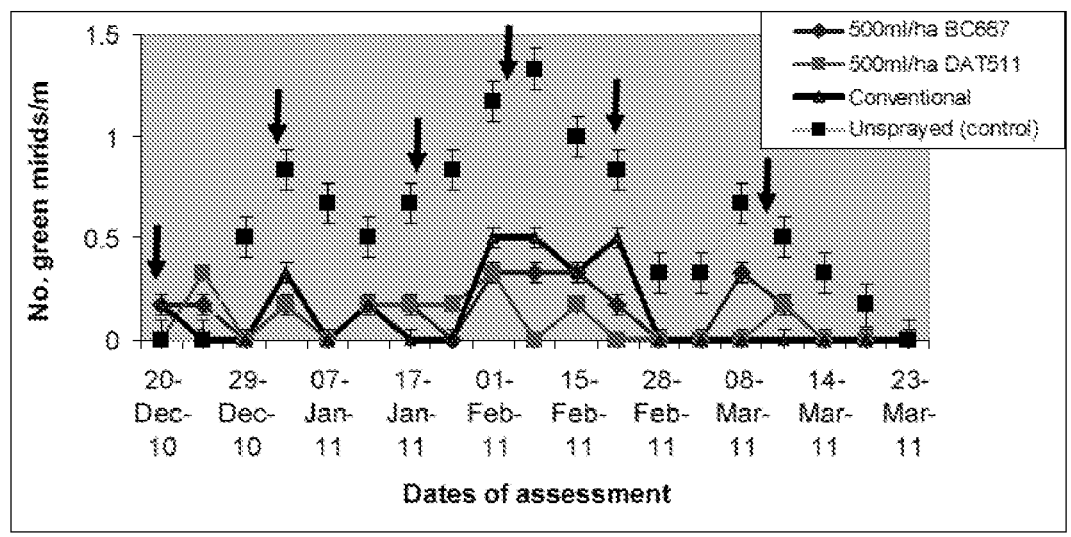

FIG. 12. Efficacy of BC 667 and DAT 511 against green mirids on conventional cotton crops at Australian Cotton Research Institute (ACRI) during the 2010-2011 season.

Figure 13:
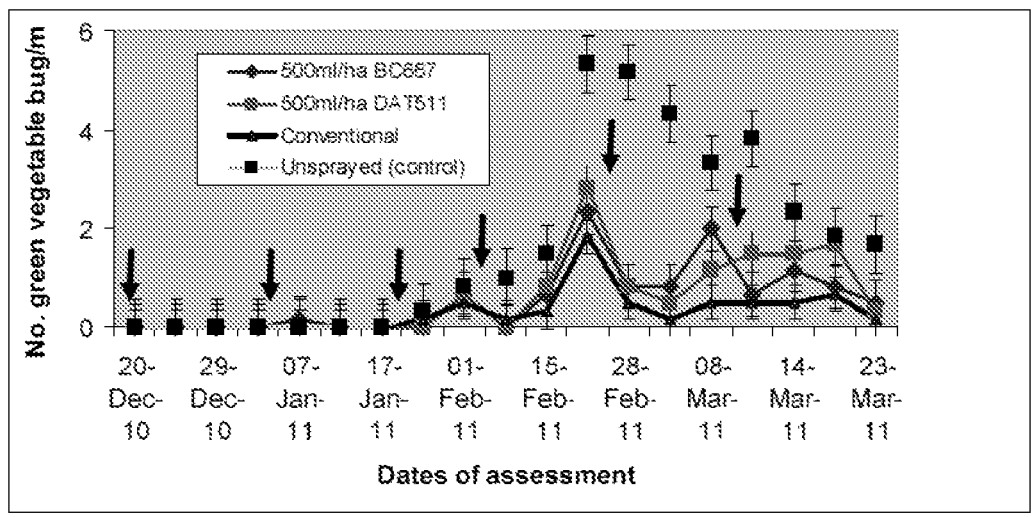

FIG. 13. Efficacy of BC 667 and DAT 511 against green vegetable bugs on conventional cotton crops at Australian Cotton Research Institute (ACRI) during the 2010-2011 season.

Figure 14:
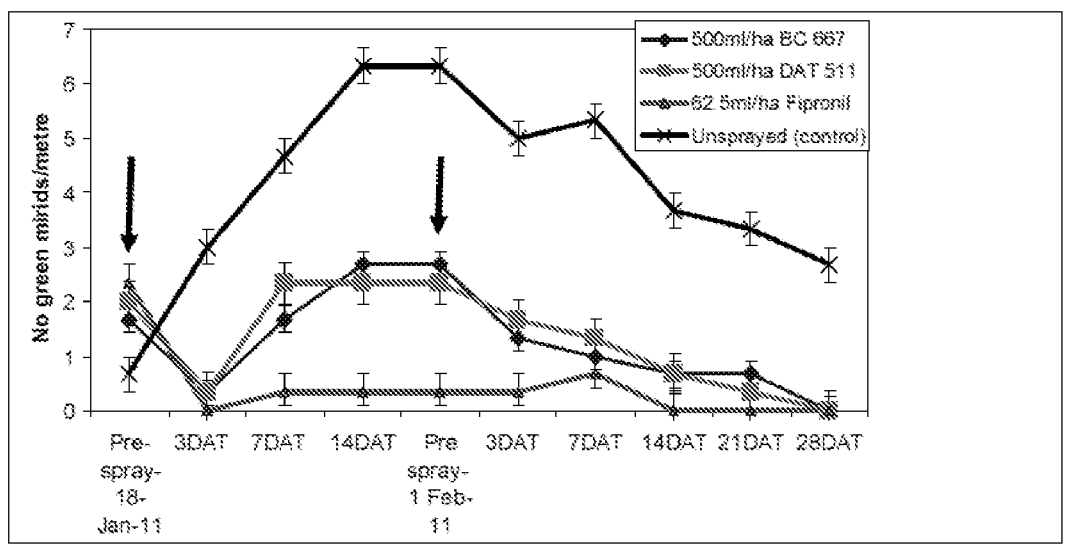

FIG. 14. Efficacy of BC 667 and DAT 511 against green mirids on Bollgard cotton crops at Norwood, near Moree, during the 2010-2011 season.

Figure 15:
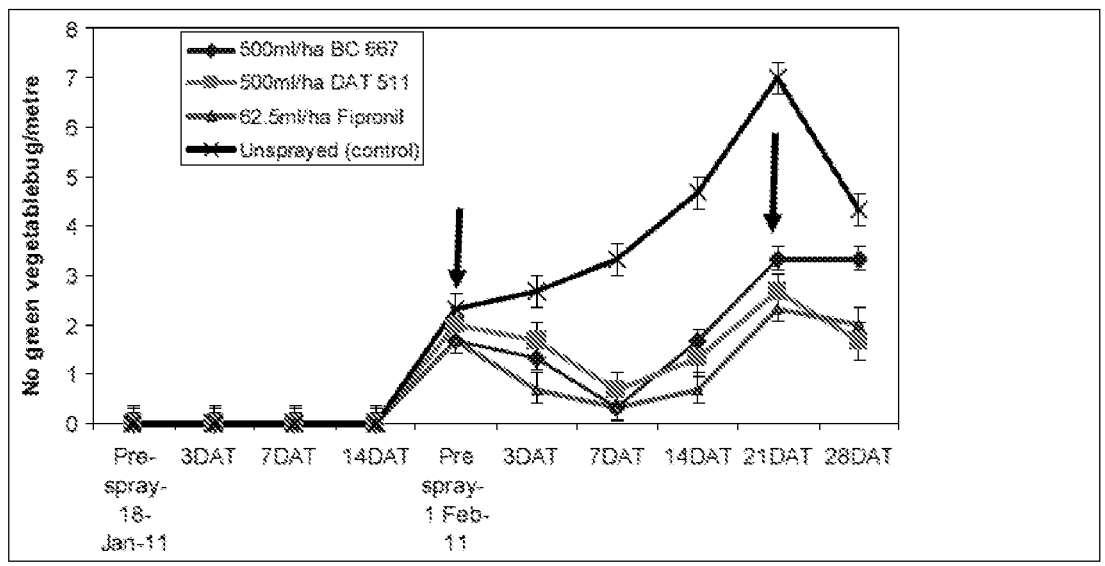

FIG. 15. Efficacy of BC 667 and DAT 511 against green vegetable bugs on Bollgard cotton crops at Norwood, near Moree, during the 2010-2011 season.

Figure 16:
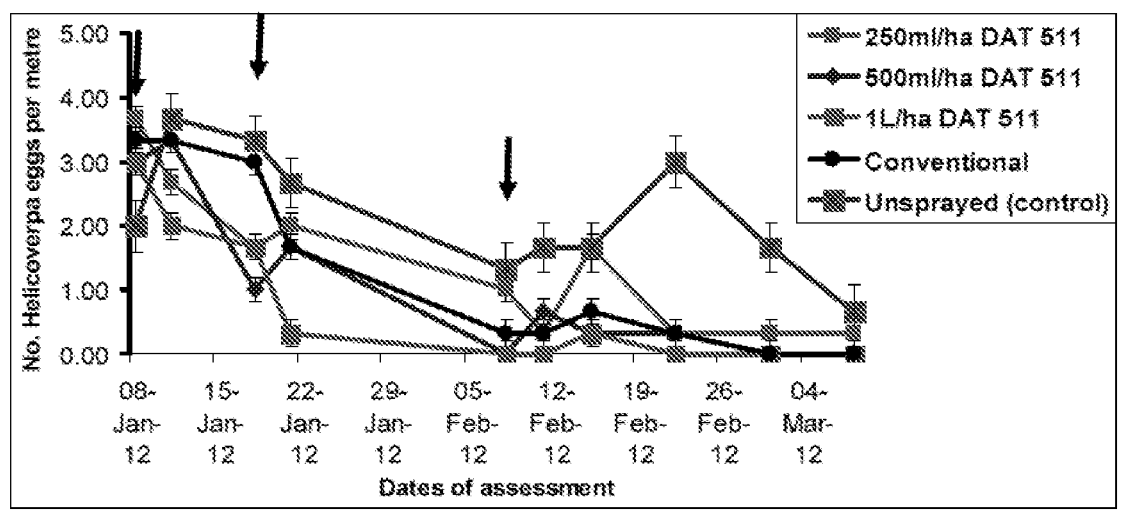

FIG. 16. Efficacy of different rates of DAT 511 in reducing numbers of *Helicoverpa* spp. eggs on conventional cotton crops at Australian Cotton Research Institute (ACRI) during the 2011-2012 season. The arrows indicate the date of treatment for DAT 511 and error bars indicate standard error of the mean.

Figure 17:
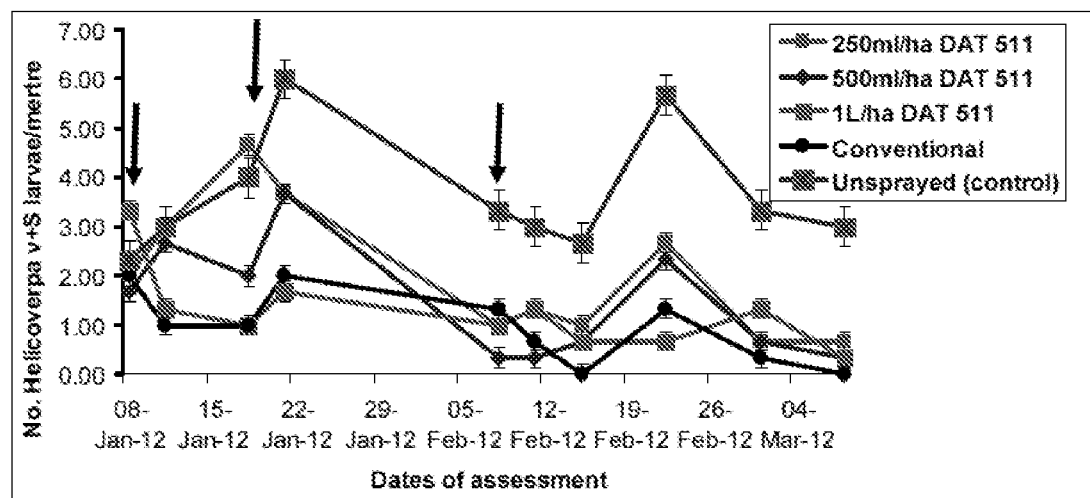

FIG. 17. Efficacy of different rates of DAT 511 in reducing numbers of *Helicoverpa* spp. very small and small larvae on conventional cotton crops at Australian Cotton Research Institute (ACRI) during the 2011-2012 season.

Figure 18:
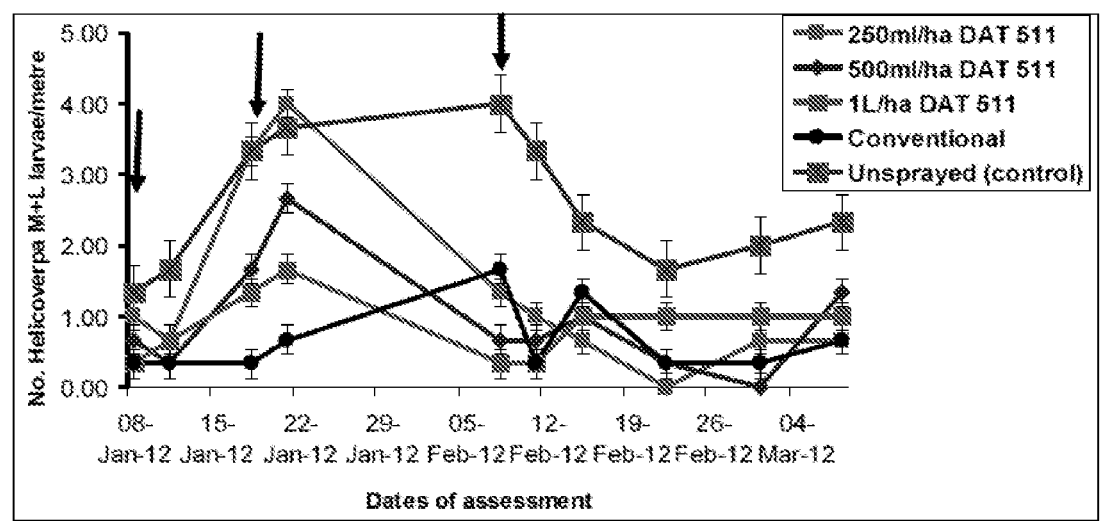

FIG. 18. Efficacy of different rates of DAT 511 in reducing numbers of *Helicoverpa* spp. medium and large larvae on conventional cotton crops at Australian Cotton Research Institute (ACRI) during the 2011-2012 season.

Figure 19:
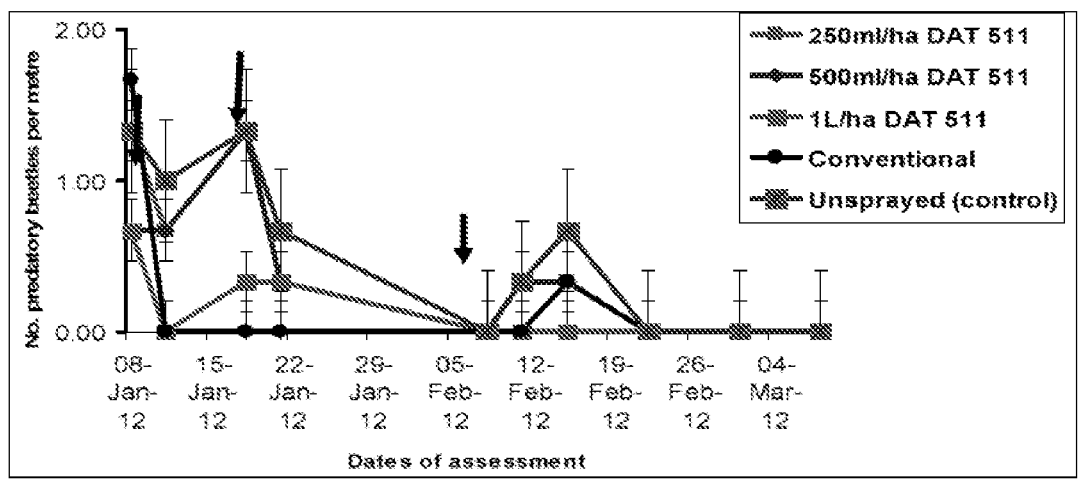

FIG. 19. Efficacy of different rates of DAT 511 in reducing numbers of predatory beetles on conventional cotton crops at Australian Cotton Research Institute (ACRI) during the 2011-2012 season.

Figure 20:
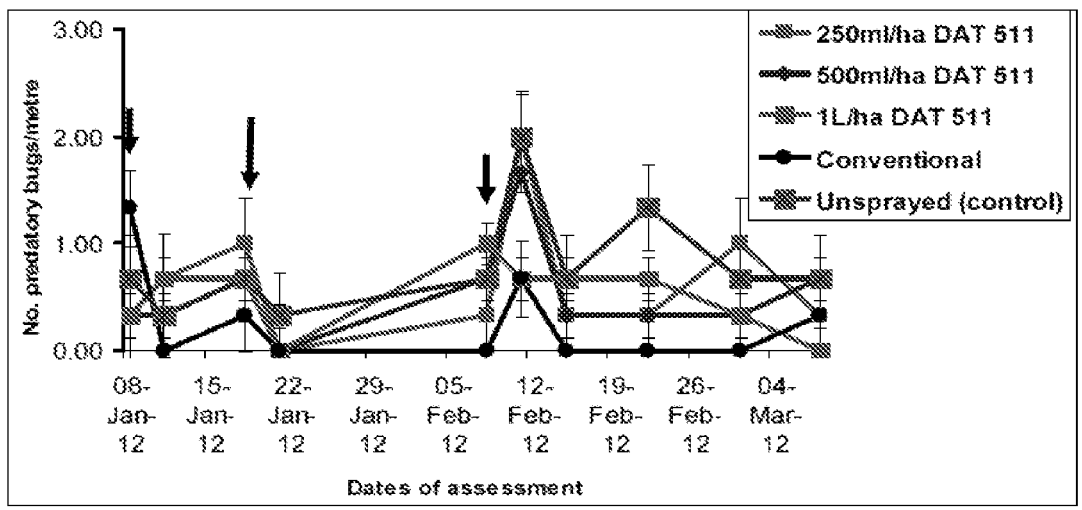

FIG. 20. Efficacy of different rates of DAT 511 in reducing numbers of predatory bugs on conventional cotton crops at Australian Cotton Research Institute (ACRI) during the 2011-2012 season.

Figure 21:
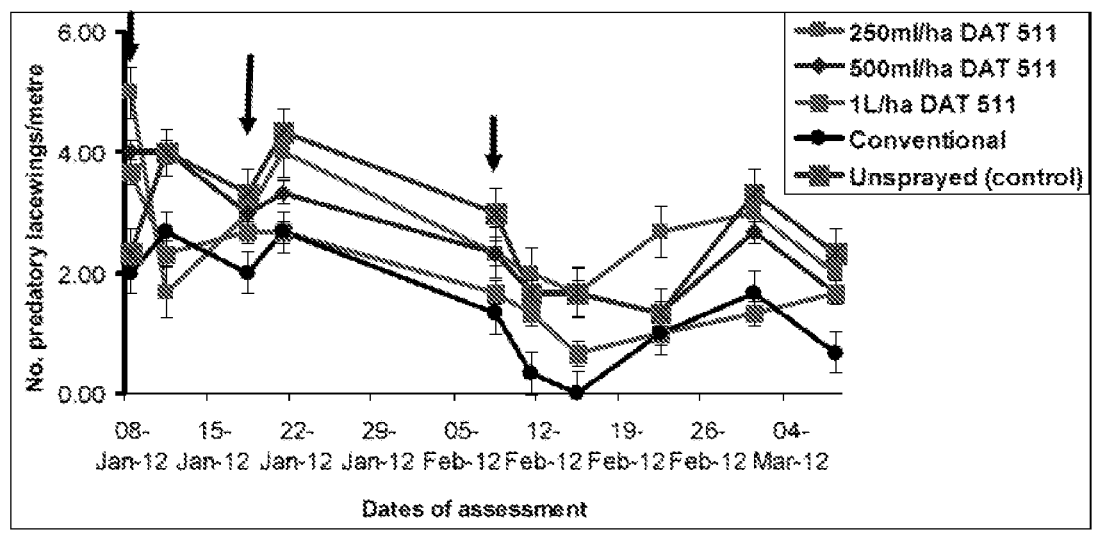

FIG. 21. Efficacy of different rates of DAT 511 in reducing numbers of predatory lacewings on conventional cotton crops at Australian Cotton Research Institute (ACRI) during the 2011-2012 season.

Figure 22:
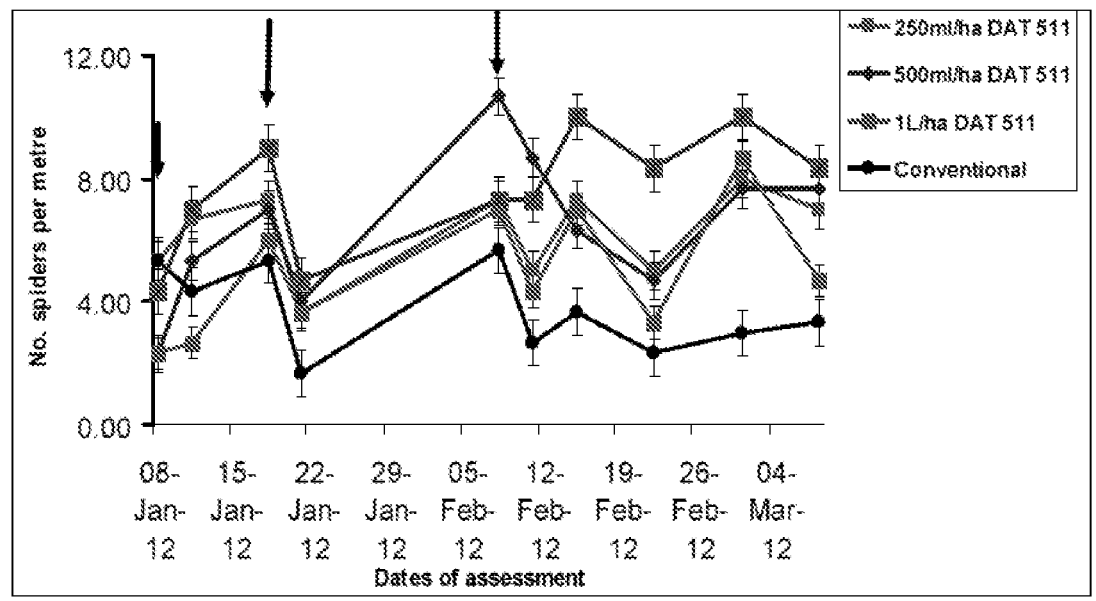

FIG. 22. Efficacy of different rates of DAT 511 in reducing numbers of spiders on conventional cotton crops at Australian Cotton Research Institute (ACRI) during the 2011-2012 season.

Figure 23:
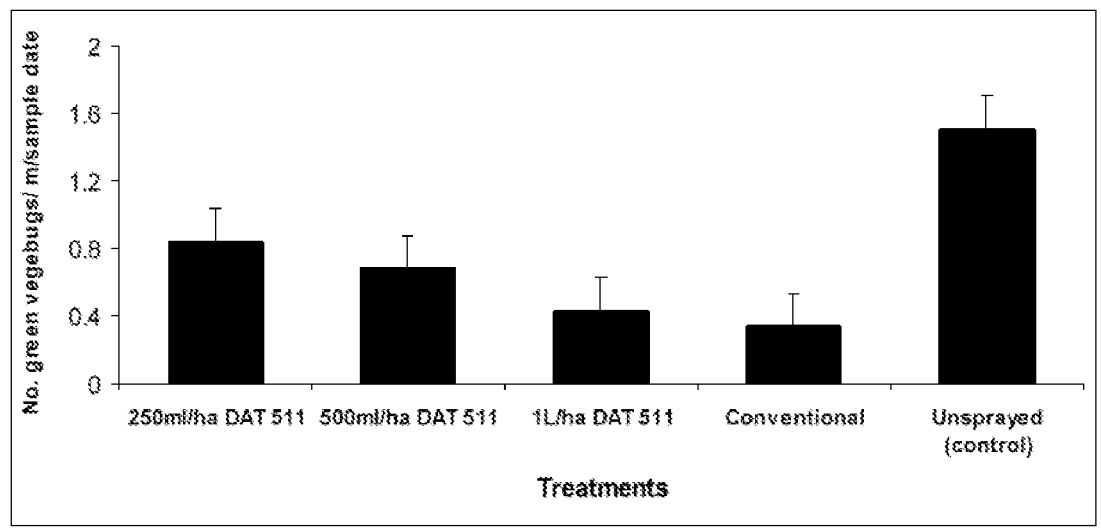

FIG. 23. Efficacy of DAT 511 and conventional insecticides on the number of adult and nymph green vegetable bugs on conventional cotton crops at the Australian Cotton Research Institute (ACRI) during the 2011-2012 season. The error bars indicate standard error of the mean.

Figure 24:
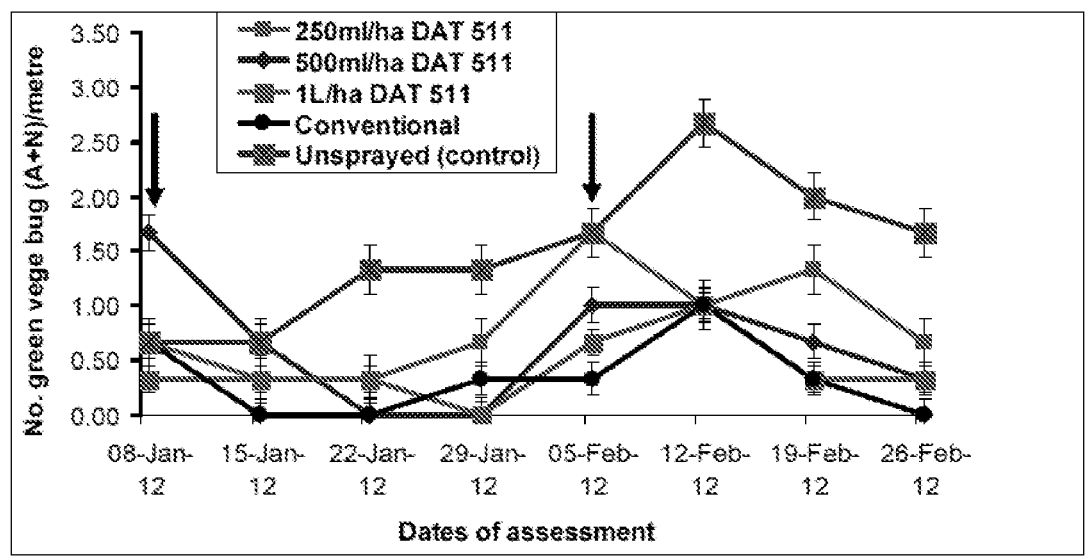

FIG. 24. Efficacy of different rates of DAT 511 and conventional insecticides in reducing numbers of adult and nymph green vegetable bugs on conventional cotton crops at the Australian Cotton Research Institute (ACRI) during the 2011-2012 season. The arrow indicates the date of treatment with fungus DAT 511 and error bars indicate standard error of the mean.

Figure 25:
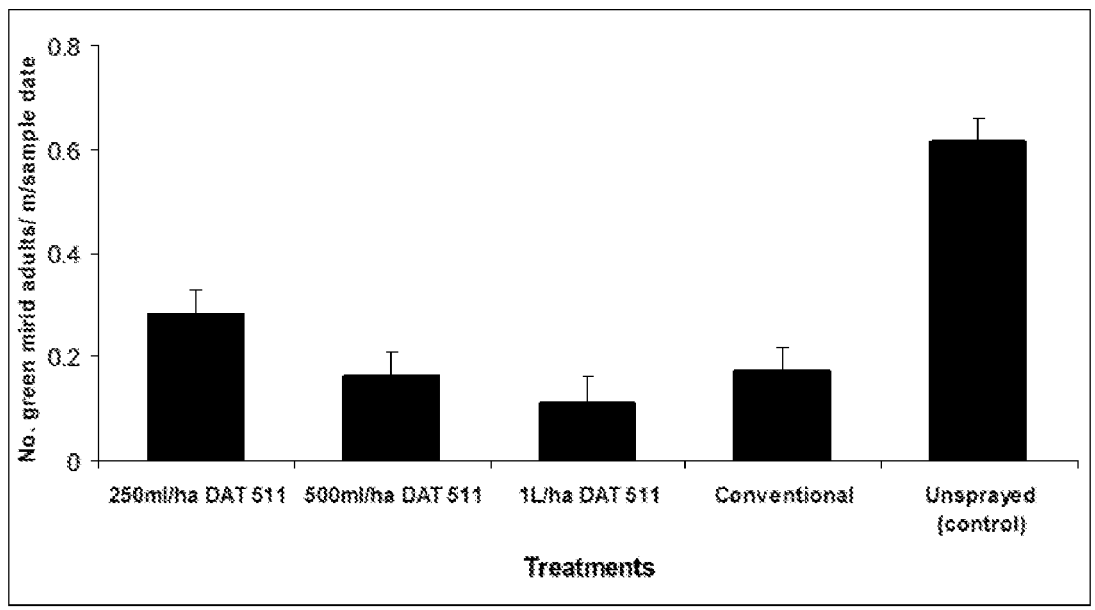

FIG. 25. Efficacy of DAT 511 and conventional insecticides in reducing the number of green mirid adults on conventional cotton crops at Australian Cotton Research Institute (ACRI) during the 2011-2012 season. The error bars indicate standard error of the mean.

Figure 26:
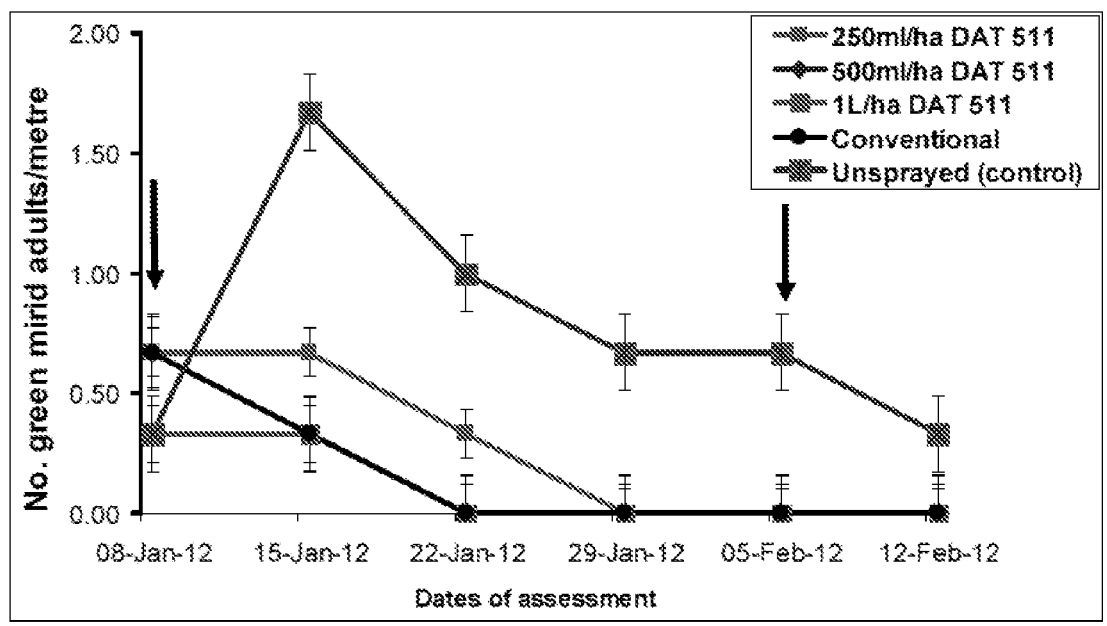

FIG. 26. Efficacy of different rates of fungus DAT 511 in reducing numbers of *Creontiades dilutus* (green mirid) adults on conventional cotton crops at the Australian Cotton Research Institute (ACRI) during the 2011-2012 season. The arrow indicates the date of treatment with fungus DAT 511 and error bars indicate standard error of the mean.

Figure 27:
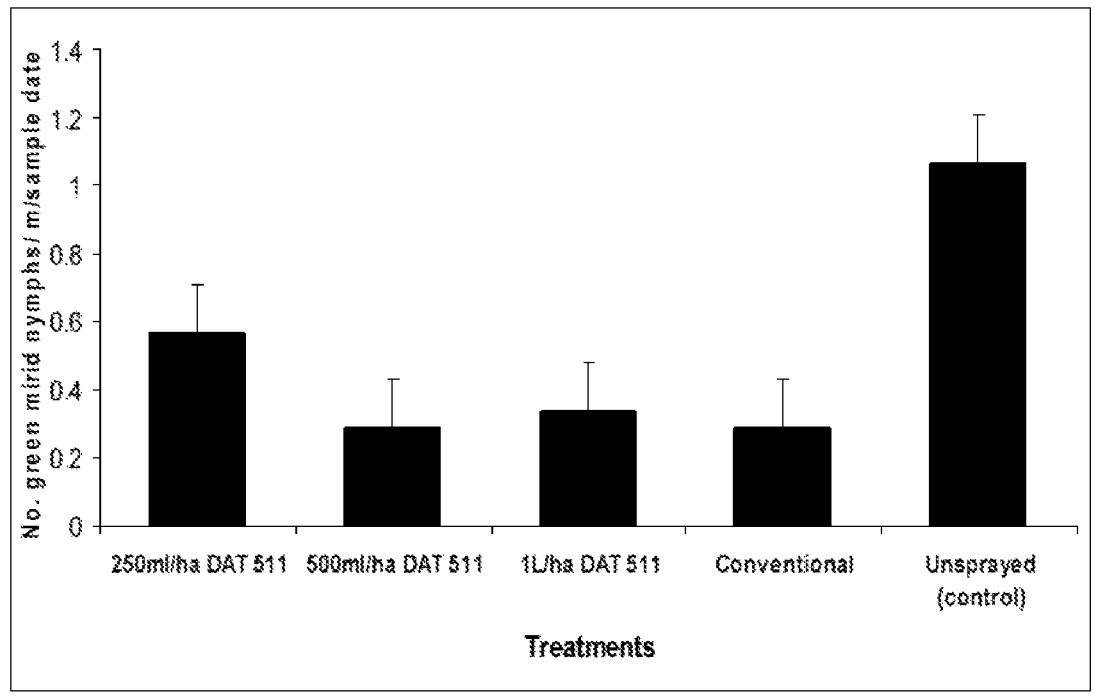

FIG. 27. Efficacy of DAT 511 and conventional insecticides in reducing the number of green mirid nymphs on conventional cotton crops at Australian Cotton Research Institute (ACRI) during the season of 2011-2012. The error bars indicate standard error of the mean.

Figure 28:
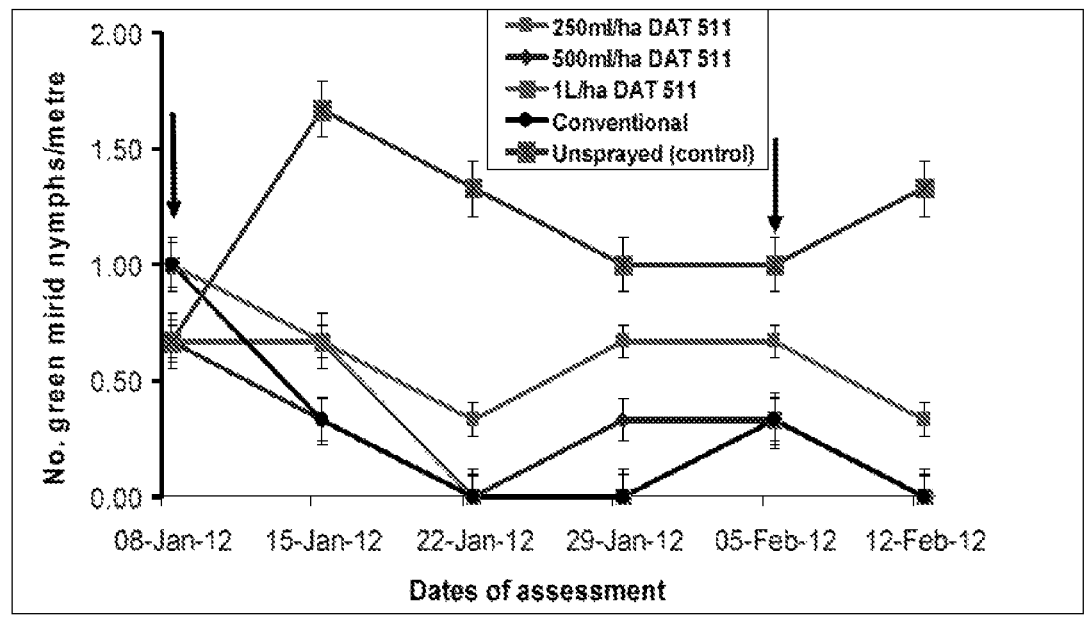

FIG. 28. Efficacy of different rates of application of fungus DAT 511 in reducing numbers of *Creontiades dilutus* (green mirid) nymphs on conventional cotton crops at the Australian Cotton Research Institute (ACRI) during the 2011-2012 season. The arrow indicates the date of treatment with fungus DAT 511 and error bars indicate standard error of the mean.

Figure 29:
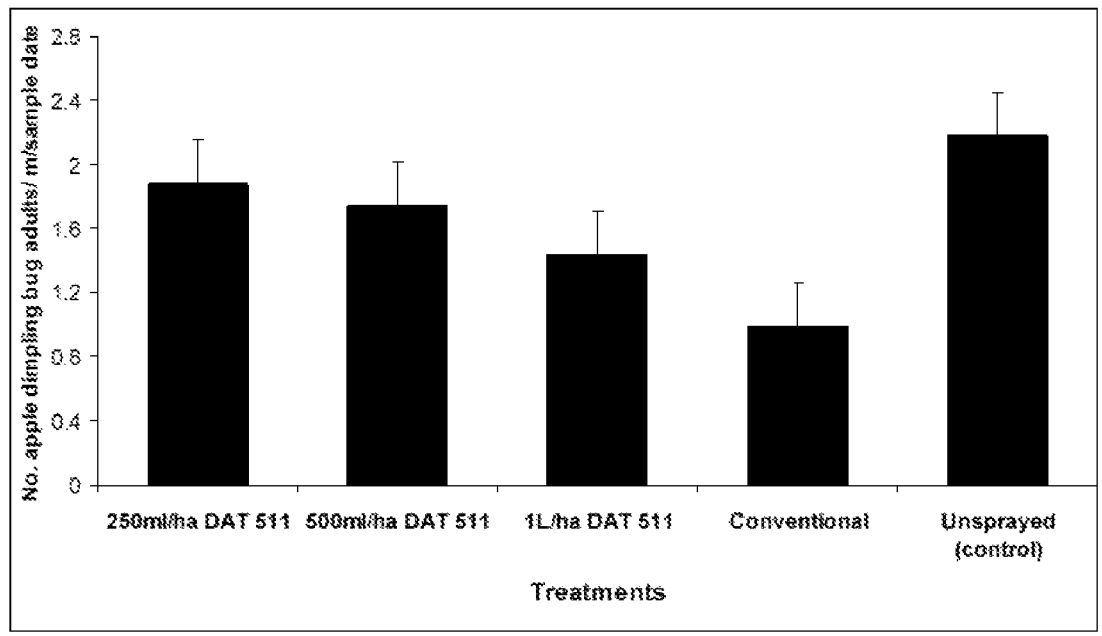

FIG. 29. Efficacy of DAT 511 and conventional insecticides in reducing the number of apple dimpling bug adults on conventional cotton crops at Australian Cotton Research Institute (ACRI) during the 2011-2012 season. The error bars indicate standard error of the mean.

Figure 30:
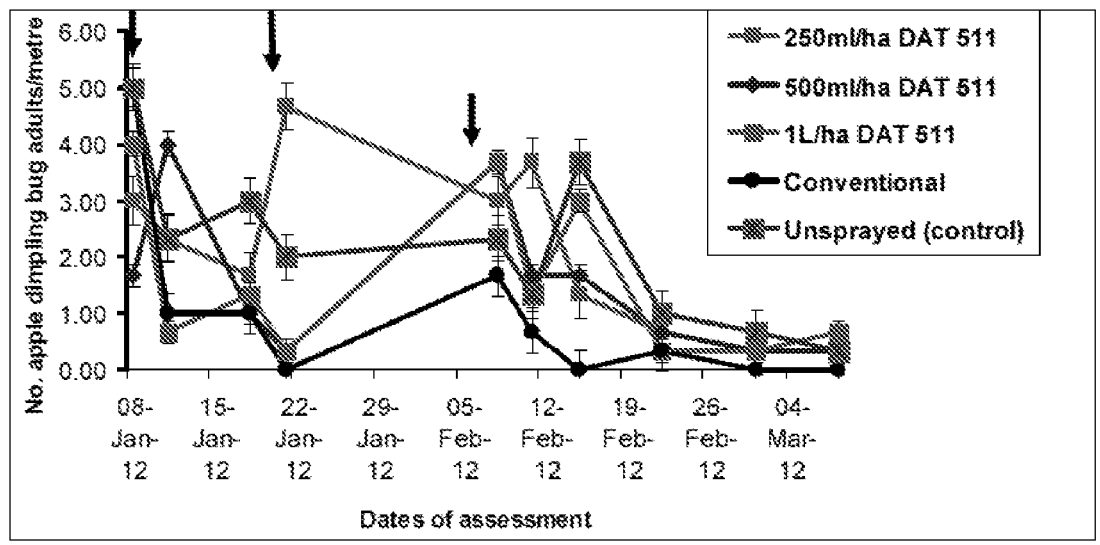

FIG. 30. Efficacy of DAT 511 and conventional insecticides in reducing the number of apple dimpling bug adults on conventional cotton crops at Australian Cotton Research Institute (ACRI) during the 2011-2012 season. The arrow indicates the date of treatment with fungus DAT 511 and error bars indicate standard error of the mean.

Figure 31:
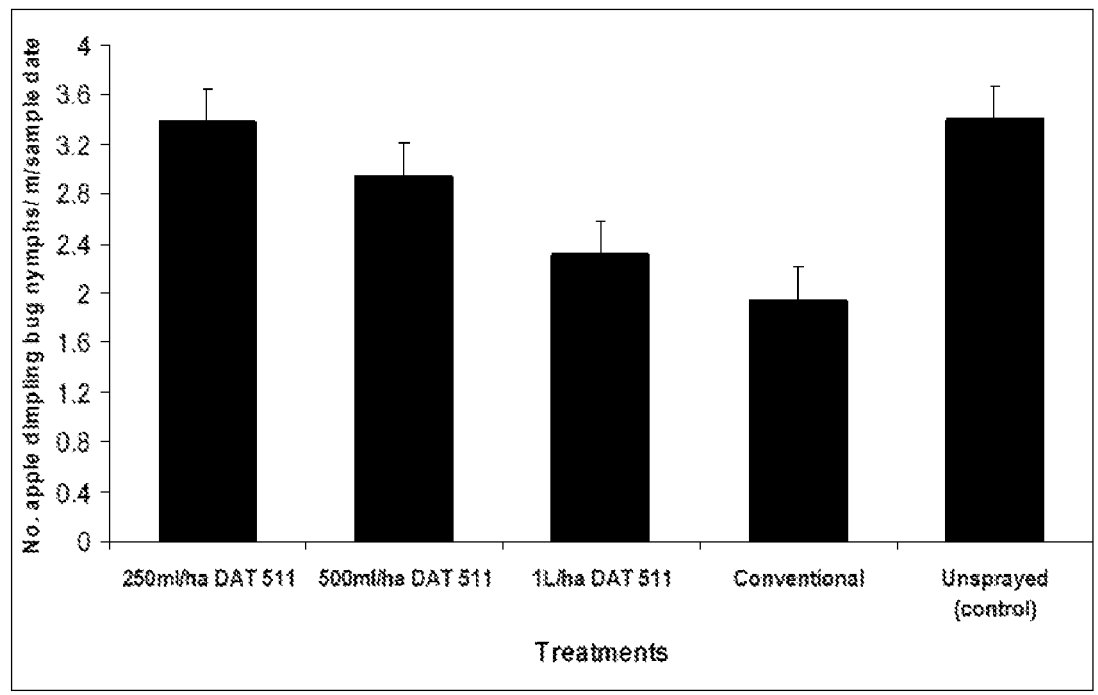

FIG. 31. Efficacy of DAT 511 and conventional insecticides in reducing the number of apple dimpling bug nymphs on conventional cotton crops at Australian Cotton Research Institute (ACRI) during the 2011-2012 season. The error bars indicate standard error of the mean.

Figure 32:
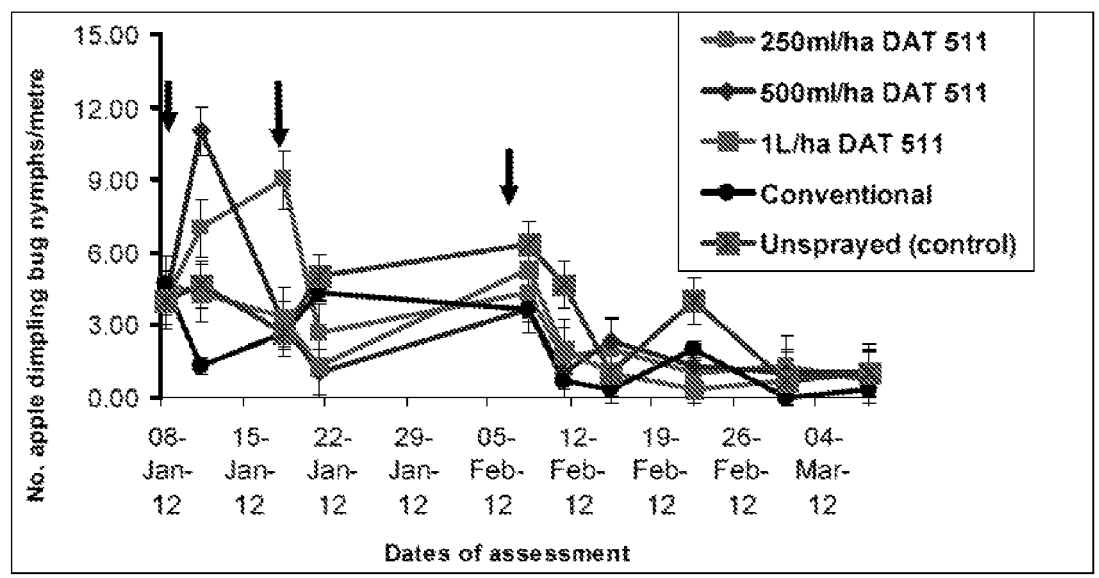

FIG. 32. Efficacy of DAT 511 and conventional insecticides in reducing the number of apple dimpling bug adults on conventional cotton crops at Australian Cotton Research Institute (ACRI) during the 2011-2012 season. The arrow indicates the date of treatment with fungus DAT 511 and error bars indicate standard error of the mean.

Figure 33:
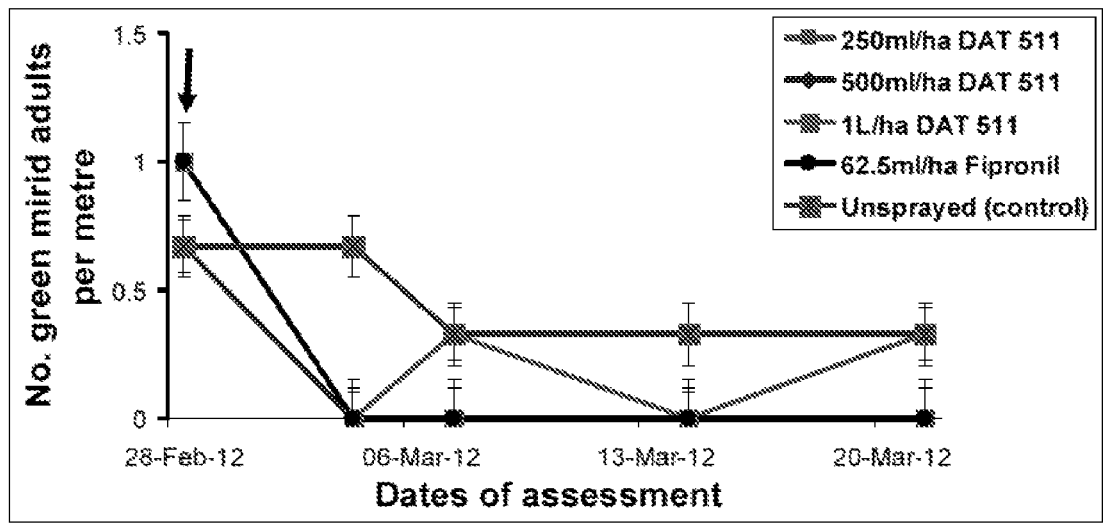

FIG. 33. Efficacy of DAT 511 and conventional synthetic insecticides in reducing the number of green mirid adults on commercial conventional cotton crops at Norwood, near Moree, during the 2011-2012 season. Arrows indicate dates of treatment and error bars indicate standard error of the mean.

Figure 34:
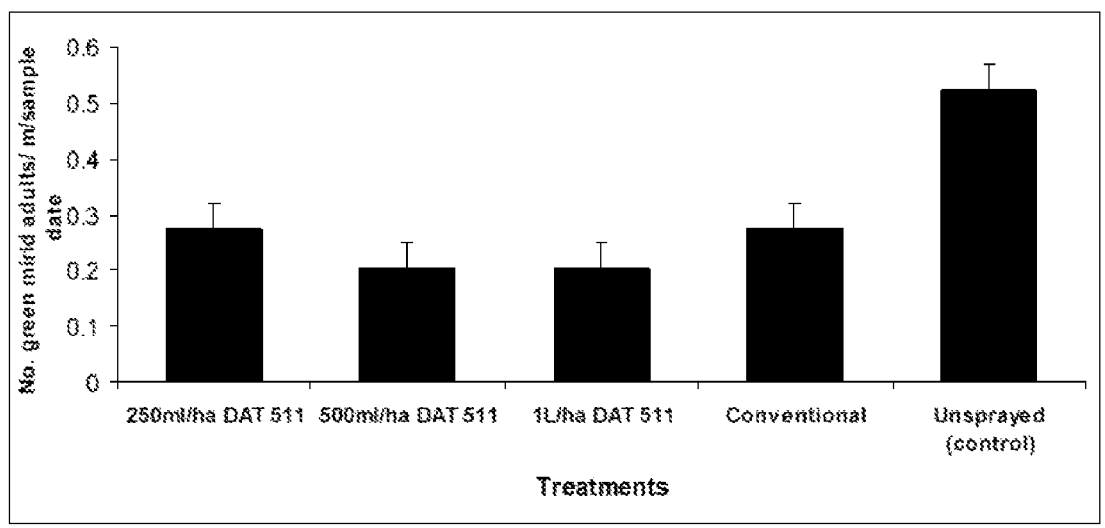

FIG. 34. Green mirid adult populations in plots treated with DAT 511 fungus and conventional synthetic insecticides on commercial conventional cotton crops at Norwood, near Moree, during the 2011-2012 season. Arrows indicate dates of treatment and error bars indicate standard error of the mean.

Figure 35:
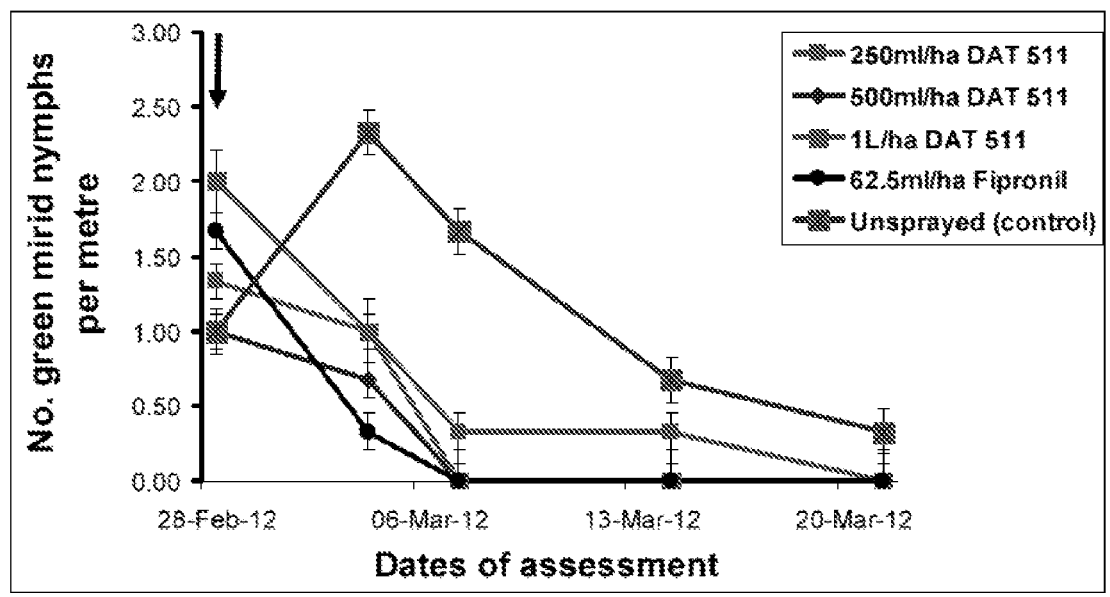

FIG. 35. Efficacy of DAT 511 and conventional synthetic insecticides in reducing the number of green mirid nymphs on commercial conventional cotton crops at Norwood, near Moree, during the 2011-2012 season. Arrows indicate dates of treatment and error bars indicate standard error of the mean.

Figure 36:
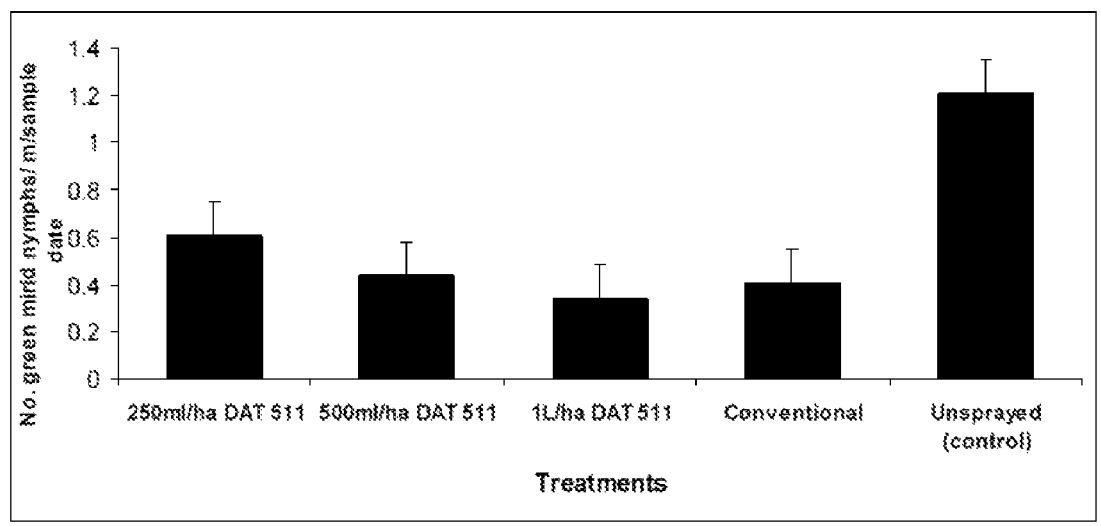

FIG. 36. Green mirid adult populations in plots treated with DAT 511 fungus and conventional synthetic insecticides on commercial conventional cotton crops at Norwood, near Moree, during the 2011-2012 season. Arrows indicate dates of treatment and error bars indicate standard error of the mean.

Figure 37:
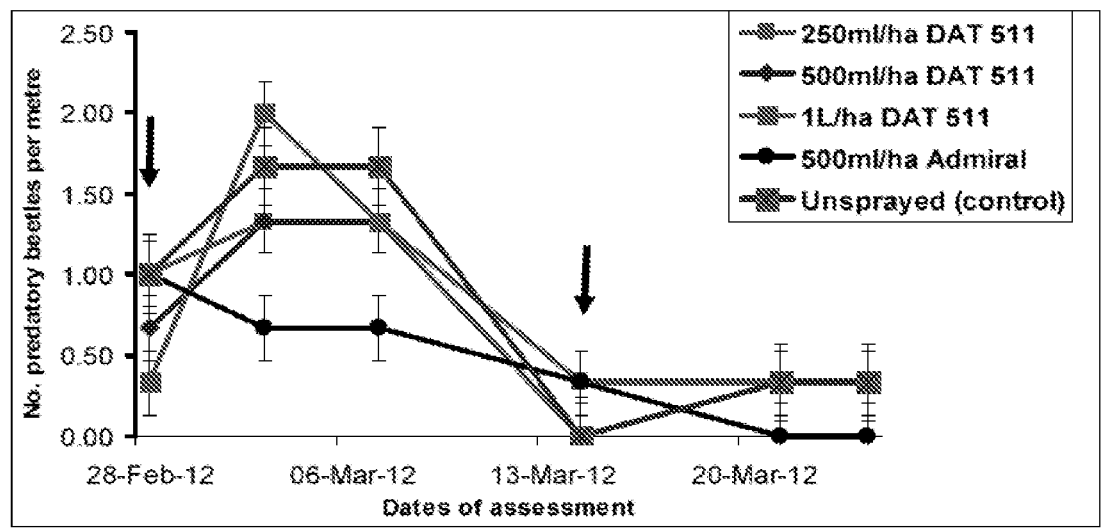

FIG. 37. Efficacy of different rates of fungus DAT 511 in reducing numbers of predatory beetles on conventional cotton crops at Norwood near Moree during the 2011-2012 season. The arrow indicates the date of treatment with fungus DAT 511 and error bars indicate standard error of the mean.

Figure 38:
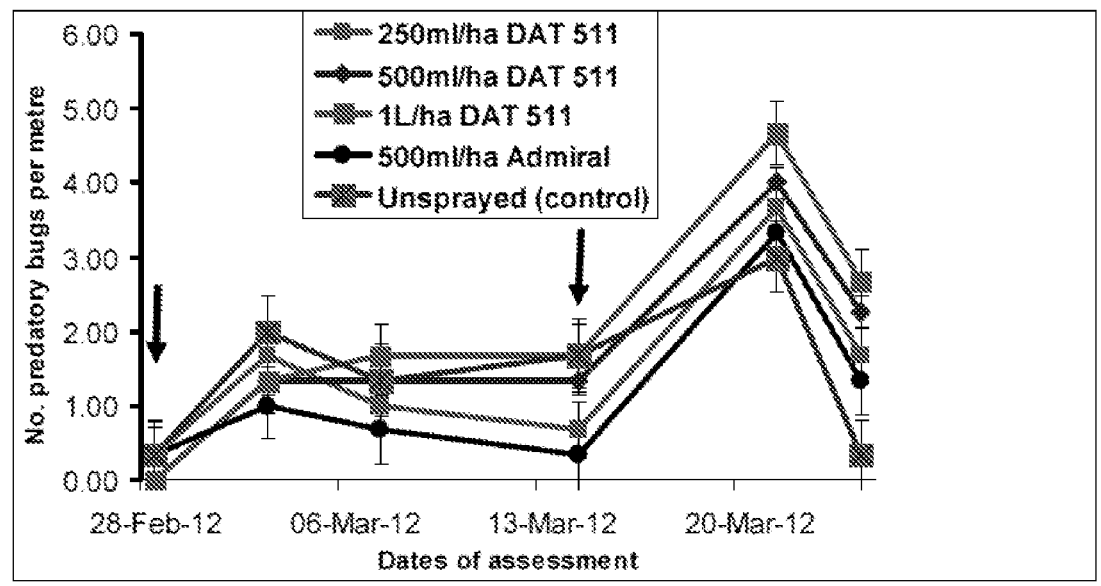

FIG. 38. Efficacy of different rates of fungus DAT 511 in reducing numbers of predatory bugs on conventional cotton crops at the Norwood near Moree during the 2011-2012 season. The arrow indicates the date of treatment with fungus DAT 511 and error bars indicate standard error of the mean.

Figure 39:
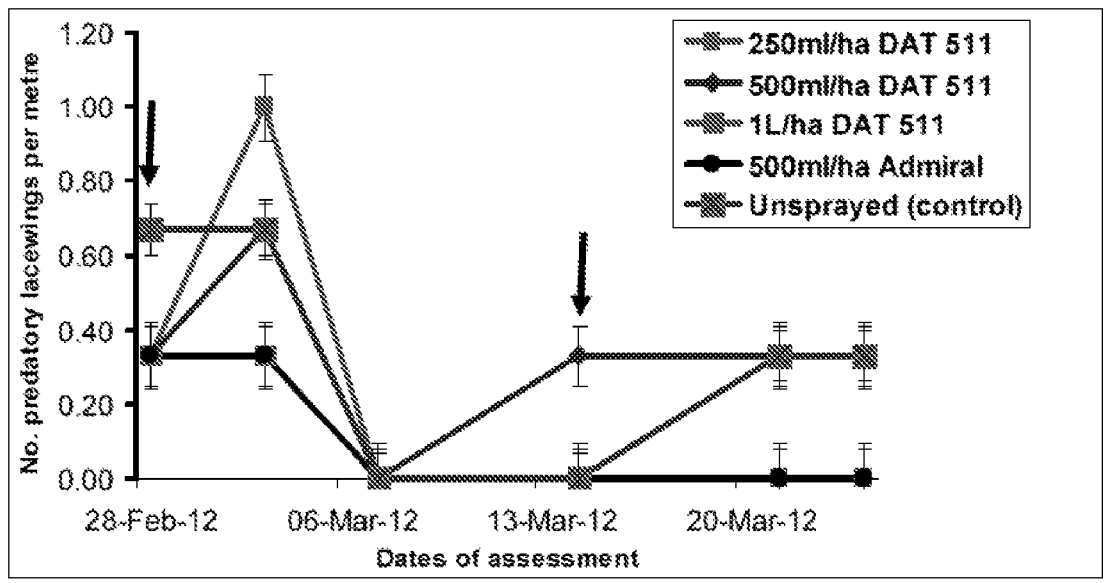

FIG. 39. Efficacy of different rates of application of fungus DAT 511 in reducing numbers of predatory bugs on conventional cotton crops at the Norwood near Moree during the 2011-12 season. The arrow indicates the date of treatment with fungus DAT 511 and error bars indicate standard error of the mean.

Figure 40:
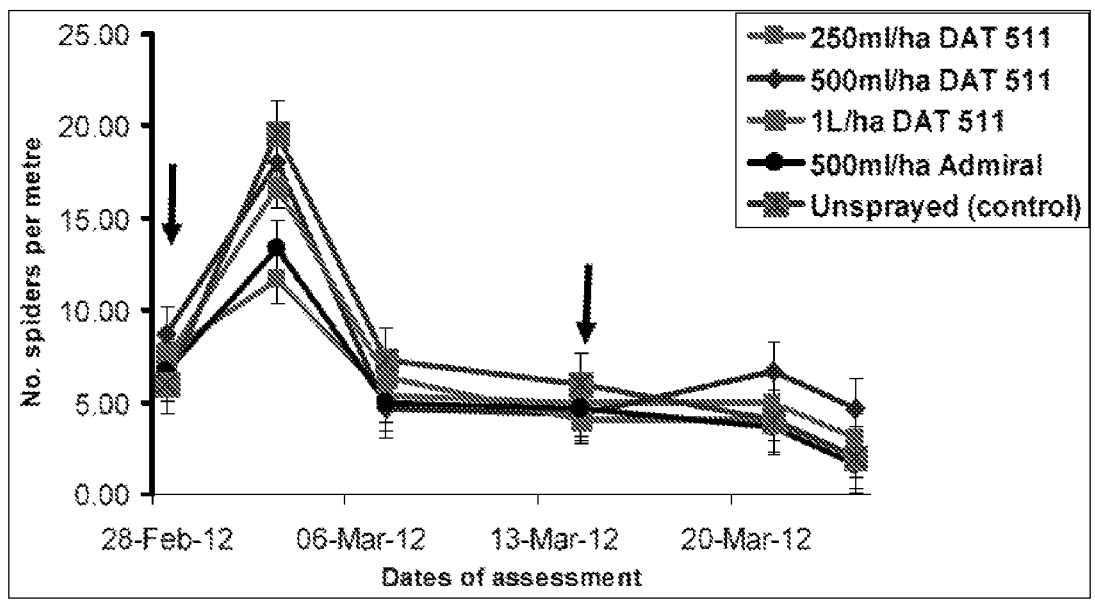

FIG. 40. Efficacy of different rates of fungus DAT 511 in reducing numbers of predatory bugs on conventional cotton crops at the Norwood near Moree during the 2011-2012 season. The arrow indicates the date of treatment with fungus DAT 511 and error bars indicate standard error of the mean.

Figure 41A:
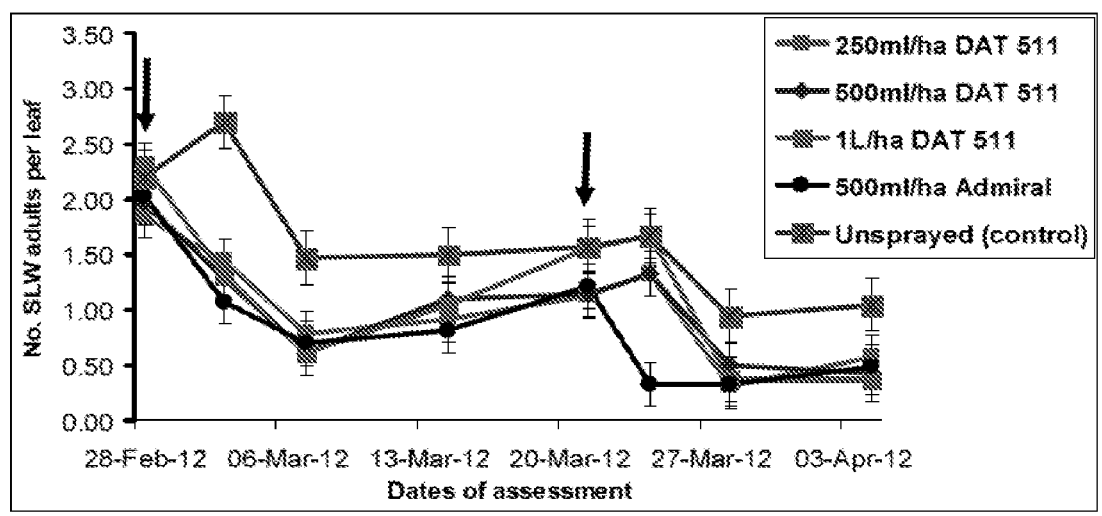

FIG. 41. Efficacy of DAT 511 and conventional insecticides in reducing the number of silverleaf whitefly adults (A) and silverleaf whitefly nymphs (B) on conventional cotton crops at Norwood in Moree, during the 2011-2012 season.

Figure 42A:
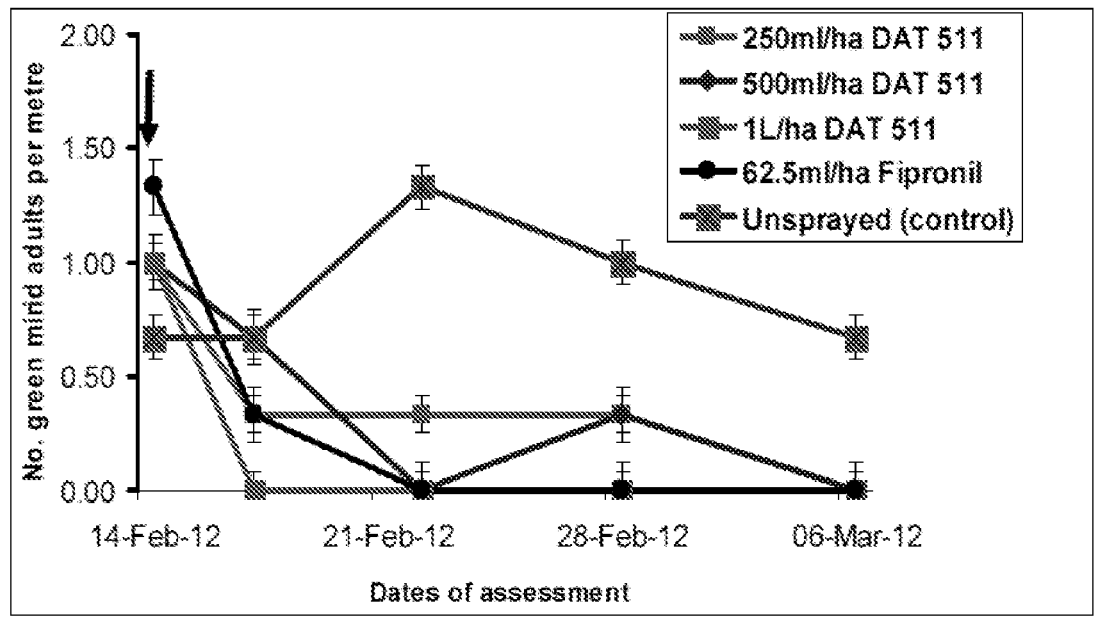
Figure 42B:
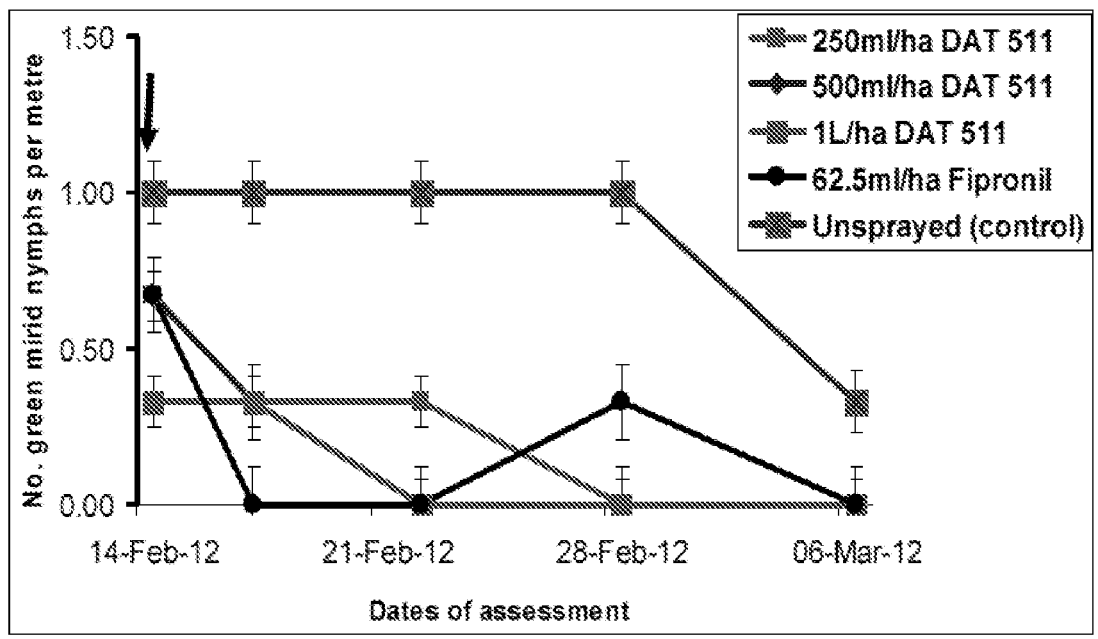

FIG. 42. Efficacy of DAT 511 and conventional insecticides in reducing the number of green mirid adults (A), green mirid nymphs (B) on conventional cotton crops at Undabri in Goondiwindi, during the 2011-2012 season.

Figure 43:
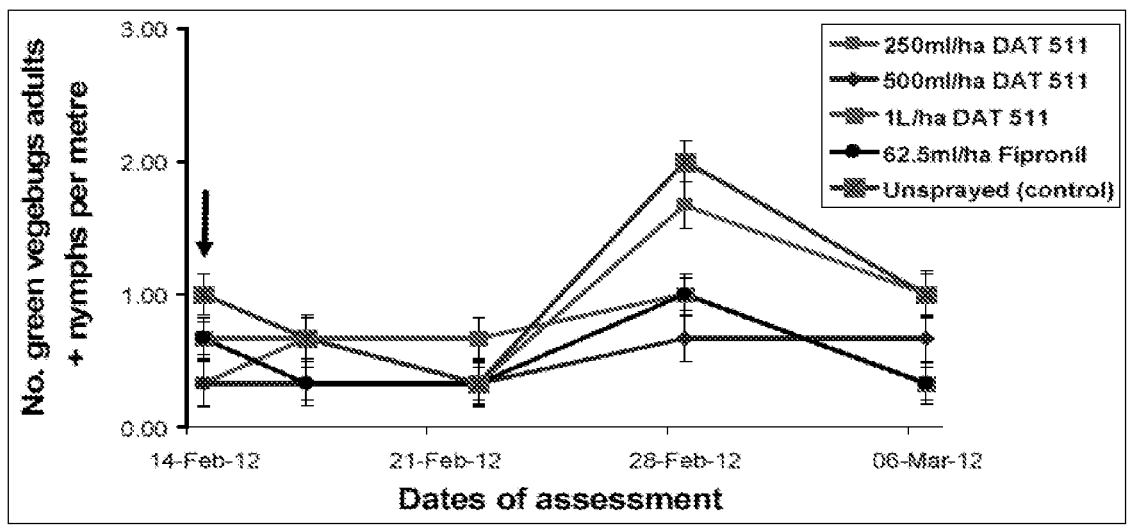

FIG. 43. Efficacy of DAT 511 and conventional insecticides in reducing the number of green vegetable bugs on conventional cotton crops at Undabri in Goondiwindi, during the 2011-2012 season.

Figure 44:
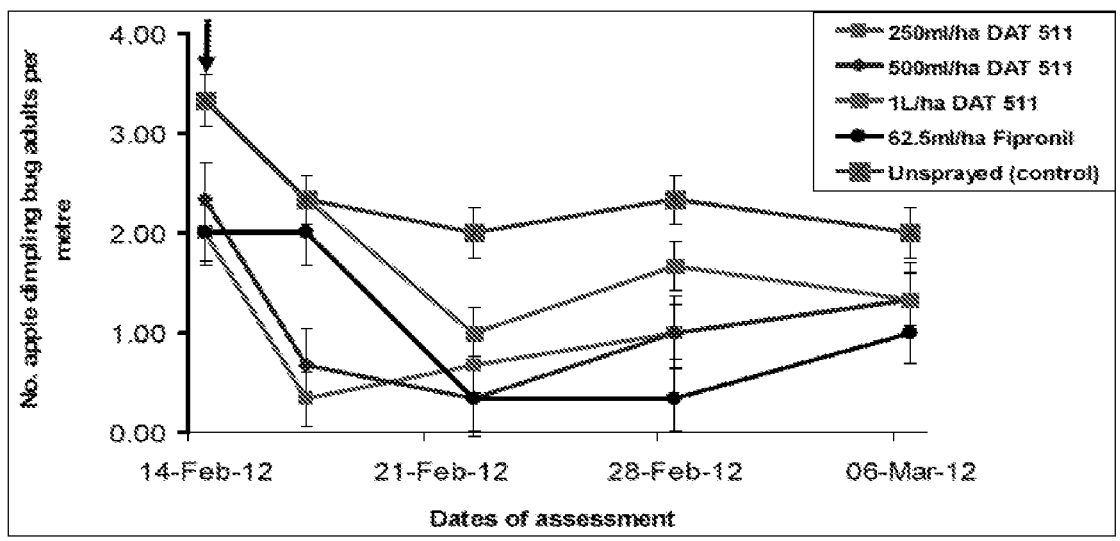

FIG. 44. Efficacy of DAT 511 and conventional insecticides in reducing the number of green vegetable bugs on conventional cotton crops at Undabri in Goondiwindi during the 2011-2012 season.

Figure 45:
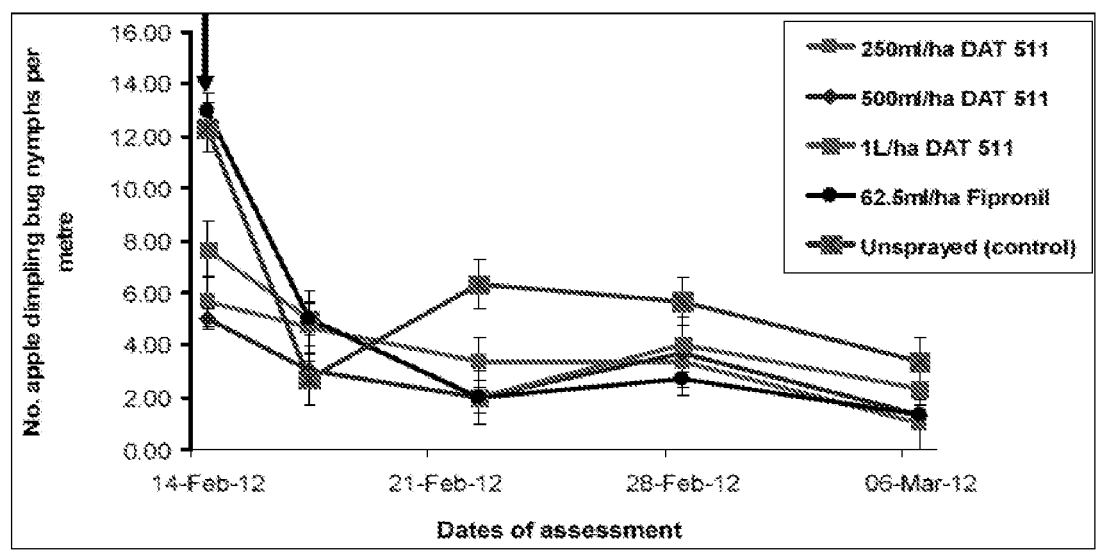

FIG. 45. Efficacy of DAT 511 and conventional insecticides in reducing the number of green vegetable bugs on conventional cotton crops at Undabri in Goondiwindi during the 2011-2012 season.

Figure 46:
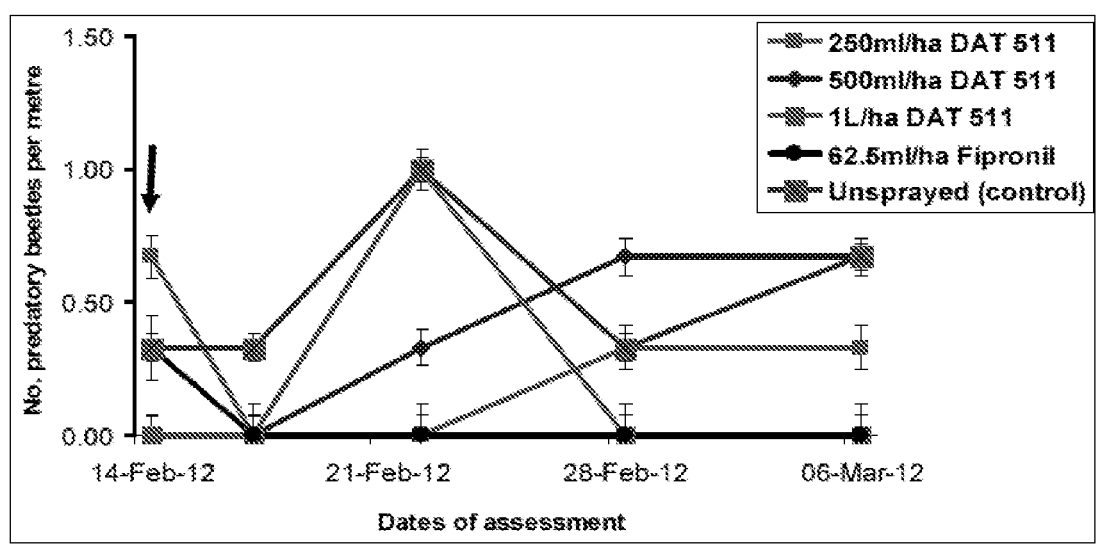

FIG. 46. Efficacy of different rates of DAT 511 in reducing numbers of predatory beetles per metre on conventional cotton crops at Undabri in Goondiwindi during the 2011-2012 season.

Figure 47:
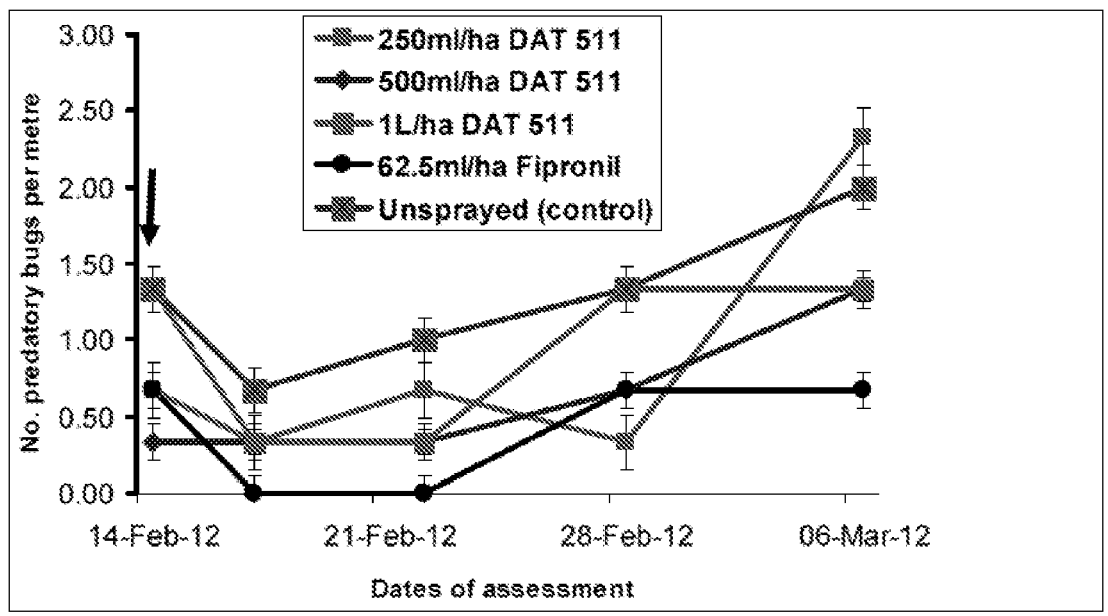

FIG. 47. Efficacy of different rates of DAT 511 in reducing numbers of predatory bugs per metre on conventional cotton crops at Undabri in Goondiwindi during the 2011-2012 season.

Figure 48:
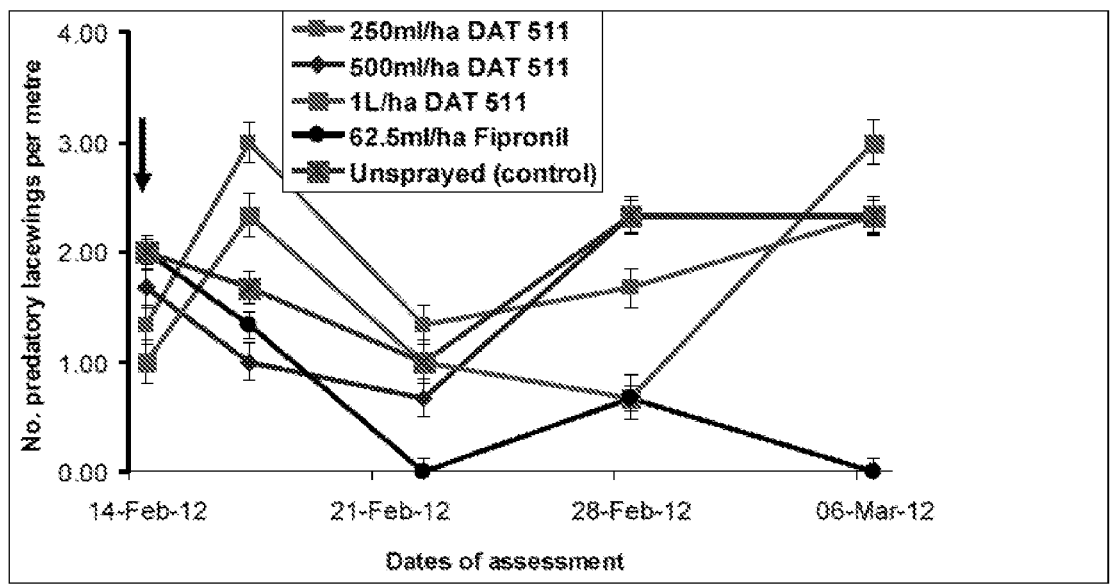

FIG. 48. Efficacy of different rates of application of DAT 511 in reducing numbers of predatory lacewings per metre on conventional cotton crops at Undabri in Goondiwindi during the 2011-2012 season.

Figure 49:
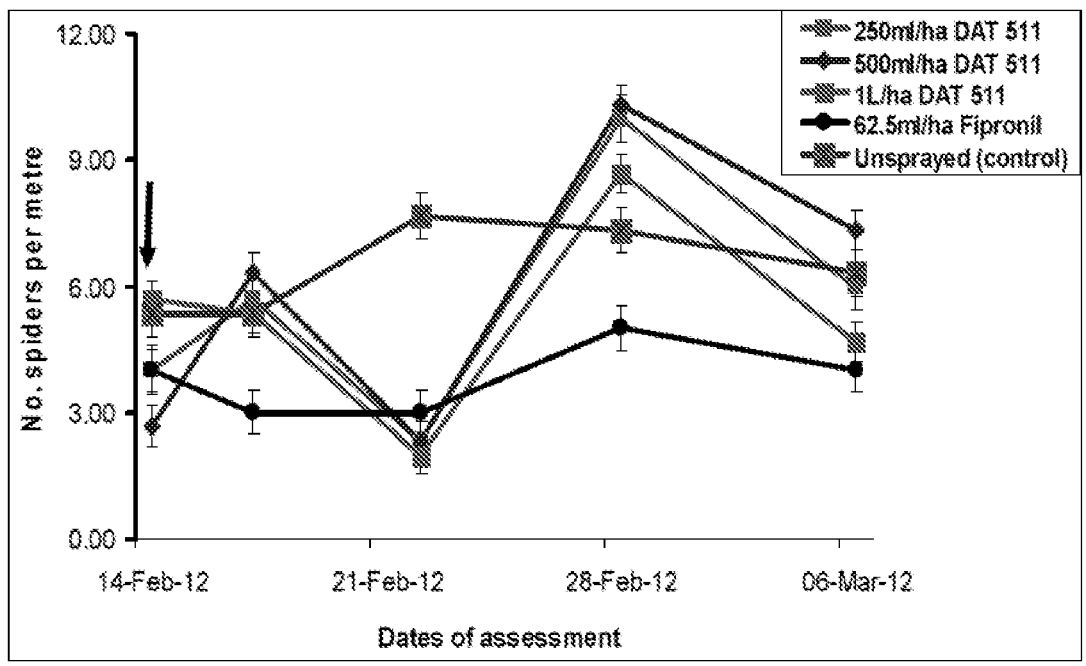

FIG. 49. Efficacy of different rates of DAT 511 in reducing numbers of spiders per metre on conventional cotton crops at Undabri in Goondiwindi during the 2011-2012 season.

Figure 50A:
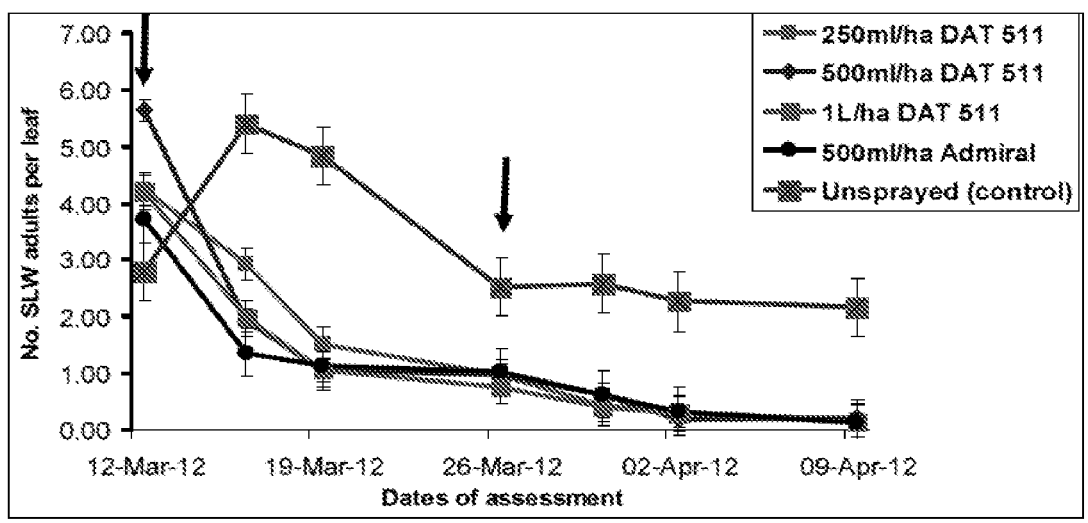
Figure 50B:
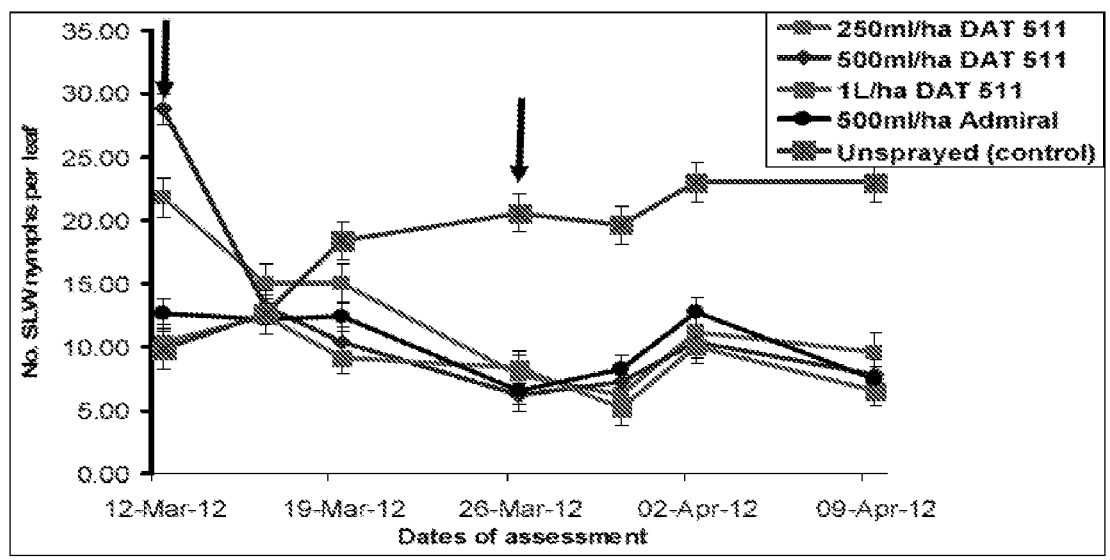

FIG. 50. Efficacy of DAT 511 and conventional insecticides in reducing the number of silverleaf whitefly adults (A) and silverleaf whitefly nymphs (B), on conventional cotton crops at Cooinda, St George, during the 2011-2012 season.

Figure 51A:
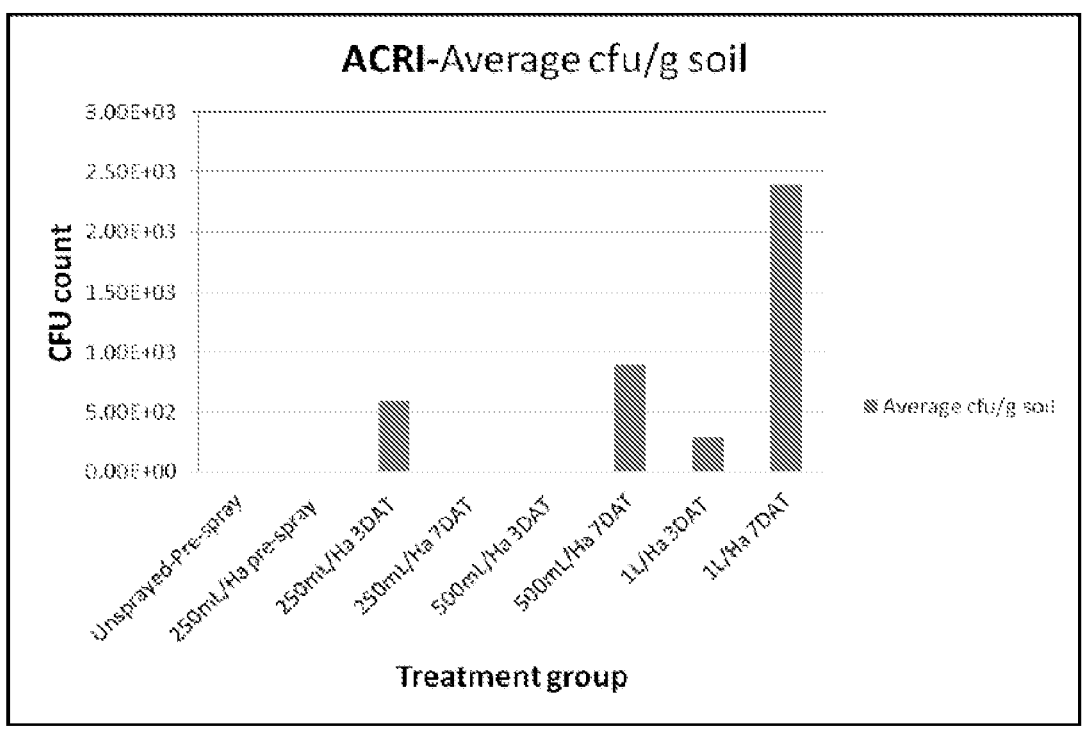
Figure 51B:
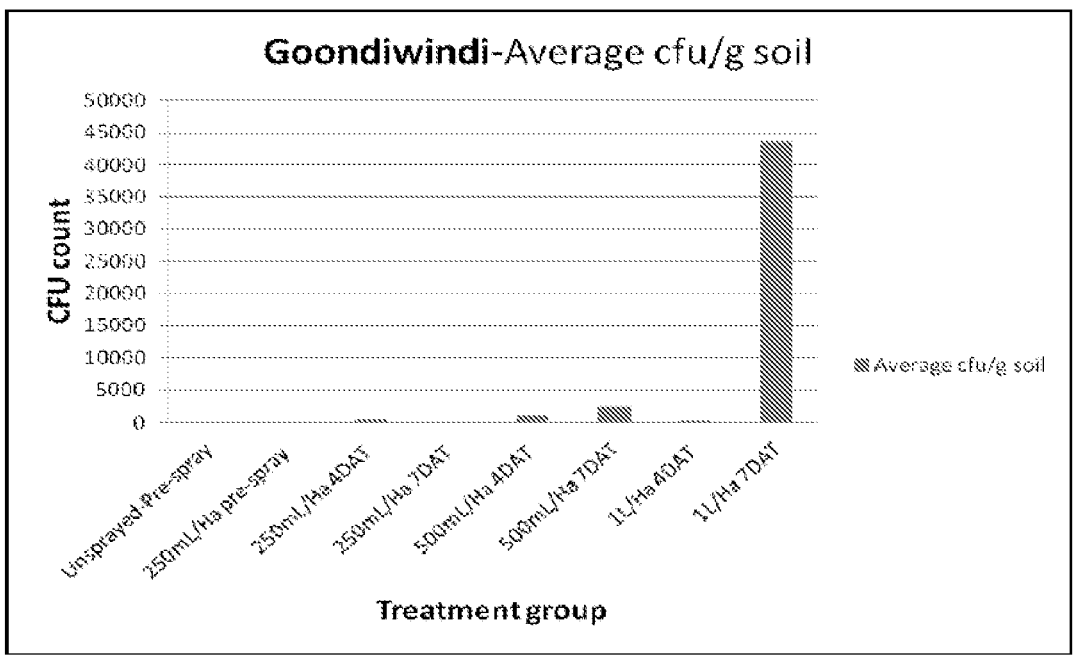

FIG. 51. Soil CFU counts sampled from plots treated with different rates of DAT 511 and unsprayed plots at ACRI in Narrabri (A) and Undabri Goondiwindi (B), during the 2011-2012 season.

Figure 52A:
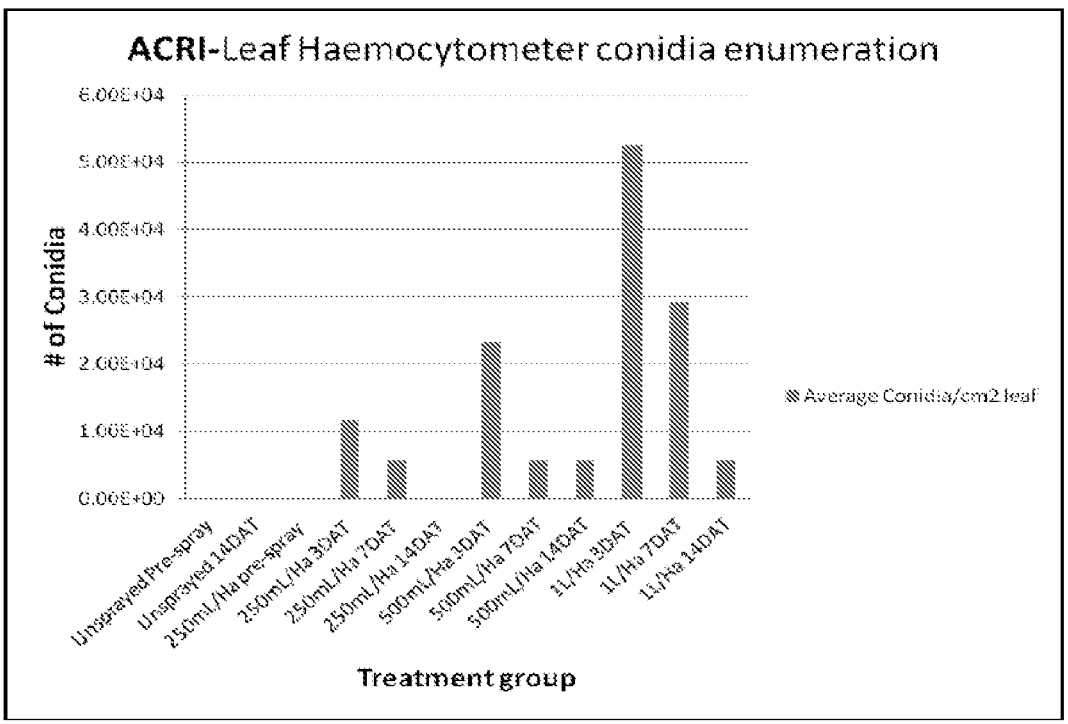
Figure 52B:
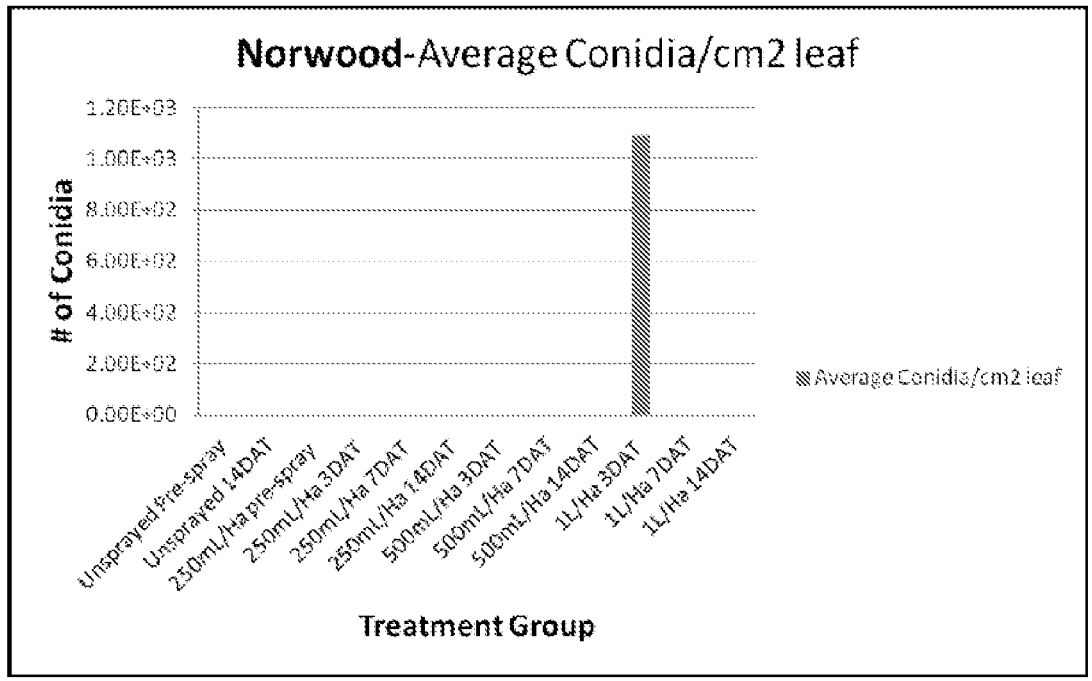
Figure 52C:
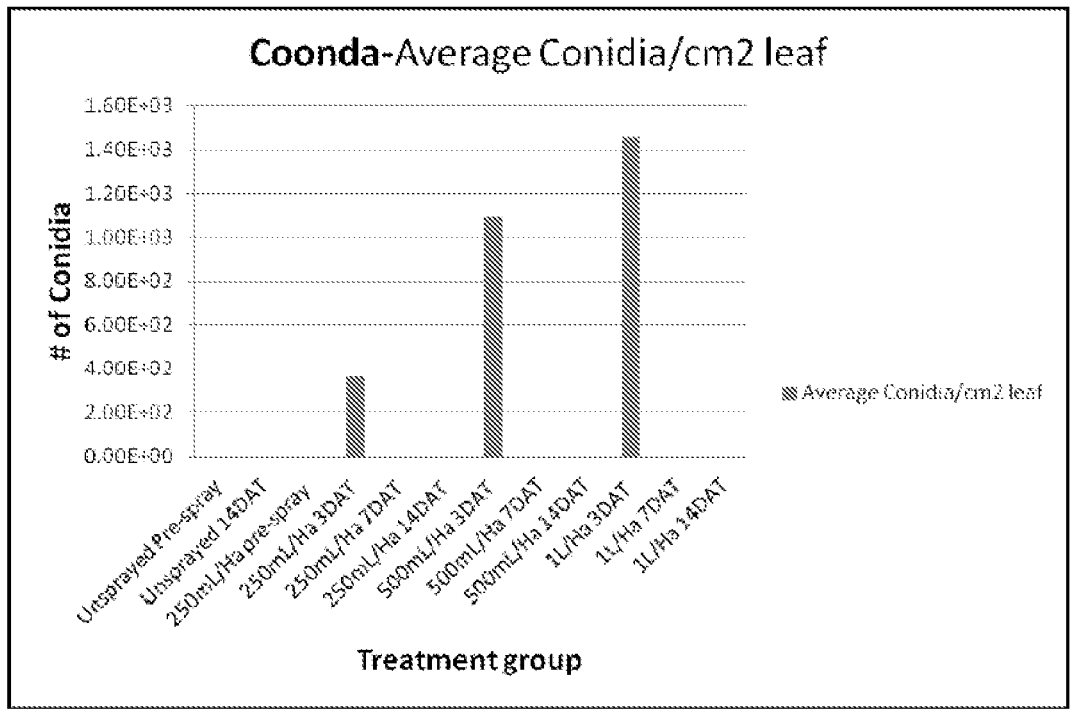

FIG. 52. Leaf haemocytometer conidia enumeration from leaf samples collected from DAT 511 and unsprayed plots at ACRI in Narrabri (A), Norwood in Moree (B), and Coonda in St George (C), during the 2011-2012 season.

Figure 53A:
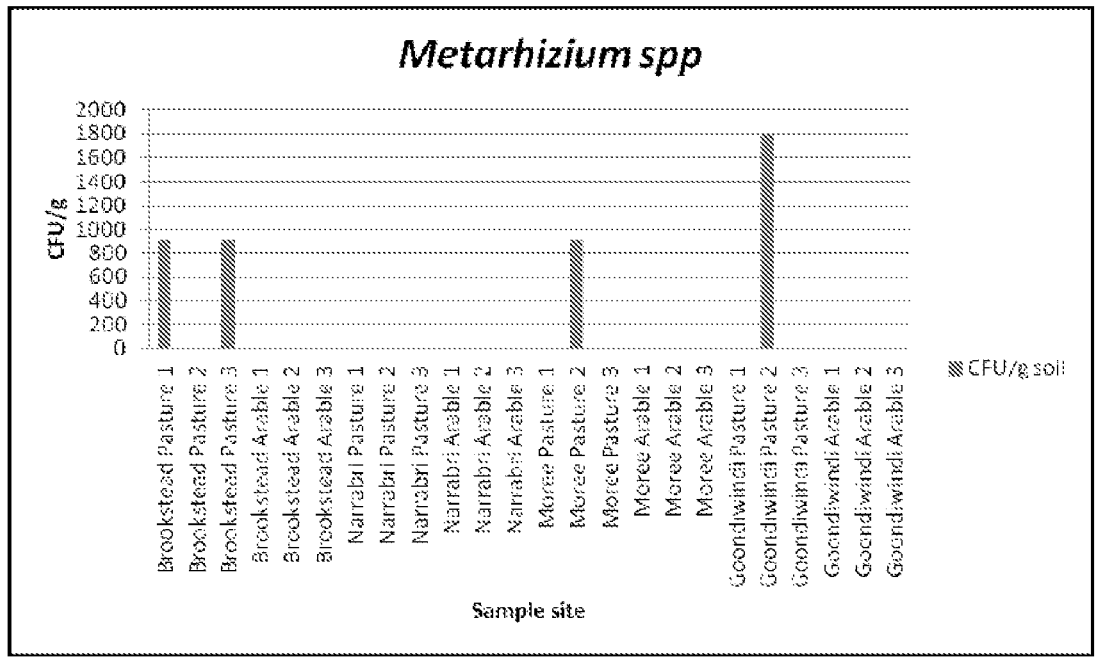
Figure 53B:
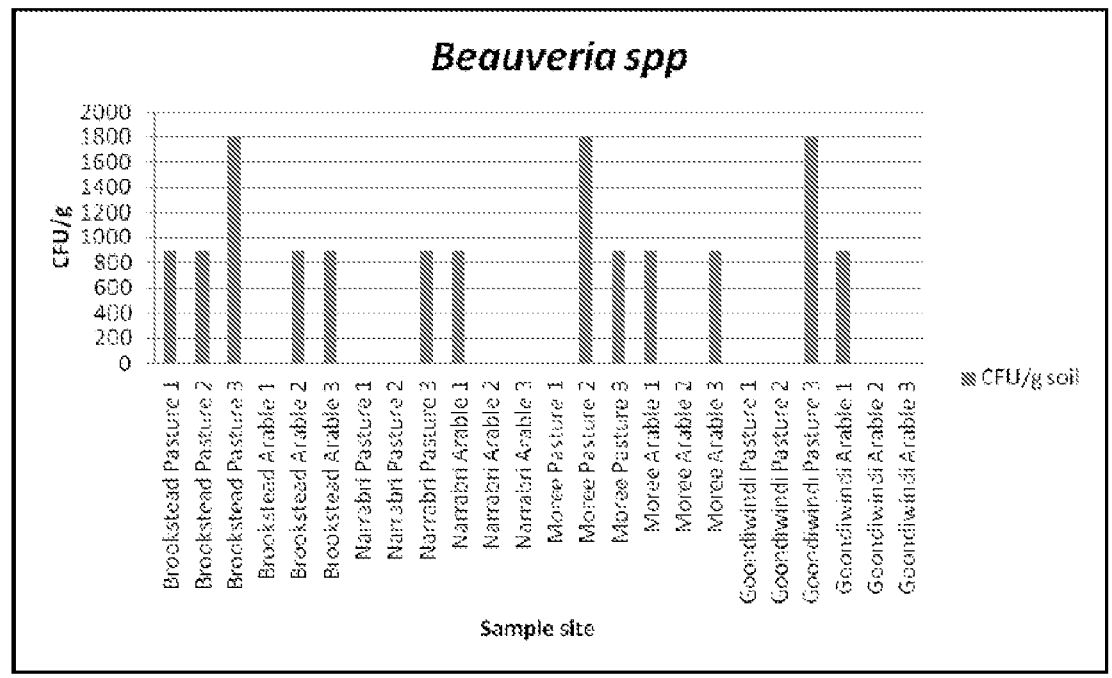

FIG. 53. *Metarhizium* spp. CFUs (A) and *Beauveria* spp. CFUs (B) detected from the various sample sites during the 2011-2012 season.

Figure 54:
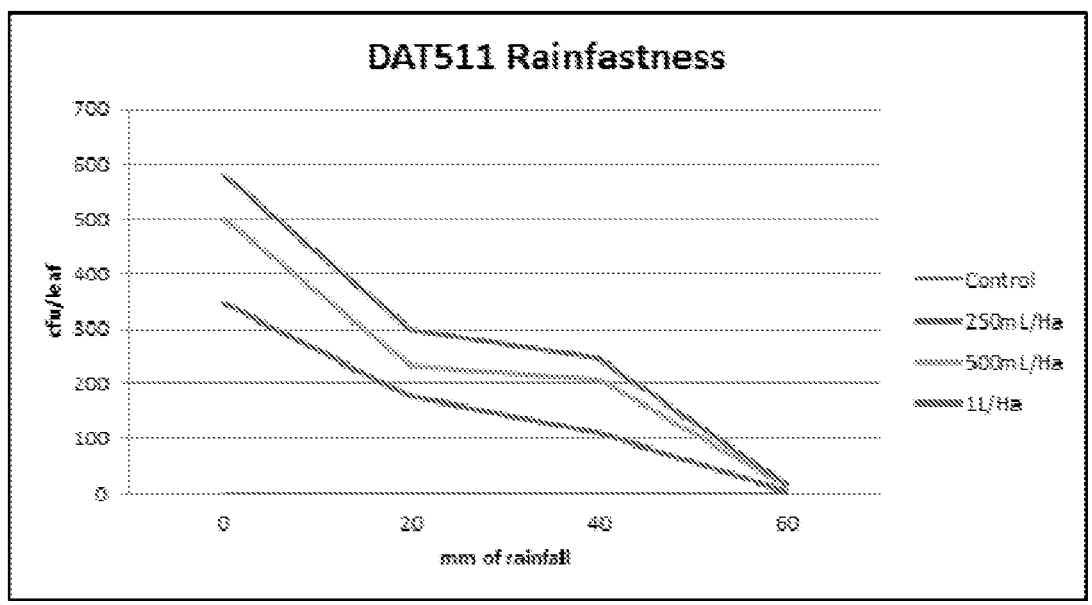

FIG. 54. Effect of rainfall on the persistence of DAT 511 spores on leaves of potted peak squaring cotton plants treated with varying rates of DAT 511 spores at Auscott-Togo, Narrabri, during the 2012-2013 season.

KEY TO THE SEQUENCE LISTING

SEQ ID NO: 1: *Metarhizium* spp. isolate DAT511 deposited under Accession No. V15/001452, 18S ribosomal RNA gene, partial sequence.

DETAILED DESCRIPTION

Micro-organism Deposit Details

The strain of *Metarhiziuim* spp. designated DAT511 was deposited on 14 Jan. 2015 with the National Measurement Institute (NMI) under accession number V15/001452. NMI are located at 1/153, Bertie Street, Port Melbourne, VIC, 3207 Australia. The deposit having the accession number V15/001452 was made by Mark Peacock of BASF Agricultural Specialities, 1205 Old Pacific Highway, Somersby, NSW 2250 Australia. Copies of the deposit certificate and viability statement are annexed hereto.

This deposit was made under the provisions of the Budapest Treaty on the International Recognition of the Deposit of Microorganisms for the Purpose of Patent Procedure and the Regulations thereunder. This assures maintenance of viable cultures for 30 years from the date of deposit. The organism will be made available by the National Measurement Institute under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

General Techniques and Definitions

Unless specifically defined otherwise, all technical and scientific terms used herein shall be taken to have the same meaning as commonly understood by one of ordinary skill in the art (e.g., in plant science, microbiology and molecular genetics).

The term "isolated", as used herein, is intended to mean that the strain or spore of *Metarhizium* spp. of the disclosure has been isolated from its natural source, substrate, habitat or environment and transferred to a culture media e.g., using methods known in the field mycology. For example, an "isolated" strain of *Metarhizium* spp. may encompass fungus or a spore thereof which has been grown or produced in culture. An "isolated" strain of *Metarhizium* spp. also encompasses fungus or spores which have been purified.

The term "spore" is intended to encompass any unicellular or multicellular, reproductive or distributional cells developing into a number of different phases of the complex life cycles of fungi.

As used herein, the term "reproductively viable spores" includes spores (reproductive units of fungus) which, under favourable conditions, will develop into adult fungal organisms.

The terms "controlling" or "control" as used herein are meant to include any pesticidal (killing) or pestistatic (inhibiting, maiming or generally interfering) activities of *Metarhiziuim* spp. against a given invertebrate pest at any stage in its life cycle. Thus, these terms not only include killing, but also include such activities as the production of behavioural abnormalities (e.g., tremor, incoordination, hyperactivity, anorexia) which interfere with such activities such as but not limited to eating, molting, hatching, mobility or plant attachment. Thus, in one embodiment, "controlling an invertebrate pest" may be understood to mean that the fungus kills or interferes with the pest, and includes reducing the number of the pests on a plant or animal compared to the number of pests on the plant or animal prior to application of *Metarhiziuim* spp.

Similarly, the term "protecting" or "protect" as used in the context of plants, plant propagation materials and animals is intended to include any pesticidal (killing) or pestistatic (inhibiting, maiming or generally interfering) activities of the *Metarhiziuim* spp. against a given invertebrate pest at any stage in its life cycle to prevent the invertebrate pest from causing damage, harm, injury or illness to the plant, plant propagation material or animal.

The term "plant" as used herein encompasses not only whole plants, but extends to plant parts, cuttings as well as plant products including roots, leaves, flowers, seeds, stems, callus tissue, nuts and fruit. The term "plant propagation material" is intended to encompass those parts of plant described hereinabove which may be used to propagate, grow or pollinate a plant e.g., seeds, cuttings, flowers, callus tissue, nuts and fruit. Plants that may benefit from the present disclosure cover a broad range of agricultural and horticultural crops, which are described in further detail herein.

As used herein, the term "animal" is intended to encompass any non-human animals, such as livestock animals, working animals, companion animals, sporting animals, laboratory animals and the like, which may be affected by an invertebrate pest. Non-limiting examples of livestock animals include, cattle, pigs, sheep, horses, poultry, goats, deer, donkey, and alpacas. Non-limiting examples of working animals include, horses, dogs, mules, donkey, camelids, oxen and pigs. Non-limiting examples of companion animals include, cats, dogs, reptiles, birds, horses, rodents and rabbits. Non-limiting examples of sporting animals include, horses, cattle and dogs. Non-limiting examples of laboratory animals include, rodents, rabbits, non-human primates, dogs, cats and pigs.

As used herein, the term "soft-bodied insect" is intended to encompass insects or a specific life stage thereof e.g., larvae or pupae, having a soft body i.e., exocuticle is reduced.

*Metarhiziuim* spp.

Entomopathogenic fungi can act as a parasite of insects and/or arachnids and kill or seriously disable them. Entomopathogenic fungi usually attach to the external body surface of insects in the form of microscopic spores (usually asexual, mitosporic spores also called conidia). Under permissive conditions of temperature and moisture, these spores germinate, grow as hyphae and colonize the insect or arachnid's cuticle; eventually they bore through it and reach the body cavity. The fungal cells proliferate in the host body cavity, usually as walled hyphae or in the form of wall-less protoplasts (depending on the fungus involved). After some time the insect or arachnid is usually killed (sometimes by fungal toxins) and new propagules (spores) are formed in/on the insect if environmental conditions are again permissive e.g., if humidity is high enough.

*Metarhizium* is a genus of a entomopathogenic fungi in the Clavicipitaceae family. *Metarhizium* is a mitosporic fungus with asexual reproduction. A number of distinct species of *Metarhizium* are recognised, including *Metarhizium anisopliae, Metarhizium guizhouense, Metarhizium pingshaense, Metarhizium acridum, Metarhizium lepidiotae, Metarhizium majus, Metarhizium globosum, Metarhizium robertsii, Metarhizium brunneum, Metarhizium album, Metarhizium flavoviride,* and *Metarhizium frigidum*. *Metarhizium* spp. are widely distributed, occur naturally in soil and are known to cause disease in variety of insects by acting as a parasitoid. However, most insects living near the soil have evolved natural defenses against entomopathogenic fungi like *Metarhizium*. As a consequence, this genus of fungi is constantly evolving to overcome the defenses of insects. This has led to a large number of different isolates (or strains) of *Metarhizium* which are adapted to certain groups of insects. The present inventors have identified that an isolate of *Metarhizium* spp. comprising a nucleotide sequence having at least 95% identity to a sequence set forth in SEQ ID NO: 1 is particularly effective for controlling invertebrate pests, particularly those invertebrate pests affecting cotton crops or whose habitat or breeding ground is located in an area where cotton is grown.

Accordingly, in one example, the present disclosure provides an isolated strain of *Metarhizium* spp. or a spore thereof comprising a nucleotide sequence having at least 95% identity to the sequence set forth in SEQ ID NO: 1. However, it will be appreciated that % identity figures higher than those provided above will encompass preferred embodiments. Thus, where applicable, in light of the minimum % identity figures, it is preferred that the isolated strain of *Metarhizium* spp. or a spore comprises an nucleotide sequence which is at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the sequence set forth in SEQ ID NO: 1. In a particularly preferred example, the isolated strain of *Metarhizium* spp. or a spore comprises the nucleotide sequence set forth in SEQ ID NO: 1. For example, the present disclosure provides an isolated strain of *Metarhizium* spp. or a spore thereof as deposited under Accession No. V15/001452.

The isolate or strain of *Metarhizium* spp. of the present disclosure may be provided in the form of mature fungus and/or as fungal spores. Preferably, the isolate or strain of *Metarhizium* spp. is provided in the form of spores. Preferably the spores are reproductively viable. In one example, the spores are provided in the form of a dry powder.

Spores of the isolated strain of *Metarhizium* spp. of the present disclosure may be produced by methods known to those skilled in the art. For example, spores of the strain of *Metarhizium* spp. of the present disclosure may be produced using conventional solid substrate and liquid fermentation technologies well known in the art. The spores may be produced in bulk for field application using nutrient film, submerged culture, and rice substrate growing techniques. In this way, the fungi can be grown in sufficient amounts to allow use as agent in compositions and methods of the present disclosure.

One example for producing spores suitable for the present disclosure is as follows. *Metarhizium* spp. spores may be produced by isolating the conidia from infected insects and culturing it on a petri dish plate of dextrose agar. The agar may then be used to inoculate a yeast extract/dextrose broth and which is then incubated on an orbital shaker for 5-6 days at 25° C. The yeast extract/dextrose broth may then be used to inoculate a solid substrate of long grained partially boiled rice that had been sterilized in a 10-1 autoclave self-aerating culture bag. The rice-conidia mixture may then be removed by sieving to give a clean conidial powder which is dried and formulated in oil containing emulsifiers.

Compositions

The fungus or spore of the present disclosure may be formulated into a composition suitable for application to a plant or animal e.g., to protect the plant or animal from insect pests. Accordingly, the present disclosure provides a composition comprising an isolated strain of *Metarhizium* spp. or a spores thereof as described herein.

In one example, the composition is formulated for application to a plant and/or a plant propagation material e.g., seed, and/or soil, and/or a plant pest and/or a habitat of a plant pest.

In one example, the composition is formulated for application to an animal and/or a habitat of a pest to the animal.

For example, compositions of the present disclosure may include the fungus or spore of the disclosure contained in an acceptable diluent, carrier and/or excipient. An acceptable carrier is preferably any material that the plant, plant propagation material, animal, habitat or environment to be treated can tolerate. Thus, when formulated for use with plants, the composition will comprise an effective amount of the fungus or spore of the disclosure and an agriculturally acceptable diluent, carrier and/or excipient suitable for the plant to which the composition is to be applied. Such agriculturally acceptable diluents, carriers and excipients would be known to a person of skill in the art. Alternatively, for use with animals e.g., such as agricultural animals, service animals, companion animals, sporting animals and/or pets, the composition will comprise an effective amount of the fungus or spore of the disclosure and an acceptable diluent, carrier or excipient suitable for use with animals. Diluents, carriers and excipients suitable for use in formulation which are to be applied to, or contacted with, animals would be known to a person of skill in the art.

In a preferred example, the fungus of the disclosure is present in the form of spores.

A composition of the present disclosure may also be achieved by suspending spores of the fungus in an oil, optionally together with an emulsifier. Before application, the oil and optional emulsifier can be mixed with an appropriate quantity of an aqueous medium to form an emulsion before spraying onto the plant and/or plant propagation material and/or soil and/or plant pest and/or habitat.

Thus, in one example, the fungus may be provided in the form of dry powder spores which are formulated in an oil e.g., prior to application. The dry powder spores may be provided alone or together with the oil component. Where the dry powder spores are provided with the oil component, the spores and oil will be packaged separately e.g., in the form of a kit.

In another example, the fungus may be provided in the form of spores suspended in an oil-in-water emulsion.

Preferably, spores will be present in the composition (when formulated as a liquid) at a concentration of at least 10 spores/mL, more preferably at a concentration of at least $1 \times 10^2$ spores/mL, more preferably at a concentration of at least $1 \times 10^3$ spores/mL, more preferably at a concentration of at least $1 \times 10^4$ spores/mL, more preferably at a concentration of at least $1 \times 10^5$ spores/mL, more preferably at a concentration of at least $1 \times 10^6$ spores/mL, and more preferably at a concentration of at least $1 \times 10^7$ spores/mL. In a particularly preferred embodiment, the composition comprises spores at a concentration of at least $1 \times 10^7$ spores/mL.

Liquid compositions of the disclosure may also include water-soluble concentrates, emulsifiable concentrates, emulsions or suspensions.

For example, a typical composition of the present disclosure may comprise 25-50 g dry spore powder formulated in oil, with effective amounts of the formulation dissolved in 30-100 litres of water per hectare of plants to control cotton pests.

Suitable oils for use in a composition of the present disclosure include low molecular weight oil formulations, but other suitable petroleum oils are white oils, DC Tron oil ($nC_{21}$ and $nC_{24}$ oils), Canopy oil ($nC_{27}$ oil), Biopest oil ($nC_{24}$ oils), dormant oil, or summer oil as known in the horticultural industry. Other suitable oils include horticultural oil, olive oil, soy oil, corn oil, sunflower oil, canola oil, linseed oil, castor oil, fish oil, tung oil, sesame oil and/or MCT oils. Most of these oils are $nC_{19}$-$nC_{27}$ but other hydrocarbons having acceptable toxicity may be used. There are number of such products in the market which are suitable for use with the present disclosure. These are Sunspray oil, tea tree oil, Sunspray Ultra fine manufactured by the Sun Refining and Marketing Company.

It will be appreciated that the petroleum spray oil and/or polysaccharide may be used in conjunction with suitable agronomically acceptable diluents, carriers and/or excipients as described herein, as well as with other additives common in the art such as emulsifiers, wetting agents, humectants, surfactants, stabilizers, stickers, spreaders, penetrants or the like.

The compositions of the disclosure may also include so-called 'stressing' additives to improve spore vigor, germination and survivability such as potassium chloride, glycerol, sodium chloride and glucose.

Additives for use in a compositions of the disclosure may also include compositions which assist in maintaining viability of the fungus or spore thereof in long term storage, for example unrefined corn oil and so called invert emulsions containing a mixture of oils and waxes on the outside and water, sodium alginate and conidia on the inside.

Examples of surfactants, spreaders and stickers include Fortune®, carola (capsicums), C-Daxoil®, Codacide Oil®, D-C. Tate®, Supamet Oil, Bond® Penetrant, Citowett®, Fortune Plus™, Fortune Plus Lite, Fruimec, and Fruimec lite. Where selected for inclusion, common agricultural surfactants, such as Tween (available from Rohm & Haas) are desirably included in the composition according to known protocols. It is important that any additives used are present in amounts that do not interfere with the effectiveness of the *Metarhizium* spp. or spore thereof to control invertebrate pests and/or protect plants, plant propagation material or animals from invertebrate pests.

For compositions intended for application to plants, other natural or synthetic, organic or inorganic materials may be included in the composition to facilitate application of the composition to the plant, propagation material thereof, soil, plant pest and/or habitat of the plant pest. Such a carrier is thus generally inert and it should be agriculturally acceptable, in particular on the plant treated. The carrier can be solid (clays, natural or synthetic silicates, silica, resins, waxes, solid fertilizers, etc.) or liquid (water, alcohols, in particular butanol, etc.).

In one example, the composition of the disclosure may be formulated to comprise, or be packaged with, a further substance having insecticidal or pesticidal activity. Suitable substances having insecticidal or pesticidal activity will vary depending on the plant, plant propagation material, animal, insect pest or habitat to which the composition is to be applied. For example, insecticides which may be included in the composition include synthetic insecticides and natural insecticides. Suitable insecticides include endosulfan, dicofol, chlorpyrifos, dimethoate, disulfoton, omethoate, parathion, phorate, profenofos, sulprofos, thiometon, aldicarb, carbaryl, beta-cyfluthrin, deltamethrin, esfenvalerate, fenvalerate, fluvalinate, lamda-cyhalothrin, chlorfluazuron, piperonyl butoxide, petroleum spray oils and the like. Pesticides include biological pesticides. Suitable biological pesticides include *Bacillus thuringiensis*, Nuclear polyhedrosis virus eg ViVus®, Gemstar®, and/or plant extract known to be anti-feedant of pests. Other such substances will be known to a person of skill in the art.

In another embodiment, the composition of the disclosure is provided as a controlled release formulation that is capable of slowly releasing the fungi or spore thereof to its intended target i.e., plant, plant propagation material, soil, animal, insect pest or a habitat of insect pest. As used herein, a controlled release formulation comprises a fungus or spore of the present disclosure in a controlled release vehicle. Such controlled release vehicles suitable for use in a compositions of the present disclosure are known in the art.

Preferably, the composition is a stable composition capable of supporting reproductive viability of the fungi for a period greater than about two weeks, preferably greater than about one month, about two months, about three months, about four months, about five months, more preferably greater than about six months. To be suitable for use in controlling invertebrate pests and/or protecting plants, plant propagation material and/or animals from invertebrate pests e.g., in a method of the disclosure, the composition is preferably able to support reproductive viability of the fungi e.g., such as in the form of spores, for a period greater than about six months. Accordingly, the composition will be formulated to support reproductive viability of the fungi.

Method and Uses

In accordance with the present disclosure, the fungus, spore and/or composition of the present disclosure may be applied to a plant or animal and/or a surrounding of a plant or animal and/or propagation material of a plant and/or a breeding ground or habitat of an insect pest. The term "apply", "applied" "application" or "applying" is intended to cover the act of contacting the fungus, spore or composition either directly or indirectly onto the plant or animal and/or surrounding of the plant or animal and/or propagation material of the plant and/or breeding ground or habitat of the insect pest. Such methods of application will be well known to a person of skill in the art. One exemplary way of applying the fungus, spore or composition of the present disclosure is to formulate the spores in a liquid solution and to spray the solution onto the plant or animal and/or surrounding of the plant or animal and/or propagation material of the plant and/or breeding ground or habitat of the insect pest.

Accordingly, in one example, the present disclosure provides a method for controlling one or more invertebrate pests comprising contacting the invertebrate pest with a fungus, spore or composition of the present disclosure.

In another example, the present disclosure provides a method for protecting a plant, plant propagation material and/or animal from one or more invertebrate pests comprising contacting the plant, plant propagation material, soil or other growth medium surrounding roots of the plant, the animal and/or the habitat or breeding ground of the invertebrate pest, with a fungus, spore or composition of the present disclosure. Preferably, the invertebrate pest(s) is(are) exposed to, or brought in contact with, the fungus, spore or composition.

Exposure of the fungus or spore to the invertebrate pest may be achieved by applying the fungus, spore or composition of the disclosure to a plant, propagation material thereof or to the soil or other growth medium surrounding the roots of the plants or to the seed of the plant before it is sown, or the habitat or breeding ground of the invertebrate pest e.g., using standard agricultural techniques such as spraying. In the case of seeds, the seed(s) may be soaked in or sprayed with the fungus or spore. Alternatively, or in addition, exposure of the fungus or spore to the invertebrate pest may be achieved by applying the fungus, spore or composition of the disclosure directly to an animal affected by, or which interacts with, the invertebrate pest(s) using standard agricultural techniques e.g., such as spraying or drenching. Exposure of the fungus or spore to the invertebrate pest may also be achieved by applying the fungus, spore or composition of the disclosure to an area housing an animal affected by, or which interacts with, the invertebrate pest(s) e.g., applying the fungus, spore or composition to animal sheds, stalls, stables, bedding material and/or paddocks.

The frequency of application of the fungus, spore of composition i.e., frequency of treatment, will vary according to the needs of the plant and/or animal, the environmental conditions under which the plant and/or animal is being grown/reared e.g., including rainfall, humidity and temperature, and the population size or prevalence of the invertebrate pests. Typically the treatment may involve at least two sprays at 14-28 days intervals. Preferably, the treatment may involve at least four sprays at 14-28 days intervals. Repeated applications at the same or different times in a crop or husbandry cycle is also contemplated.

In one example, the method(s) may comprise applying 1-500 g spore powder per hectare of plants. Equally, the method may comprises applying 2-200 g, 5-100 g, 5-80 g, 10-75 g, 10-50, 20-50 g, 25-50 g spore powder per hectare of plants.

In another example, the method(s) may comprise applying 1-5000 ml of oil formulated fungus (including spores) per hectare. Equally, the method may comprise applying 1-1000 ml, 10-1000 ml, 100-1000, 200-800, 400-600, 500 ml of oil formulated fungus (including spores) per hectare. To facilitate application of the oil-formulated fungus (including spores) in accordance with the disclosure, the oil may be added to water prior to application. Accordingly, the method may comprise adding a composition of the disclosure, such as the oil-formulated fungus, to 1-1000 litres of water per hectare. Equally, the method may comprises adding a composition of the disclosure, such as the oil-formulated fungus, to 10-500, 10-200, 10-150, 20-120, 30-100 litres of water per hectare.

Thus, the present disclosure encompasses a method involving applying 50-100, 100-200, 200-800, 400-600, or 500 ml of oil formulated fungal (spores) in 10-150, 20-120 or 30-100, litres of water per hectare. One particular rate of application is 500 ml of oil formulated spores in 30-100 litres of water per hectare.

Preferably, the method of controlling one or more invertebrate pests, and the method of protecting a plant, plant propagation material and/or animal from one or more invertebrate pests, improves crop yield for the plant variety i.e., that would otherwise be affected by the invertebrate pest. The improved crop yield may be determined relative to the yield of a crop of the same plant variety grown under similar conditions which has not received treatment with the fungus, spore or composition of the disclosure.

It will also be understood that the methods, uses and composition of the present disclosure may be used in conjunction with other treatments. Other treatments include the application of insecticides and/or pesticides. Insecticides include synthetic insecticides and natural insecticides. Suitable insecticides include endosulfan, dicofol, chlorpyrifos, dimethoate, disulfoton, omethoate, parathion, phorate, profenofos, sulprofos, thiometon, aldicarb, carbaryl, beta-cyfluthrin, deltamethrin, esfenvalerate, fenvalerate, fluvalinate, lamda-cyhalothrin, chlorfluazuron, piperonyl butoxide, petroleum spray oils and the like. Pesticides include biological pesticides. Suitable biological pesticides include *Bacillus thuringiensis*, Nuclear polyhedrosis virus eg ViVus®, Gemstar®, and/or plant extract known to be antifeedant of pests.

For example, the uses, methods and compositions of the present disclosure may allow for reduced label rates of synthetic chemical treatments and/or biological treatments against relevant invertebrate pests. In one embodiment, the present disclosure allows for half or one-third label rates.

The other treatment can be applied as a mixture or simultaneously or sequentially. For example, for a sequential treatment with a particular treatment regime of the present disclosure, if the regime requires treatment every 14 days or 21 days, then a reduced label rate of another treatment can be applied every alternate fortnight to suppress invertebrate pest numbers if earlier application of the composition of the present disclosure has not brought numbers below the economic threshold. Alternatively, the present disclosure can be applied as a mixture with reduced label rate of another treatment to utilise the synergistic effect of the combination to reduce invertebrate pest numbers below the recommended threshold.

Thus, the present disclosure is suitable for combining with other treatments such as reduced rate of synthetic or biological insecticides to prevent build up populations of invertebrate pests above economic threshold levels or build up resistance by invertebrate pests.

Invertebrate Pests

The fungus, spores, compositions and methods of the present disclosure are useful against one or more invertebrate pests. The term "invertebrate pest" is intended to encompass an invertebrate organism which may be found in, or associated with, a plant or animal and which is detrimental to at least part of said plant or to the animal. Whilst the inventors have demonstrated that the fungus, spores, compositions and methods of the present disclosure are useful against certain species of invertebrate pests, a person of skill in the art will be appreciate that the fungus, spores, compositions and methods are more broadly applicable to other invertebrate pests having similar biology e.g., soft bodied, and/or which interact with agricultural plants and/or animals in a similar manner e.g., sucking and chewing insects.

The fungus, spores, compositions and methods of the present disclosure are also useful against invertebrate pests during one or more stages of the life-cycle e.g., egg, larva, pupae, nymph and/or adult. In this respect, contacting the fungus, spores or compositions of the present disclosure with an invertebrate pest will preferably prevent reproduction, development and/or survival of the invertebrate pest. For example, the fungus, spores, compositions or methods may prevent or reduce eggs of an invertebrate pest from hatching into nymphs or larva. Alternatively, or in addition, the fungus, spores, compositions or methods may prevent or reduce development of nymphs of an invertebrate pest into adult form. Alternatively, or in addition, the fungus, spores, compositions or methods may prevent or reduce the development of larva of an invertebrate pest into pupae form. Alternatively, or in addition, the fungus, spores, compositions or methods may prevent or reduce the emergence of adult forms of an invertebrate pest from pupae. Preferably, contacting of the fungus, spores or compositions of the present disclosure with the invertebrate pest (at any one or more life stages) results in mortality of the invertebrate pest.

Invertebrate Pests of Plants

The fungus, spores, compositions and methods of the present disclosure may be used for the control of a number of invertebrate plant pests. For example, the plant pest may be an insect or arachnid plant pest, and by way of non-limiting example may belong to an order selected from Lepidoptera, Coleoptera, Hemiptera, Thysanoptera, Trombidiformes, Orthoptera and Diptera. In one example, the plant pest is an insect e.g., such as belonging to an order selected from Lepidoptera, Coleoptera, Hemiptera, Thysanoptera, Orthoptera and/or Diptera. In one example, the plant pest is an arachnid e.g., such as belonging to the order Trombidiformes. Non-limiting examples of invertebrate pests that may be controlled, or from which a plant or animal may be protected, using the fungus, spores, compositions and/or methods of the present disclosure include tobacco budworm, native budworm, cotton bollworm including *Helicoverpa armigera, Helicoverpa punctigera, Helicoverpa zea, Heliothis virescens,* diamondback moth (*Plutella xylostella*), *Pectinophora scutigera* (pink spotted bollworm), *Earias* huergeliana (rough bollworm), *Anthonomus grandis* (boll weevil), colorado potato beetle, fall armyworm, southern armyworm, beet armyworm, loopers including cabbage looper, soybean looper, saltmarsh caterpillar, European corn borer, cotton leaf perforator, omnivorous leafroller, citrus peelminer, cotton stainer, cluster caterpillar, cutworms, red shouldered leaf beetle, *Creontiades dilutus* (green mirids), *Nezara viridula* (green vegetable bug), nematodes including cereal cyst nematode (*Heterodera avenae*), root-knot nematode (*Meloidogyne* spp.), root-lesion nematode (*Pratylenchus* spp.), citrus nematode (*Tylenchulus* spp.), dagger nematode (*Xiphinema* spp.), stem nematode (*Ditylenchus dispaci*) and *Anguina agrostis, Agrypnus variabilis* (true wire worm), *Pterohelaeus darlingensis* (Eastern false wire worm), *Gonocephalum macleayi* (southern false wireworm), *Saragus* spp. (false wireworms), *Agrotis* spp. (cutworms), *Smynthurodes betae* (bean root aphids), *Spodoptera exigua* (lesser armyworm), *Epiphyas postvittana* (light brown apple moth), *Thrips tabaci* (tobacco thrip), *Frankliniella schultzi* (tomato thrip), *Frankliniella occidentalis* (western flower thrip), *Chaetocnema* spp. (brown flea beetle), *Nisotra* spp. (redheaded fleabeetle), *Austroasca viridigrisea* (vegetable leafhopper), *Amrasca terraereginae* (cotton leafhopper), *Taylorilygus pallidulus* (brokenbacked bug), *Campylomma liebknechti* (apple dimpling bug), *Crocidosema plebejana* (cotton tipworm), *Bucculatrix gossypii* (cotton leafperforator), *Aphis gossypii* (cotton aphid), *Anomis flava* (cotton looper), *Tetranychus ludeni* (bean spider mite), *Tetranychus lambi* (straweberry spider mite), *Myzus persicae* (green peach aphid), *Trialeurodes vaporariorum* (greenhouse whitefly), *Bemisia tabaci* (silverleaf whitefly) including B type and Q types, *Dysdercus sidae* (cotton stainer), *Tectocoris diophthalmus* (cotton harlequin bug), *Oxycarenus luctuosus* (cotton seed bug), *Spodoptera littura* (cluster caterpillar), *Heliothis zea*, rice stem borer, brown plant hopper, two spotted mites, larval wood moth, a red coffee borer, a larval bag worm or case moth, a caterpillar of *Cryptothelia* or *Pteroma*, a cutworm, an army worm, a Pieridae butterfly, the family Lymantriidae, *Lymantria ninayi, L. rosa, L. novaguinensis, Calliteara queenslandica, Dasychira wandammena*, a looper caterpillar, a Millionaire Moth, from the genus *Milionia* spp, *Alcis papuensis, Paradromulia nigrocellata, Terminalias, Kamarere, Hyposidera talcata, Anthela ekeikei*, from the genus *Anthelidae*, from the genus *Syntherata* spp, a *Thyrididae*, a Limacodidae, a Pyralidae moth *Hypsipyla robusta*, a Hyblaeidae, a diamondback moth (*Plutella xylostella*), fall armyworm, a southern armyworm, a beet armyworm, saltmarsh caterpillar, scales, psyllids, cicadas, treehoppers, planthoppers, *Aphis gossypii* (Cotton aphid), *Austroaqsca viridigrisea* (vegetable leaf hopper), *Amrasca terraereginae* (cotton leaf hopper), *Bemisia tabaci* (silver leaf white flies), and/or *Trialeurodes vaporariorum* (Greenhouse white flies), tarnished and western tarnished plant bug, *Helopeltis* spp., honeylocust plant bug, *Tetranychus urticae* (two-spotted mites), spider mite and their relatives (Tetranychoidea), earth mites (Penthaleidae), thread-footed mites (Tarsonemidae), gall mites, rust mites (Eriophyidae), *Pectinophora gossypiella* (Pink bollworm), *Creontiades pacificus* (Brown mirid), *Dictyotus caenosus* (Brown shield bug), *Halticinae* (Flea beetle), *Plautia affinis* (green stink bug), *Piezodorus hybneri* (Red banded shield bug), *Gonocepphalun macleayi* (False wireworm), *Austroasca viridigrisea* (Green jassid), *Amrasca terraereginae* (brown jassids), *Phenacoccus solenopsis* (Solenopsis mealybugs), *Nomadacris guttulosa* (Spur-throated locust) and *Bactrocera tryoni* (Queensland Fruit fly).

In one example, an invertebrate pest that may be controlled, or from which a plant or animal may be protected, using the fungus, spores, compositions and/or methods of the present disclosure is selected from the group consisting of *Helicoverpa* spp. (e.g., *Helicoverpa armigera* and/or *Helicoverpa punctigera*), mirids (e.g., green mirid and/or brown mirid), wireworm (e.g., true wireworm and/or false wireworm), cutworms, apple dimpling bugs, aphids, green vegetable bug, boll weevil, Rutherglen bug, nematodes, thrips (e.g., Tobacco thrip, Tomato thrip and/or western flower thrip), mites (e.g., two-spotted mite), silverleaf whitefly, bollworm (e.g., pink bollworm, pink spotted bollworm and/or rough bollworm), armyworm (e.g., lesser armyworm), light brown apple moth, cluster caterpillar, cotton looper, cotton tipworm, cotton leaf perforator, broken backed bug, shield bugs (e.g., brown shield bug and/or red banded shield bug), cotton seed bug, flea beetle, stink bugs, jassids (e.g., green jassid and/or brown jassid), mealybugs, locust (e.g., spur-throated locust), fruit fly (e.g., Queensland fruit fly), and pale cotton stainer.

In another example, an invertebrate pest that may be controlled, or from which a plant or animal may be protected, using the fungus, spores, compositions and/or methods of the present disclosure is selected from the group consisting of *Helicoverpa* spp. (e.g., *Helicoverpa armigera* and/or *Helicoverpa punctigera*), mirids (e.g., green mirid and/or brown mirid), wireworm, cutworms, apple dimpling bugs, aphids, green vegetable bug, boll weevil, Rutherglen bug, nematodes, thrips (e.g., Tobacco thrip, Tomato thrip and/or western flower thrip), mites (e.g., two-spotted mite) and/or silverleaf whitefly.

In one example, the invertebrate pest that may be controlled, or from which a plant or animal may be protected, using the fungus, spores, compositions and/or methods of the present disclosure is *Helicoverpa* spp. e.g., *Helicoverpa armigera* or *Helicoverpa punctigera*.

In one example, the invertebrate pest that may be controlled, or from which a plant or animal may be protected, using the fungus, spores, compositions and/or methods of the present disclosure is a mirid e.g., a green mirid or a brown mirid.

In one example, the invertebrate pest that may be controlled, or from which a plant or animal may be protected, using the fungus, spores, compositions and/or methods of the present disclosure is a wireworm e.g., a true wireworm or a false wireworm.

In one example, the invertebrate pest that may be controlled, or from which a plant or animal may be protected, using the fungus, spores, compositions and/or methods of the present disclosure is a cutworm.

In one example, the invertebrate pest that may be controlled, or from which a plant or animal may be protected, using the fungus, spores, compositions and/or methods of the present disclosure is an apple dimpling bug.

In one example, the invertebrate pest that may be controlled, or from which a plant or animal may be protected, using the fungus, spores, compositions and/or methods of the present disclosure is a green vegetable bug.

In one example, the invertebrate pest that may be controlled, or from which a plant or animal may be protected, using the fungus, spores, compositions and/or methods of the present disclosure is a boll weevil.

In one example, the invertebrate pest that may be controlled, or from which a plant or animal may be protected, using the fungus, spores, compositions and/or methods of the present disclosure is a Rutherglen bug.

In one example, the invertebrate pest that may be controlled, or from which a plant or animal may be protected, using the fungus, spores, compositions and/or methods of the present disclosure is a nematode.

In one example, the invertebrate pest that may be controlled, or from which a plant or animal may be protected, using the fungus, spores, compositions and/or methods of the present disclosure is a thrip e.g., a tobacco thrip, a tomato thrip or a western flower thrip.

In one example, the invertebrate pest that may be controlled, or from which a plant or animal may be protected, using the fungus, spores, compositions and/or methods of the present disclosure is a mite e.g., a two-spotted mite.

In one example, the invertebrate pest that may be controlled, or from which a plant or animal may be protected, using the fungus, spores, compositions and/or methods of the present disclosure is a silverleaf whitefly.

In one example, the invertebrate pest that may be controlled, or from which a plant or animal may be protected, using the fungus, spores, compositions and/or methods of the present disclosure is a bollworm e.g., a pink bollworm, a pink spotted bollworm or a rough bollworm.

In one example, the invertebrate pest that may be controlled, or from which a plant or animal may be protected, using the fungus, spores, compositions and/or methods of the present disclosure is an armyworm e.g., a lesser armyworm.

In one example, the invertebrate pest that may be controlled, or from which a plant or animal may be protected, using the fungus, spores, compositions and/or methods of the present disclosure is a light brown apple moth.

In one example, the invertebrate pest that may be controlled, or from which a plant or animal may be protected, using the fungus, spores, compositions and/or methods of the present disclosure is a cluster caterpillar.

In one example, the invertebrate pest that may be controlled, or from which a plant or animal may be protected, using the fungus, spores, compositions and/or methods of the present disclosure is a cotton looper.

In one example, the invertebrate pest that may be controlled, or from which a plant or animal may be protected, using the fungus, spores, compositions and/or methods of the present disclosure is a cotton tipworm.

In one example, the invertebrate pest that may be controlled, or from which a plant or animal may be protected, using the fungus, spores, compositions and/or methods of the present disclosure is a cotton leaf perforator.

In one example, the invertebrate pest that may be controlled, or from which a plant or animal may be protected, using the fungus, spores, compositions and/or methods of the present disclosure is a broken backed bug.

In one example, the invertebrate pest that may be controlled, or from which a plant or animal may be protected, using the fungus, spores, compositions and/or methods of the present disclosure is a shield bug e.g., a brown shield bug or a red banded shield bug.

In one example, the invertebrate pest that may be controlled, or from which a plant or animal may be protected, using the fungus, spores, compositions and/or methods of the present disclosure is a cotton seed bug.

In one example, the invertebrate pest that may be controlled, or from which a plant or animal may be protected, using the fungus, spores, compositions and/or methods of the present disclosure is a flea beetle.

In one example, the invertebrate pest that may be controlled, or from which a plant or animal may be protected, using the fungus, spores, compositions and/or methods of the present disclosure is a stink bug.

In one example, the invertebrate pest that may be controlled, or from which a plant or animal may be protected, using the fungus, spores, compositions and/or methods of the present disclosure is a jassid e.g., a green jassid or a brown jassid.

In one example, the invertebrate pest that may be controlled, or from which a plant or animal may be protected, using the fungus, spores, compositions and/or methods of the present disclosure is a mealybug.

In one example, the invertebrate pest that may be controlled, or from which a plant or animal may be protected, using the fungus, spores, compositions and/or methods of the present disclosure is a locust e.g. a spur-throated locust.

In one example, the invertebrate pest that may be controlled, or from which a plant or animal may be protected, using the fungus, spores, compositions and/or methods of the present disclosure is a fruit fly e.g., Queensland fruit fly.

In one example, the invertebrate pest that may be controlled, or from which a plant or animal may be protected, using the fungus, spores, compositions and/or methods of the present disclosure is a pale cotton stainer.

In one example, the invertebrate pest with which the fungus, spores, compositions and/or methods of the present disclosure are useful is a soft-bodied insect or is at a life stage wherein the exocuticle is reduced e.g., larvae or pupae. For example, a larvae or pupae or any one or more of the invertebrate pests described herein.

Preferred invertebrate pests with which the fungus, spores, compositions and methods of the present disclosure are useful are insect pests of cotton, such as those selected from *Helicoverpa* spp., mirids, wireworm, cutworms, apple dimpling bugs, aphids, green vegetable bug, boll weevil, Rutherglen bug, nematodes, thrips, mites and silverleaf whitefly. In a particularly preferred example, the fungus, spores, compositions and methods of the present disclosure are useful for controlling or protecting plants or plant propagation material against *Helicoverpa* spp., such as by preventing larvae from developing into pupae or preventing emergence of moths from pupae.

As used herein, "plant pest" refers to an invertebrate pest that affects any plant, but in certain embodiments refers to an invertebrate plant pest that affects crop plants, ornamentals or grasses. By way of non-limiting example, the plant pest may be a pest that affects a crop, such as a grain crop or cereal crop including wheat, maize, corn, rice, oats, rye, barley, millet or sorghum, or a plant pest that affects a plant selected from an oil-seed plant, a fruit, a vegetable, a nut, a flower, turf, pasture, a vine, or a legume including soybean pigeon pea, mung bean and chickpea.

For example, the plant pest may be an invertebrate pest that affects an oil-seed plant selected from palm, soybean, rapeseed, castor, sunflower, peanut, cottonseed, palm tree, coconut, olive, corn, hazelnut and other nuts, flax seeds, rice, safflower and sesame.

The plant pest may be an invertebrate pest of a plant that is a crop high in sugar (such as sugar cane, sugar beet, and sweet sorghum) or high in starch (such as corn maize).

Alternatively, plant pest may be an invertebrate pest of a vegetable including leafy and salad vegetables, fruiting and flowering vegetables, fruits of annual or perennial plants, podded vegetables, bulb and stem vegetables, root and tuberous vegetables or sea vegetables. Leafy and salad vegetables include Amaranth, Arugala, Beet greens, Broccoli Rabe, Bitterleaf, Bok choy, Brussels sprout, Cabbage, Catsear, Celery, Celtuce, Ceylon spinach, Chaya, Chard, Chicory, Collard Greens, Chinese Mallow, Chrysanthemum leaves, Corn salad, Cress, Dandelion, Endive, Epazote, Fat hen, Fiddlehead, Fluted pumpkin, Golden samphire, Good King Henry, John Dodd, Kai-lan, Kale, Komatsuna, Kuka, Lagos bologi, Land cress, Lettuce, Lizard's tail, Melokhia, Mizuna greens, Mustard, Napa/Chinese Cabbage, New Zealand Spinach, Orache, Pea sprouts/leaves, Polk, Radicchio, Garden Rocket, Samphire, Sea beet, Seakale, Sierra Leone bologi, Soko, Sorrel, Summer purslane, Swiss chard, Tatsoi, Turnip greens, Watercress, Water spinach, and Winter purslane.

Fruiting and flowering vegetables include fruit trees, Avocado and Breadfruit, and fruits of annual or perennial plants include Acorn squash, Armenian cucumber, Eggplant or Aubergine, Bell pepper, Bitter melon, Caigua, Cape Gooseberry, Capsicum, Cayenne pepper, Chayote, Chili pepper, Cucumber, Luffa, Malabar gourd, Parwal, Tomato, Perennial cucumber, Pumpkin, Pattypan squash, Snake gourd, Squash, Sweetcorn aka corn or maize, Sweet pepper, Tinda, Tomatillo, Winter melon, West Indian gherkin, Zucchini or Courgette.

Flowers or flower buds of perennial or annual plants include Artichoke, Squash blossoms, Broccoli, Cauliflower.

Podded vegetables include American groundnut, Azuki bean, Black-eyed pea, Chickpea, Common bean, Drumstick, Dolichos bean, Fava bean, Green bean, Guar, Horse gram, Indian pea, Lentil, Lima Bean, Moth bean, Mung bean, Okra, Pea, Peanut, Pigeon pea, Ricebean, Rice, Runner bean, Soybean, Tarwi, Tepary bean, Urad bean, Velvet bean, Winged bean, and Yardlong bean.

Bulb and stem vegetables include Asparagus, Cardoon, Celeriac, Celery, Elephant Garlic, Florence fennel, Garlic, Kohlrabi, Kurrat, Leek, Lotus root, Nopal, Onion, Prussian asparagus, Shallot, Welsh onion, and Wild leek.

Root and tuberous vegetables include Arracacha, Bamboo shoot, Beetroot, Black cumin, Burdock, Broadleaf arrowhead, Camas, Canna, Carrot, Cassava, Chinese artichoke, Daikon, Earthnut pea, Elephant Foot yam, Ensete, Ginger, Gobo, Hamburg parsley, Jerusalem artichoke, Jicama, Parsnip, Pignut, Plectranthus, Potato, Prairie turnip, Radish, Rutabaga, Salsify, Scorzonera, Skirret, Sweet Potato or Kumara, Taro, Ti, Tigernut, Turnip, Ulluco, Wasabi, Water chestnut, Yacón and Yam.

Sea vegetables include Aonori, Carola, Dabberlocks or badderlocks, Dulse, Hijiki, Kombu, Mozuku, Laver, Ogonori, Sea grape, Seakale, Sea lettuce and Wakame.

In another example, the plant pest may be an invertebrate pest of fruit, including, for example, Apple and crabapple, Chokeberry, Hawthorn, Loquat, Medlar, Pear, European and Asian species, Quince, Rose hip, the fruitlike base of roses, Rowan, Service tree, Serviceberry or Saskatoon, Shipova, Apricot, Cherry, sweet, black, sour, and wild species, or Berries including Blackberry, boysenberry, olallieberry, and tayberry, Cloudberry, Loganberry, and/or Raspberry.

In further example, the invertebrate pest may be one that affects Arhat, Batuan, Buddha's Hand, Woodapple, Mango, Indian gooseberry, Charichuelo, Cherapu, Coconut, Che, Durian, Gambooge, Goumi, Hardy Kiwi, Kiwifruit or Chinese gooseberry, Mock Strawberry or Indian Strawberry, Garcinia dulcis, Lanzones, Lapsi, Longan Lychee, Mangosteen, Nungu, Peach, Persimmon, Rambutan, Rhubarb, Sageretia, Wild Mangosteen, American chestnut, American Black Elderberry, American grape: North American species, American Hazelnut, American Mayapple, American persimmon, American plum, American Red Elderberry American Red Raspberry, Beach Plum, Black cherry, Black raspberry, Black Walnut, Blueberry, Buffaloberry, Chokecherry, Cocoplum, Cranberry, Eastern May Hawthorn False-mastic, Florida strangler fig, Ground Plum, Huckleberry, Maypop, Muscadine, Pawpaw, Pecan, Prickly pear, Pigeon plum, Red mulberry, Salal berry, Salmonberry, Saskatoonberry, Saw Palmetto, Southern crabapple, Texas persimmon, Thimbleberry, Toyon, Atherton Raspberry, Black Apple, Blue tongue, Bolwarra, Broad-leaf Bramble, Burdekin Plum, Bush tomato, Cedar Bay cherry, Cherry ballart, Cluster fig, Cocky apple, Common apple-berry, Conkerberry, Davidson's plum, Desert banana, Desert fig, Desert lime, Dodder laurel, Doubah, Emu Apple, Emu berry, Fibrous Satinash, Finger Lime, Illawarra Plum, Kakadu lime, Kakadu plum, Karkalla, Kutjera, Lady apple, Lemon aspen, Lillypilly, Little gooseberry tree, Midyim, Morinda citrifolia, Mountain pepper, Muntries, Native currant, Native gooseberry, Native raspberry, Nonda plum, Pigface, Pink-flowered Native Raspberry, Purple apple-berry, Quandong, Queensland Ebony, Riberry, Rose-leaf Bramble, Rose myrtle, Sandpaper Fig, Small-leaf tamarind, Snow berry, Sweet apple-berry, Tanjong, White aspen, Wild grape, Wild orange, Wild peach, Wild plum, Wongi, Yellow plum, Zig Zag Vine, Cardón, Dragonfruit, Prickly pear, Saguaro, Kahikatea, Manoao, Nageia, Podocarpus, Prumnopitys, Rimu, Melons and other members of Cucurbitaceae or Solanaceae family, Gourd, Butternut squash, Cushaw squash, Hubbard squash, Buttercup squash, Pumpkin, Acorn squash, Zucchini, Summer squash, Horned melon, Melon, Raisin tree, Strawberry, cashew apple, Black mulberry, Cornelian cherry, Date palm, Fig, Grape, called raisin, sultana when it is dried, Jujube, Pomegranate, Sycamore fig, Blood Orange, Citron, Clementine, Grapefruit, Hybrids of the preceding species, such as the Orangelo, Tangelo, Rangpur, Kumquat, Lemon, Limes, Key Lime, Persian lime also known as Tahiti lime, Kaffir lime, Mandarin, Naartjie, Orange, of which there are sweet, Pomelo, Sweet Lemon, Tangerine, Carob, Feijoa, Guava, Longan, Lúcuma, Lychee, Passion fruit or Grenadilla, Peanut, Pond-apple Strawberry guava, Tamarillo or Tree Tomato, Ugli, Yangmei, Néré, Abiu, Acerola, Ackee, African cherry orange, Amazon Grape, Araza, Avocado, Acai Babaco, Bacupari, Bael, Banana, Barbadine, Barbados Cherry, Betel Nut, Bilimbi, Bitter gourd, Black sapote, Bottle gourd also known as Calabash, Brazil nut, Breadfruit Burmese grape, or Latka, Calabashtree, CamuCamu, Canistel, Cape gooseberry, Carambola, Cashew, Cempedak or Champedak, Ceylon gooseberry, Chenet, Cherimoya, Chili pepper, Caimito, Cacao, Coffea, Cupuaqu, Custard-apple, Damson plum, Date, Date-plum, Dragonfruit, Durian, Elephant apple, Giant granadilla, Golden Apple, Guarana, Guava, Guavaberry or Rumberry, Hairless Rambutan, Hog plum, Horned melon, Huito, Imbe, Indian almond, Indian fig, Indian gooseberry, Indian jujube, Indian Prune, Jaboticaba, Jackfruit, Jambul, Jatobá, Jocote, also called Jamaica Plum, Kandis, Keppel fruit, Korlan, Kumquat, Kundong, Lablab, Langsat, Lanzones, Lemon, Leucaena, Lime, Longan, Loquat, Lucuma, Lychee, Mabolo, Macadamia, also known as a Queensland nut, Mamey sapote, Mamoncillo, Mandarin, Manila tamarind, Mango, Mangosteen, Marang, Melinjo, Melon pear, Monstera, Morinda, Mountain soursop, Mundu, Mung bean, Muskmelon, Nance, Naranjilla, Lulo, Nutmeg, Neem, Oil Palm, Okra, Papaya, Peach palm, Peanut butter fruit, Pequi or Souari Nut, Pewa, Pigeon pea, Pili nut, Pitomba, Pineapple, Pitomba, Plantain, Poha or Cape Gooseberry, Pois doux, Poisonleaf, Pommecythère or pomcité, Pommerac, Pulasan, Pummelo, Pupunha or peach-palm, Rambutan, Red Mombin, Riberry, Ridged gourd, Salak, Santol, Sapodilla, Sea grape, Soncoya, Soursop, Soybean, Star apple, Strawberry guava, Strawberry pear, Sugar apple, Summer squash, Surinam Cherry, Sweet granadilla, Sweet orange, Sweet pepper, Sweetsop, Rose apple, Tamarind, Vanilla, Wampee, Water apple, Watermelon, Wax apple, Wax gourd, White sapote, or Winged bean.

The plant affected by the invertebrate pest may be a transgenic plant or transgenic crop. Thus, the present disclosure encompasses the use of *Metarhizium* spp. fungus, spore and composition of the disclosure to control invertebrate pests on transgenic plants or crops, such as transgenic cotton. By controlling invertebrate pests on transgenic plants or crops, the present disclosure protects the transgenic plants from damage caused by the invertebrate pests and thereby improves yield from the transgenic plant. One class of plant with which the fungus, spores, compositions and method of the disclosure are useful are transgenic plants/crops or genetically modified plants/crops, including those expressing a transgenic insecticidal protein. Examples of such transgenic plants are cotton, grain crops, maize, sorghum, sunflower, lucerne, potato, various legumes especially soybean, pigeon pea, mung bean and chickpea, tomatoes, vines, rice, fruits, citrus, okra and like plants. In a particularly preferred embodiment, the fungus, spores, compositions and methods of the disclosure are useful for protecting transgenic cotton from invertebrate pests.

The transgenic crops may be genetically modified to include genes which express proteins making it resistant to certain insect pests. The insecticidal protein may belong to the category of *Bacillus thuringiensis* toxins, one example of which is the Cry group. Example proteins include Cry1Ac, Cry2Ab and Cry1F. Another example is the VIP group. These toxins are derived from different strains of a naturally occurring soil micro-organism, *Bacillus thuringiensis* (Bt).

Examples of transgenic crops expressing *Bacillus thuringiensis* toxins include Bt cotton e.g., Bollgard® cotton, Ingard cotton and WideStrike® cotton, Bt canola, Bt tomato, Bt corn, Bt rice and Bt soybean. A further variety of transgenic cotton, VIP cotton, contains a vegetative insecticidal protein gene vip3A, dervived from a common soil bacterium *Bacillus thuringiensis*. The vip3A gene encodes a protein (VIP) that is toxic to the major lepidopteran caterpillar pests of cotton. Accordingly, the fungus of the present disclosure may be used to control pests on Bt transgenic crops which encompasses any modified crop or plant which expresses one or more proteins belonging to the category of *Bacillus thuringiensis* toxins. As used herein "Bt cotton" refers to transgenic cotton expressing one or more *Bacillus thuringiensis* toxins.

Animal Pests

Invertebrate organisms, such as flies, fleas, lice, mosquitoes, gnats, mites, ticks and helminths, are also known to cause tremendous losses to the livestock, service, sporting and companion animal sectors. In particular, invertebrate pests affecting animals, particularly those which are vectors of disease, can have adverse and damaging impacts on agricultural production, market access and human lifestyle. Thus, the fungus, spores, compositions and methods of the present disclosure may be useful for controlling invertebrate pests of animals, thereby preventing and/or reducing physical damage to animals caused by the invertebrate pest and/or preventing or reducing prevalence of disease associated with or caused by the invertebrate pest.

Invertebrate pests of animals with which the fungus, spores, compositions and methods of the present disclosure may be useful include insects and arachnids such as, for example, flies and mosquitoes, mites, ticks, lice, fleas, true bugs, parasitic maggots, and the like.

Adult flies with which the fungus, spores, compositions and methods of the present disclosure may be useful include e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp.

Parasitic fly maggots with which the fungus, spores, compositions and methods of the present disclosure may be useful include, for example, the bot fly (*Oestrus ovis* and *Cuterebra* spp.), the blow fly or *Phaenicia* spp., the screw-worm or *Cochliomyia hominivorax*, the cattle grub or *Hypoderma* spp., the fleeceworm and the *Gastrophilus* of horses.

Mosquitoes with which the fungus, spores, compositions and methods of the present disclosure may be useful include, for example, *Culex* spp., *Anopheles* spp. and *Aedes* spp.

Mites with which the fungus, spores, compositions and methods of the present disclosure may be useful include Mesostigmata spp. e.g., mesostigmatids such as the chicken mite (*Dermanyssus gallinae*), itch or scab mites such as Sarcoptidae spp. e.g., *Sarcoptes scabiei*, mange mites such as *Psoroptidae* spp., including *Chorioptes bovis* and *Psoroptes ovis*, and chigger e.g., *Trombiculidae* spp.

Ticks with which the fungus, spores, compositions and methods of the present disclosure may be useful include soft-bodied ticks e.g., *Argasidae* spp., *Argas* spp. and *Ornithodoros* spp., hard-bodied ticks e.g., *Ixodidae* spp., *Rhipicephalus sanguineus*, *Dermacentor variabilis*, *Dermacentor andersoni*, *Amblyomma americanum*, *Ixodes scapularis* and other *Rhipicephalus* spp.

Lice with which the fungus, spores, compositions and methods of the present disclosure may be useful include *Menopon* spp., *Bovicola* spp., *Haematopinus* spp., *Linognathus* spp. and *Solenopotes* spp.

Fleas with which the fungus, spores, compositions and methods of the present disclosure may be useful include *Ctenocephalides* spp. e.g., dog flea (*Ctenocephalides canis*) and cat flea (*Ctenocephalides felis*), *Xenopsylla* spp. e.g., oriental rat flea (*Xenopsylla cheopis*), and *Pulex* spp. e.g., human flea (*Pulex irritans*).

True bugs with which the fungus, spores, compositions and methods of the present disclosure may be useful include, for example, Cimicidae or the common bed bug (*Cimex lectularius*), Triatominae spp. including triatomid bugs also known as kissing bugs, *Rhodnius prolixus* and *Triatoma* spp.

Accordingly, the fungus, spores, compositions and methods of the present disclosure are effective against different species of agricultural insect pests, at different life stages, affecting a range of agricultural plants and animals, and it will be understood that the insects and plants exemplified and evaluated in the working Examples herein are representative of such a wider variety.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Example 1

Genetic Analysis of Isolated Strains of *Metarhizium*

Molecular characterization of the fungal isolates used in the present study were carried out following PCR amplification of ITS1-5.8s-ITS2 fragment. GenBank searches carried out on the amplified sequence(s) (SEQ ID NO: 1) showed that strain DAT511 is either a strain of *Metarhizium anisopiliae* or *Metarhizium Robertsii*.

Methods

For DNA extraction, conidia were harvested into suspension from the original cultures and used to inoculate two replica potato dextrose agar plates. Each isolate was prepared by spread-plating conidia onto PDA overlaid with colourless cellophane. Plates were incubated at 20° C. for 24-48 hours, until a fine layer of hyphal growth was detected across the surface of the cellophane.

Microcentrifuge tubes were cooled in liquid nitrogen. Small amounts of hyphae were added to the microcentrifuge tubes using a sterile spatula and immediately ground to a fine powder. The microcentrifuge tubes were removed from the liquid nitrogen and DNA was extracted from the ground hyphae using a DNeasy Plant Kit (Qiagen™).

The concentration of the DNA used in the PCR reactions was determined empirically and ranged from 1 to a 10× dilution of the initial isolation. Amplifications of the 18S rRNA fragment was performed in 50 µl volumes containing 2.0 µM of each primer, 1.0 µM dNTPs, 5.0 µl reaction buffer, 3.0 mM $MgCl_2$, 1.0 µl BSA, 4 µl DNA and Taq polymerase (0.25 µl/reaction). Amplification was performed using 30 cycles of 1 min at 94° C., 1 min at 58° C., 2 min at 72° C. Positive and negative controls ($dH_2O$) were included in each PCR run. PCR products were cleaned using an Eppendorf Perfect Prep Gel Cleanup Kit and sequenced directly (The University of Canterbury, Sequencing Facility, New Zealand).

Standard nucleotide BLAST (Basic Local Alignment Search Tool) searches of GenBank database were then performed for the sequence data using the blastn suite available at NCBI.

Results

The Internal transcribed space (ITS), which contains ITS1-5.8s-ITS2, is widely used as the universal fungal barcoding sequence and is useful for molecular systematics at the inter- and intra-species level. The blastn results obtained in this study indicated that the isolated fungus designated DAT511 is a new isolate of *Metarhizium* spp. In this regard, the blastn results indicated that SEQ ID NO: 1 is 99% identical to 18S rRNA sequences for isolates of *Metarhizium anisopiliae* e.g., isolate CNXJY (GenBank Accession FJ589648.1), and is 99% identical to 18S rRNA sequences for strains of *Metarhizium robertsii* e.g., strain A103 (GenBank Accession KC355183.1).

Example 2

Efficacy of *Metarhizium* Isolate DAT 511 Against *Helicoverpa armigera* Pupae on Cotton Plants The aim of the study was to determine the effect of applying fungal isolate DAT 511 to late *Helicoverpa* spp. (5th and 6th instar) larvae on the development and survival of pupae in the soil.

Method

The study was conducted in a mesh cage in the glasshouse. The experimental plants used in all the studies were the conventional (non-transgenic) cotton variety Sicot 71 RRF.

The plants were grown from seeds in pots in the glasshouse and used for the trials when the cotton plants were at squaring stage. The climatic conditions in the glasshouse were 28±2° C. with 60% relative humidity (RH). The treatments were:

1. 0.5% v/v of DAT 511 spores in oil formulation ($1 \times 10^7$ spores/mL) per litre of water; and
2. Control (water only).

Treatment group 1 corresponded to 500 ml of the DAT 511 spores in oil formulation ($1 \times 10^7$ spores/mL) per hectare in the field.

Five squaring cotton plants were randomly allocated to each treatment and replicated 5 times. Ten *Helicoverpa armigera* $5^{th}$ instar larvae reared on an artificial diet in the laboratory were introduced onto the plants (2 larvae per plant) in each treatment replicate. Infested plants and the soil in the pots were sprayed with each treatment using a small hand held pressure sprayer until run-off. The control plants were sprayed with water. All treated plants were transferred into the mesh cage and placed in rows using a complete randomized block design.

Ten days after the larvae moved into the soil, the soil in each treated pot was removed to recover the pupae. Pupae from each treatment were placed individually in petri dishes and moth emergence was recorded.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

The results showed that 80% of larvae treated with 0.5% v/v DAT 511 did not emerge as moths compared with 80% of larvae from the control (water treated) larvae (Table 1).

TABLE 1

Efficacy of fungal isolate DAT 511 against *Helicoverpa armigera* pupae on cotton plants in the glasshouse.

| Treatment | Moth emergence from pupae (%) |
|---|---|
| Water | 80 |
| 0.5% v/v DAT 511 | 20 |

The outcome of this study demonstrates that entomopathogenic fungus DAT 511 may be useful as a last spray on Bt cotton crops against *Helicoverpa* spp. 5-6th instar to prevent pupae developing from the larvae in the soil.

Example 3

Efficacy of *Metarhizium* Isolate DAT 511 Against *Helicoverpa armigera* Pupae on Cotton Plants Following the results from the study detailed in Example 2, a further study was conducted to determine the effect of applying fungal isolate DAT 511 to late *Helicoverpa* spp. (5th and 6th instar) larvae on the development and survival of pupae in the soil.

Method

A similar methodology to that outlined in Example 2 was used, with the exception that 16 cotton plants per treatment were used in this study. Thirty-two *Helicoverpa armigera* 5th instar larvae reared on an artificial diet in the laboratory were used to infest each treated plant (2 larvae per plant). The infested plants and the soil in the pots were treated with the following:
1. 0.75% v/v of DAT 511 spores in oil formulation ($1 \times 10^7$ spores/mL oil) per litre of water
2. Water only (control).

Treatment group 1 corresponded to 750 ml of the DAT 511 spores in oil formulation ($1 \times 10^7$ spores/mL) per hectare in the field.

A hand held pressure sprayer was used to apply each treatment to the infested plants. Sprays were applied until run-off. The control plants were sprayed with water. All treated plants were transferred into the mesh cage and placed in rows using a complete randomized block design.

Ten days after the larvae moved into the soil, the soil in each treated pot was removed to recover the pupae. Pupae from each treatment were placed individually in plastic bottles and moth emergence was recorded daily.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Pupal Emergence

It was observed that some of the larvae treated with the fungal isolate could not turn into full blown pupae because the fungus killed the larvae prior to turning into pupae (half larvae and half pupae). The larvae that did turn into pupae were then killed by the growing fungus so no adult moths emerged from these pupae (FIG. 1). The total number of *H. armigera* pupae that emerged from larvae treated with 0.75% v/v DAT 511 were significantly lower than larvae sprayed water (control) treatment (FIGS. 2 and 3).

Pupal Mortality

The study showed that 21.9-34.4% of *Helicoverpa* spp. late stage larvae treated with 0.75% v/v DAT 511 died before they could pupate and 53.1-62.5% of pupae did not emerge (FIG. 2). Overall, application of 0.75% v/v DAT 511 caused 84.4% mortality when the treatments were applied to 5th instar *H. armigera* on cotton plants (FIG. 2). Interestingly, all moths emerged from pupae whose larval stage were treated with water (FIG. 3).

Example 4

Efficacy of Coating Cotton Seeds with *Metarhizium* Isolates DAT 511 on Wireworms, Cutworms and Other Soil Inhabiting Insects Most spores of entomopathogenic fungi can remain dormant in the soil during unfavourable conditions and become viable when the inoculums come into contact with a suitable host e.g. insects. Soil dwelling insects are also known to disperse fungal spores which can infect and kill these insects in the soil. The aim of this study was to determine the effect of coating cotton seeds with spores of entomopathogenic fungi (DAT 511) on densities of soil pests such as wireworms, seedling stage thrips, cotton seed germination and plant stand. A first trial was carried out on a commercial cotton farm at Spring Ridge and a second trail was carried out on a commercial cotton field at Norwood, NSW (near Moree).

Spring Ridge Trial

Method

The treatments evaluated were:

1. 50 g spores/ha DAT 511 ($1.0\times10^7$ spores/mL); and
2. Cruiser X (600 g/L Thiamethoxam).

The trial assessed:

densities of wireworms (true and false wireworms); and densities of seedling thrips.

Fungal spores have no systemic properties like synthetic insecticides such as Cruiser X. Accordingly, one application of DAT511 was made to the fungus treated plots and densities of seedling aphids and thrips were assessed if these insects become a problem at the study site. The heavy and consistent rainfall at the study site prevented any DAT 511 fungus being applied to the cotton crop after seedling emergence.

Development of Pitfall Traps and Assessment of Wireworms

Visual sampling and pitfall traps were used to assess the trials. Forty grams of pre-soaked sorghum seed (*Sorghum bicolor*) was placed in plastic pipe of 5 cm diameter and 5 cm length with 10 vent holes (1.0 cm in diameter) on the sides. This was placed in 5 cm deep holes in a cotton field and covered with soil (calculated 1 cm of loose soil). In each treatment, groups of 4 baits were placed in a 5 m by 5 m square grid pattern from 17 Oct. 2011 until 11 Nov. 2011 (cotyledon to 6 true-leaf stage) following the methodology of Murray and Wicks (1986) and Robertson and Simpson (1989).

The baits were excavated 7 days after placement when the cotton shoots had emerged from the soil. The sorghum seedlings in the traps emerged 4 days after placement. The soil, sorghum seeds in the plastic pipe and a small amount of the surrounding soil in the holes (calculated 0.5 L of material) were emptied and hand sorted on a metal tray to recover insects. The number of each wireworm species were identified and recorded. The number of true and false wireworms was expressed as numbers per trap per treatment.

Assessment of Densities of Thrips

The sampling of thrips adults and nymphs were done on whole plants. Six seedlings from each replicated treatment (24 seedlings per treatment) were removed and quickly transferred to separate plastic bags and taken into the laboratory where they were washed with alcohol into a petri dish and counted. Sampling was done every 3 days from 24 Oct. 2011 until 11 Nov. 2011. Data was expressed as number of thrips adults and nymphs per treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Density of Wireworms

Wireworms (*Agrypnus* spp.) were sampled from the treated plots from 24 Oct. 2011 until 11 Nov. 2011 (Table 2). The number of wireworm adults and nymphs recorded in plots sown with seeds coated with DAT 511 were not significantly different ($P>0.05$) from plots sown with seeds treated with Cruiser X at 3 DAT. However, they were significantly different ($P<0.01$, $P<0.03$ and $P<0.01$ respectively) at 7 DAT (Table 2). At 10, 14 and 18 DAT, the Cruiser X treated plots had the same number of wireworms per trap as the DAT 511 treated plots (Table 2).

TABLE 2

Densities of wireworms per trap in soil where cotton seeds were treated with entomopathogenic fungi (DAT 511) and synthetic insecticide (Cruiser X) at Spring Ridge, NSW, 2011.

| Treatments | Pre-treatment 24 Oct. 2011 | 3 DAT | 7 DAT | 10 DAT | 14 DAT | 18 DAT |
|---|---|---|---|---|---|---|
| | Number of wireworms (adults + nymphs) per trap | | | | | |
| 50 g spores/ha DAT 511 | 12.00 ± 1.59a | 7.75 ± 1.61a | 3.88 ± 0.81a | 2.00 ± 0.33ab | 2.88 ± 0.61ab | 0.75 ± 0.16ab |
| 600 g/L Thiamethoxam (Cruiser X) | 12.00 ± 1.60a | 4.50 ± 0.91a | 1.38 ± 0.26b | 0.88 ± 0.52b | 1.38 ± 0.42b | 0.38 ± 0.18b |
| | $P = 0.386$ | $P = 0.177$ | $P < 0.001$ | $P < 0.01$ | $P < 0.03$ | $P < 0.01$ |

Means between treatments followed by the same letter are not significantly different ($P < 0.05$), Tukey-Kramer multiple comparison test.
DAT = Days after treatment.

Density of Thrips

The number of thrips per plant (FIG. 4; Table 3) and thrips damage (FIG. 5) recorded on plots treated with DAT 511 and Cruiser X were not significantly different to each other ($P>0.05$).

Assessment of Thrip Densities

The sampling of thrips adults and nymphs was done on whole plants. Six seedlings from each replicated treatment (24 seedlings per treatment) were removed and quickly transferred to separate plastic bags. The bags were taken into

TABLE 3

Density of thrips per plant from cotton seed treated with entomopathogenic fungi (DAT 511) and synthetic insecticide (Cruiser X) at Spring Ridge, NSW, 2011.

| Treatments | Pre-treatment | 3 DAT | 7 DAT | 10 DAT | 14 DAT | 18 DAT |
|---|---|---|---|---|---|---|
| | Number of thrips (adults + nymphs) per plant | | | | | |
| 50 g spores/ha DAT 511 | 18.13 ± 1.27a | 8.50 ± 0.76a | 23.63 ± 3.16a | 8.13 ± 2.16a | 35.25 ± 9.45a | 102.62 ± 23.20a |
| 600 g/L Thiamethoxam (Cruiser X) | 15.13 ± 1.84ab | 6.00 ± 0.85a | 20.75 ± 3.99a | 6.38 ± 1.69a | 45.38 ± 12.4a | 112.38 ± 21.9a |
| | $P < 0.01$ | $P = 0.136$ | $P = 0.667$ | $P = 0.386$ | $P = 0.273$ | $P = 0.905$ |

Means between treatments followed by the same letter are not significantly different ($P < 0.05$), Tukey-Kramer multiple comparison test.

Norwood Trial
Method
The treatments evaluated were:
1. 50 g spores/ha DAT 511 (1.0×10$^7$ spores/mL)
2. 1.0 L/ha Plant X (Sero-X®)
3 2.0 L/ha Plant X (Sero-X®)
4. 2.0 L/ha GreenFire®)
5. Cruiser X (600 g/L Thiamethoxam)
6. Untreated seed (control).
The trial assessed:
plant stand after germination (seed rate approximately 7.5 plants/m$^2$);
densities of wireworms (true and false wireworms); and
densities of seedling thrips.
Assessment of Wireworm Densities
Visual sampling of pitfall traps was used to assess densities of wireworms. Forty grams of pre-soaked sorghum seed (*Sorghum bicolor*) was placed in plastic pipe of diameter 5 cm and length 5 cm with 10 vent holes (1.0 cm in diameter) on the sides. This was placed in 5 cm deep holes in a cotton field and covered with 1 cm of loose soil. In each treatment, groups of 4 baits were placed in a 5 by 5 m square grid pattern from 8 Oct. 2011 until 17 Nov. 2011.

The baits were excavated 4 days after placement. The soil, sorghum seeds in the plastic pipe and surrounding soil in the holes were emptied and hand sorted on a metal tray to count the insects. Each wireworm species was identified and recorded for each treatment in the field. Densities of true and false wireworms were expressed as number per trap per treatment.

the laboratory, washed with alcohol onto a petri dish and counted. Sampling was done every 4 days from 8 Nov. 2012 until 14 Dec. 2012. Data was expressed as number of thrips adults and nymphs per treatment.
Analysis of the Data
All experimental data were analysed using repeated measures ANOVA (Graphpad Instat and Prism Software, Inc. v. 2.03, San Diego, Calif., USA). Treatment and sample dates were the independent variables. Tukey-Kramer multiple comparison tests were used to separate means.
Results
Density of Wireworms
Wireworms (*Agrypnus* spp.) were sampled from the treated plots from 24 Oct. 2011 until 11 Nov. 2011 (Table 2). The number of wireworm adults and nymphs recorded in plots sown with seeds coated with DAT 511 were not significantly different ($P>0.05$) from plots sown with seeds treated with Cruiser X at 3 DAT. However, they were significantly different ($P<0.01$, $P<0.03$ and $P<0.01$ respectively) at 7 DAT (Table 2). At 10, 14 and 18 DAT, the Cruiser X treated plots had the same number of wireworms per trap as the DAT 511 treated plots (Table 2).
Thrip Densities
The species of thrips abundant in the study site were predominantly *Thrips tabaci*. The number of thrips adults and nymphs per plant recorded in plots treated with the fungal biopesticides (DAT 511), semiochemicals (Plant X and GreenFire) and synthetic insecticides (Cruiser X) were not significantly different ($P>0.05$) (Tables 4 and 5).

There was no significant difference (P>0.05) in yield (bales per acre) between the entomopathogenic fungi (DAT 511), semiochemical (Plant X and GreenFire) and synthetic insecticide (Cruiser X) treated plots (Table 6).

by wireworms and the number of thrips per plant on plots treated with fungi (DAT 511) and 1 L/ha Plant X were not significantly different (P>0.05) from the Cruiser X treated plots.

TABLE 4

Densities of *Thrips tabaci* adults on cotton plants where the cotton seeds were coated with entomopathogenic fungi (DAT 511), semiochemicals (Green Fire and Plant X) and synthetic insecticide (Cruiser X) at Norwood, NSW, 2012.

| Treatments | Pre-treatment counts | 4 DAT | 10 DAT | 14 DAT | 21 DAT |
|---|---|---|---|---|---|
| 500 ml/ha DAT 511 | 14.25 ± 2.72a | 13.50 ± 3.28a | 21.75 ± 5.96a | 18.75 ± 8.13a | 3.50 ± 1.19a |
| 2 L/ha GreenFire | 10.50 ± 3.80a | 6.00 ± 1.47a | 26.5 ± 6.61a | 22.00 ± 7.70a | 2.00 ± 0.41a |
| 2 L/ha Plant X | 9.75 ± 0.85a | 6.00 ± 1.35a | 23.00 ± 5.58a | 30.50 ± 8.47a | 4.00 ± 1.47a |
| 1 L/ha Plant X | 13.50 ± 2.63a | 7.50 ± 2.72a | 26.25 ± 6.09a | 33.50 ± 13.5a | 3.75 ± 1.11a |
| Thiamethoxam (Cruiser X) 600 g/L | 15.75 ± 1.44a | 8.25 ± 3.90a | 19.00 ± 1.47a | 30.50 ± 7.84a | 4.75 ± 1.93a |
| Untreated (control) | 13.25 ± 1.32a | 8.25 ± 2.56a | 24.50 ± 5.97a | 34.50 ± 16.28a | 5.50 ± 2.22a |
| Significant difference | P > 0.47 | P > 0.43 | P > 0.21 | P > 0.59 | P > 0.37 |

Number of *Thrips tabaci* adults per plant

Means within columns followed by the same letters are not significantly different (P > 0.05), Tukey-Kramer Multiple comparison test.
DAT = Days after treatment.

TABLE 5

Densities of *Thrips tabaci* adults on cotton plants where the cotton seeds were coated with entomopathogenic fungi (DAT 511), semiochemicals (Green Fire and Plant X) and synthetic insecticide (Cruiser X) at Norwood, near Moree, NSW, 2012.

| Treatments | Pre-treatment counts | 4 DAT | 10 DAT | 14 DAT | 21 DAT |
|---|---|---|---|---|---|
| 500 ml/ha DAT 511 | 57.50 ± 26.72a | 37.50 ± 9.79a | 82.00 ± 12.43a | 49.25 ± 8.13.17a | 30.75 ± 7.86a |
| 2 L/ha GreenFire | 34.00 ± 15.69a | 19.00 ± 3.81a | 55.00 ± 10.51a | 53.00 ± 25.42a | 24.75 ± 2.66a |
| 2 L/ha Plant X | 30.50 ± 1.66a | 35.00 ± 9.68a | 56.75 ± 10.84a | 46.00 ± 13.12a | 21.75 ± 4.33a |
| 1 L/ha Plant X | 39.75 ± 7.66a | 35.75 ± 5.28a | 63.50 ± 10.15a | 37.00 ± 8.29a | 23.00 ± 6.57a |
| Thiamethoxam (Cruiser X) 600 g/L | 34.00 ± 7.63a | 29.75 ± 4.09a | 41.25 ± 7.94a | 46.25 ± 8.71a | 28.25 ± 5.22a |
| Untreated (control) | 48.00 ± 7.74a | 26.75 ± 6.52a | 49.00 ± 17.66a | 56.50 ± 15.81a | 29.75 ± 9.09a |
| Significant difference | P > 0.71 | P > 0.19 | P > 0.23 | P > 0.90 | P > 0.77 |

Number of *Thrips tabaci* nymphs per plant

Means within columns followed by the same letters are not significantly different (P > 0.05), Tukey-Kramer Multiple comparison test.
DAT = Days after treatment

TABLE 6

Cotton yield harvested from plants from seeds coated with fungal biopesticides (DAT 511), semiochemicals (Green Fire and Plant X) and synthetic insecticide (Cruiser X) at Norwood, near Moree, NSW, 2012.

| Treatments | Yields (bales/acre) |
|---|---|
| 500 ml/ha DAT 511 | 4.51 ± 0.11 a |
| 2 L/ha GreenFire | 3.54 ± 0.19 a |
| 2 L/ha Plant X | 4.17 ± 0.13 a |
| 1 L/ha Plant X | 4.45 ± 0.05 a |
| Thiamethoxam (Cruiser X) 600 g/L | 4.24 ± 0.21 a |
| Untreated (control) | 3.86 ± 0.42 a |
| Significant difference | P > 0.05 |

Means within columns followed by the same letters are not significantly different (P > 0.05), Tukey-Kramer Multiple comparison test.
DAT = Days after treatment The results of the 2012-13 season seed treatment trials indicate that the number of plants per metre, plants damaged Example 5

Evaluation of Novel Seed Treatments

Novel seed treatment options were evaluated at the Australian Cotton Research Institute (ACRI)

Method

The biological novel control options for seed treatments investigated in Example 4 was assessed further in a separate seed treatment trial at the ACRI during the 2012-13 season. The treatments investigated were:
 1. Plant X extract at 120 mL/kg seed;
 2. Greenfire at 76 mL/kg seed;
 3. Fungus (DAT 511) at 3.3 g spores/kg seed;
 4. Cruiser; and
 5. Cruiser Extreme.

Data for thrips adult and larval abundance and plant dry weights were recorded. D-Vac was used for sampling thrips and other insects on the cotton crops. Data was analysed in Genstat using ANOVA/LSD.

Results
Thrips Abundance and Species

Cruiser (86% thrips reduction) and Cruiser Extreme (84% thrips reduction) outperformed the other treatments on the first sampling date. On the last sampling date, Cruiser was the least efficacious treatment while all other treatments ranked equally.

On the first sample date Cruiser (33% reduction) and Cruiser Extreme (40% reduction) reduced thrips numbers significantly compared with the control. Interestingly, plots treated with DAT 511 (32% reduction) also significantly reduced thrips abundance, almost as well as Cruiser. Furthermore, at the fourth sample date both Cruiser Extreme (40% reduction) and DAT 511 (52% reduction) significantly reduced thrips abundance, with DAT 511 performing slightly better. Interestingly, on most of the sampling dates, plots treated with DAT 511 had lower thrips populations than the control, though this was not always significant.

For the first three sample dates in November, *Thrips tabaci* comprised >90% of the subsample, with approximately 0-8% *Frankliniella occidentalis*. Between the last week in November and the first week of December, the proportion of *T. tabaci* began to decline but generally remained above 80%. *F. occidentalis* did not exceed 15%. In the overall analysis, DAT 511 and Plant X coated seeds had the lowest proportions of *F. occidentalis*.

Plant Dry Weights Plant material was collected and dry weights recorded. The plots treated with DAT 511 had the highest dry weights on the second and fourth sampling dates, as well as in the overall analysis. This finding was interesting as the fungus did not appear to provide any measurable thrips control. Plant X and Greenfire treatments had the lowest dry weights on the second and fourth sampling dates. Cruiser performed as well as the DAT 511 treatment, but also as well as the Control.

D-Vac Samples

Overall, all treatments controlled jassids and collembolans, and had fewer Hemipteran pests.

Plant X, GreenFire and Cruiser Extreme reduced the abundance of predatory beetles, and Plant X and GreenFire reduced the number of spiders. Plant X and Cruiser Extreme had significantly less adult thrips and DAT 511 and Cruiser significantly more larvae than the Control.

Cruiser had significantly more mites than the control and all other treatments. All treatments had significantly less jassids than the Control. Plant X and Cruiser Extreme had also significantly less apple dimpling bugs. GreenFire, Cruiser Extreme, Cruiser and Plant X, in that order, also had significantly less total Hemipteran pests compared to the Control.

GreenFire, Cruiser Extreme and Plant X had significantly less beneficial Coleoptera with GreenFire significantly affecting Coccinellids and Red and Blue beetles. Plant X affected the latter equally.

DAT 511 had significantly higher ant populations than the Control and all other treatments.

Plant X and GreenFire significantly reduced total spider numbers compared to the Control and it appeared that both chemicals had a stronger effect on other spiders than on tangleweb spiders. All chemicals reduced the number of Collembola (springtails) compared to the control.

Yield

Yield data from the study performed at ACRI showed that the fungus 1 treatment had significantly higher yield (11.91 bales/ha) compared to the control and all other treatments (control=10.96, Plant X=10.64, GreenFire=10.40, Cruiser=10.92 and Cruiser Extreme=10.86 bales/ha; F=0.02, LSD=0.6726, df=47). There was no significant difference between these other treatment types.

Example 6

Efficacy of BC 667 and DAT 511 on the Abundance of *Helicoverpa* Spp. Eggs and Larvae, *Creontiades dilutus* (Green Mirids), and *Nezara viridula* (Green Vegetable Bugs) in Conventional Cotton Crops This trial was conducted on a commercial conventional cotton farm at Norwood near Moree in NSW to determine the efficacy of BC 667 (*Beauveria* spp.) and DAT 511 (*Metarhizium* spp.) on the abundance of *Helicoverpa* spp. eggs and larvae, *Creontiades dilutus* (green mirids), and *Nezara viridula* (green vegetable bugs) in a conventional cotton crop.

Method

The trial ran from 20 Dec. 2010 until 23 Mar. 2011. Treatments evaluated were:
1. 500 mL/ha BC 667 spore in oil ($1 \times 10^7$ spores/ml);
2. 500 mL/ha DAT 511 spore in oil ($1 \times 10^7$ spores/ml);
3. 850 mL/ha Indoxacarb (conventional insecticide for *Helicoverpa* spp.);
4. 62.5 mL/ha fipronil (conventional insecticide for green mirids, green vegetable bugs and other sucking pests); and
5. Unsprayed (control).

Cotton plots treated with the fungal products were compared with unsprayed (control) plots and conventional insecticide treated plots. Plots were arranged in a randomized complete block design with 4 replicates. Each replicate measured 6 m (six rows) by 100 m long.

Foliar applications of each treatment were made on 20 Dec. 2010 and thereafter when the *Helicoverpa* spp. larval threshold of 2.0 larvae per metre and the green mirid threshold of 0.5 per metre were reached. Each treatment was applied with a ground spray rig commonly used to apply water-based sprays to achieve a droplet size (VMD) in the range 80 250 μm. On each occasion, treatments were applied using 100 L/ha of water. A total of six sprays of each treatment were applied during the season. Sprays on 1 Feb., 26 Feb. and 10 Mar. 2011 were targeting green mirids and green vegetable bugs. The control plot was left unsprayed and the synthetic insecticide treated plot received the same number of sprays as the fungal products.

Insect counts were done 24 hours before treatment application and then approximately every seven days until the end of the study. On each sampling date, visual counts of *Helicoverpa* spp. stages, green mirids (adults and nymphs) and green vegetable bugs (adults and nymphs) on whole cotton plants were made in four selected 1-metre lengths of row of each treatment i.e. four metres per treatment. Counts were separated into *Helicoverpa* spp. eggs, very small and small (VS+S) larvae (1st-3rd instar stage) and medium and large (M+L) (4th-6th instar stage) larvae. Data were expressed as numbers per metre for each treatment.

Predators of *Helicoverpa* spp. and other cotton pests were sampled weekly on cotton plants in each treatment. In each count, four randomly selected 1-metre lengths of row of each treatment replicate, i.e. a total of four metres, were examined per treatment. Predators were separated into predatory beetles, predatory bugs, predatory lacewings and spiders. The data were expressed as numbers per metre for each treatment.

Cotton in each treatment and unsprayed control plots was harvested using a two-row cotton harvester (picker) at the end of the season and the average yield (bales per acre) was compared.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Efficacy BC 667 and DAT 511 on the Abundance of *Helicoverpa* Spp.

No significant difference in the number of eggs per metre was found among treatments and control (FIG. 9). In contrast, the study showed that both *Beauveria* (BC667) and *Metarhizium* spp. (DAT 511) were highly efficacious against *Helicoverpa* spp. very small and small (1-2nd instar) larvae (FIG. 10) but low efficacy against medium and large larvae (FIG. 11). No significant difference ($P>0.05$) in the number of *Helicoverpa* spp. eggs per metre was found among treated and control (unsprayed) plots (FIG. 9) indicating that neither the fungi or the synthetic insecticides had ovicidal or anti-feedant effect against *Helicoverpa* spp. The number of *Helicoverpa* spp. VS+S and M+L larvae recorded on the fungi and the synthetic insecticide treated plots were not significantly different but was different from the unsprayed (control) plots (FIGS. 10 and 11).

Efficacy BC 667 and DAT 511 on the Abundance of Green Mirids and Green Vegetable Bugs Both BC 667 and DAT 511 were found to be efficacious against green mirid adults and nymphs (FIG. 12). The number of green mirid adults and nymphs recorded in plots treated with BC 667 and DAT 511 were not significantly different ($P>0.05$) from plots treated with fipronil (FIG. 12) but was significantly different ($P<0.001$) from the unsprayed (control) plots (FIG. 12). The number of green mirid adults and nymphs per metre recorded in the unsprayed plot was significantly higher ($P<0.001$) than the plots treated with BC 667, DAT 511 (fungus) and fipronil insecticide (FIG. 12).

No green vegetable bug infestation was recorded in the study site from 20 October until 17 Jan. 2011 (FIG. 13). When the plots were eventually infected by green vegetable bug, both BC 667 and DAT 511 were efficacious against very small (1st-2nd instar) nymphs (FIG. 13). The control given by both BC 667 and DAT 511 to 1st-2nd instar nymphs of green vegetable bugs was similar to conventional insecticides (Fipronil) (FIG. 13).

Effect of BC 667 and DAT 511 on Yield of Conventional Cotton

Plots treated with conventional insecticides yielded 5.10 bales/acre compared with 4.98, 4.78 and 2.15 bales/acre harvested from BC 667, DAT 511 and unsprayed (control) plots respectively. The yield loss was attributed to both *Helicoverpa* spp. and sucking pests.

Example 7

Efficacy of BC 667 and DAT 511 on the Abundance of *Helicoverpa* Spp. Eggs and Larvae, *Creontiades dilutus* (Green Mirids), *Nezara viridula* (Green Vegetable Bugs) and Beneficial Insects in Transgenic Cotton Crops This trial was conducted on commercial Bollgard II® cotton crops at Norwood near Moree in NSW to determine the efficacy of BC 667 and DAT 511 on the abundance of *Helicoverpa* spp. eggs and larvae, *Creontiades dilutus* (green mirids), *Nezara viridula* (green vegetable bugs) and beneficial insects in commercial transgenic (Bollgard II®) cotton crops.

Method

The trial was conducted on commercial Bollgard II® cotton crops at Norwood near Moree, NSW from 5 Dec. 2010 to 19 Feb. 2011. The cotton was at the early squaring stage, when it was attractive to green mirids (Khan et al. 2004).

The study evaluated the efficacy of the following treatments against green mirids, green vegetable bugs and predatory insects:

1. 500 mL/ha BC 667 spore in oil ($1 \times 10^7$ spores/ml);
2. 500 mL/ha DAT 511 spore in oil ($1 \times 10^7$ spores/ml);
3. 62.5 mL/ha Fipronil (conventional insecticide); and
4. Unsprayed (control).

The treatment plots were arranged in a randomized complete block design with four replicates per treatment. Each replicated plot measured 0.5 ha. Foliar application of each treatment was made on 18 Jan. 2011 using a ground spray rig fitted with flat fan nozzles to achieve a droplet size of 80 250 μm. The treatment was applied in the mornings when temperature was between 20° C. and 28° C. The timing of treatment was based on an economic threshold of 0.5 green mirids per metre, the IPM guideline and recommendation by CottonLogic.

Pre-treatment counts of green mirid adults and nymphs, predatory beetles, predatory bugs, predatory lacewings and spiders were made by visual inspection of whole cotton plants. Both adults and nymphs of the beneficial insects were counted. Plants were assessed in randomly selected one-metre lengths of row of each treatment replicate (i.e. four metres per treatment). In all, two spray applications of each treatment were made. The first spray was made on 18 Jan. 2011. Post-treatment counts of the first spray application were taken 3, 7 and 14 days after treatment (DAT) (first spray). A second spray application was done on 1 Feb. 2011 when green mirid adults plus nymphs reached the threshold of 0.5 per metre. Post-treatment counts of the second spray application were taken 3, 7, 14, 21 and 28 DAT. Data are expressed as numbers of individuals of that species counted per metre for each treatment.

Cotton in each treated plot was harvested separately using a four-row picker (John Deere, Model 9965, USA) at the end of the season and the average lint yields (bales/acre) were compared between treatments.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Efficacy of BC 667 and DAT 511 on the Abundance of Green Mirids and Green Vegetable Bugs Both BC 667 and DAT 511 were found to be efficacious against green mirid adults and nymphs, similar to Fipronil insecticides after two consecutive sprays of the fungus (FIG. 14). The first spray application of BC 667 and DAT 511 caused 80.2% and 83.5% mortality respectively when measured three DAT. Fipronil caused 100% mortality (FIG. 14). After the first spray application, the number of green mirids per metre increased in the BC 667 and DAT 511 treated plots at 7 DAT to approximately 2.33/metre. This was due to the eggs on the crops prior to the first spray that hatched and produced nymphs that did not come into contact with the fungus. After the second spray, BC 667 and DAT 511 reduced the number of green mirids per metre to 0.67 and 0.33 respectively at 28 DAT (FIG. 14).

The number of green vegetable bugs per metre in plots treated with BC 667 and DAT 511 was also not significantly different (P>0.05) from plots treated with fipronil, but was significantly lower (P<0.0001) than the unsprayed plots (FIG. 15).

Efficacy of BC 667 and DAT 511 on the Abundance of Beneficial Insects

Beneficial insects identified in the treated plots were predominantly predators including predatory beetles, bugs, lacewings and spiders (Table 7). Populations of predatory beetles were not significantly different (P>0.05) among treated and control plots (Tables 8 and 9). A similar trend was shown by predatory bugs on fungus treated plots which were not significantly different (P>0.05) from the unsprayed plots. However, fipronil treated plots had a significantly lower population (P<0.01) than the unsprayed plots at 14, 21 and 28 days after the 2nd spray application (Tables 10 and 11).

No significant difference (P>0.05) was found in the number of lacewings per metre between the fungus treated and the unsprayed plots. However, populations of lacewings recorded on the fipronil treated plots was significantly lower (P<0.01) after the 2nd spray than both the fungus treated and the unsprayed plots at 7 and 14 days after the 2nd spray (Tables 12 and 13).

Spiders were always the most abundant predator species (Tables 14 and 15). The population of spiders recorded on the fungus treated plots were the same as the unsprayed plots (Tables 14 and 15). The fipronil treated plots had significantly lower (P<0.001) numbers of spiders per metre than the fungus and unsprayed at three and seven DAT (1st spray) and 14, 21 and 28 DAT (2nd spray) (Tables 14 and 15).

TABLE 7

Predators of cotton pests sampled and identified from the study site during 2010-2011.

| Order | Family | Species | Group |
|---|---|---|---|
| Coleoptera | Coccinellidae | *Coccinella transversalis* (Fabricius) | Predatory beetles |
| | | *Diomus notescens* (Blackburn) | |
| | Melyridae | *Dicranolauis bellulus* (Guerin-Meneville) | |
| Hemiptera | Nabidae | *Nabis capsiformis* (Germar) | Predatory bugs |
| | Lygaeidae | *Geocoris lubra* (Kirkaldy) | |
| | Pentatomidae | *Cermatulus nasalis* (Westwood) | |
| | | *Ochelia schellenbergii* (Guerin-Meneville) | |
| | | *Coranus triabeatus* (Horvath) | |
| Neuroptera | Chrysopidae | *Chrysopa* spp. | Predatory lacewings |
| | Hemerobiidae | *Micromus tasmaniae* (walker) | |
| Araneida | Lycosidae | *Lycosa* spp. | Spiders |
| | Oxyopidae | *Oxyopes* spp. | |
| | Salticidae | *Salticidae* spp. | |
| | Araneidae | *Araneus* spp. | |

TABLE 8

Efficacy of BC 667 and DAT 511 fungal biopesticides on the number of predatory beetles per meter in commercial cotton crops at Norwood, near Moree, 2010-11 (1st spray).

| Treatments | Pre-spray counts 18 Jan. 2011 | 3 DAT 21 Jan. 2011 | 7 DAT 25 Jan. 2011 | 14 DAT 1 Feb. 2011 |
|---|---|---|---|---|
| 0.50 L/ha BC 667 | 2.33 ± 0.88 a | 0.00 ± 0.00 a | 0.67 ± 0.33 a | 0.00 ± 0.00 a |
| 0.50 L/ha DAT 511 | 0.33 ± 0.33 a | 0.00 ± 0.00 a | 0.33 ± 0.33 a | 0.00 ± 0.00 a |
| 62.5 mL/ha fipronil | 0.67 ± 0.33 a | 0.00 ± 0.00 a | 0.00 ± 0.00 a | 0.00 ± 0.00 a |
| Unsprayed (control) | 0.67 ± 0.33 a | 1.00 ± 0.58 a | 0.67 ± 0.33 a | 0.33 ± 0.33 a |
| Level of significance | P > 0.11 | P > 0.12 | P > 0.19 | P > 0.46 |

Means between treatments within columns followed by the same letter are not significantly different (P > 0.05); Tukey-Kramer multiple comparison test.
DAT = Days after treatment.

TABLE 9

Efficacy of BC 667 and DAT 511 fungal biopesticides on the number of predatory beetles per metre in commercial cotton crops at Norwood, near Moree, 2010-11 (2nd spray).

| Treatments | Pre-spray counts 1 Feb. 2011 | 3 DAT 4 Feb. 2011 | 7 DAT 8 Feb. 2011 | 14 DAT 15 Feb. 2011 | 21 DAT 22 Feb. 2011 | 28 DAT 1 Mar. 2011 |
|---|---|---|---|---|---|---|
| 0.5 L/ha BC667 | 0.00 ± 0.00a | 0.67 ± 0.33a | 0.67 ± 0.33a | 1.33 ± 0.33ab | 1.33 ± 0.33a | 1.00 ± 0.58a |
| 0.5 L/ha DAT 511 | 0.00 ± 0.00a | 1.00 ± 0.58a | 1.67 ± 0.67a | 1.67 ± 0.33ab | 2.33 ± 0.33a | 1.67 ± 0.33a |
| 62.5 mLl/ha fipronil | 0.00 ± 0.00a | 0.33 ± 0.33a | 0.33 ± 0.33a | 0.00 ± 0.00a | 1.00 ± 0.58a | 0.67 ± 0.33a |
| Unsprayed (control) | 0.33 ± 0.33a | 1.33 ± 0.33a | 2.00 ± 0.58a | 2.00 ± 0.58b | 2.33 ± 0.33a | 2.67 ± 0.33a |
| Level of significance | P > 0.46 | P > 0.24 | P > 0.20 | P < 0.04 | P > 0.16 | P > 0.07 |

Means between treatments within columns followed by the same letter are not significantly different (P > 0.05); Tukey-Kramer multiple comparison test.
DAT = Days after treatment.

TABLE 10

Efficacy of BC 667 and DAT 511 fungal biopesticides on the number of predatory bugs per meter in commercial cotton crops at Norwood, near Moree, 2010-11 (1st spray).

| Treatments | Pre-spray counts 18 Jan. 2011 | 3 DAT 21 Jan. 2011 | 7 DAT 25 Jan. 2011 | 14 DAT 1 Feb. 2011 |
| --- | --- | --- | --- | --- |
| 0.50 L/ha BC 667 | 0.67 ± 0.33 a | 0.67 ± 0.33 a | 1.67 ± 0.33 a | 1.33 ± 0.33 a |
| 0.50 L/ha DAT 511 | 0.00 ± 0.00 a | 1.00 ± 0.58 a | 2.00 ± 0.58 a | 1.00 ± 0.58 a |
| 62.5 mL/ha fipronil | 0.67 ± 0.33 a | 0.33 ± 0.33 a | 0.67 ± 0.33 a | 1.33 ± 0.33 a |
| Unsprayed (control) | 0.33 ± 0.33 a | 1.67 ± 0.33 a | 2.67 ± 0.33 a | 1.67 ± 0.33 a |
| Level of significance | P > 0.19 | P > 0.21 | P > 0.09 | P > 0.76 |

Means between treatments within columns followed by the same letter are not significantly different (P > 0.05); Tukey-Kramer multiple comparison test.
DAT = Days after treatment.

TABLE 11

Efficacy of BC 667 and DAT 511 fungal biopesticides on the number of predatory bugs per metre in commercial cotton crops at Norwood, near Moree, 2010-11 (2nd spray).

| Treatments | Pre-spray counts 1 Feb. 2011 | 3 DAT 4 Feb. 2011 | 7 DAT 8 Feb. 2011 | 14 DAT 15 Feb. 2011 | 21 DAT 22 Feb. 2011 | 28 DAT 1 Mar. 2011 |
| --- | --- | --- | --- | --- | --- | --- |
| 0.5 L/ha BC 667 | 1.33 ± 0.33a | 1.33 ± 0.33a | 0.67 ± 0.33a | 0.67 ± 0.33ab | 2.00 ± 0.58ab | 1.00 ± 0.58ab |
| 0.5 L/ha DAT 511 | 1.00 ± 0.58a | 1.33 ± 0.67a | 1.00 ± 0.58a | 1.00 ± 0.58ab | 3.00 ± 0.58b | 1.67 ± 0.33b |
| 62.5 mL/ha fipronil | 1.33 ± 0.33a | 0.33 ± 0.33a | 0.33 ± 0.33a | 0.67 ± 0.33a | 1.00 ± 0.58a | 0.67 ± 0.33a |
| Unsprayed (control) | 1.67 ± 0.33a | 1.00 ± 0.58a | 2.00 ± 0.58a | 2.33 ± 0.33b | 3.67 ± 0.33b | 2.67 ± 0.33b |
| Level of significance | P > 0.76 | P > 0.14 | P > 0.13 | P > 0.04 | P < 0.0001 | P < 0.01 |

Means between treatments within columns followed by the same letter are not significantly different (P > 0.05); Tukey-Kramer multiple comparison test.
DAT = Days after treatment.

TABLE 12

Efficacy of BC 667 and DAT 511 fungal biopesticides on the number of lacewings per meter in commercial cotton crops at Norwood, near Moree, 2010-11 (1st spray).

| Treatments | Pre-spray counts 18 Jan. 2011 | 3 DAT 21 Jan. 2011 | 7 DAT 25 Jan. 2011 | 14 DAT 1 Feb. 2011 |
| --- | --- | --- | --- | --- |
| 0.50 L/ha BC 667 | 2.33 ± 0.88 a | 1.33 ± 0.33 b | 0.67 ± 0.33 a | 0.67 ± 0.33 a |
| 0.50 L/ha DAT 511 | 0.67 ± 0.33 a | 1.67 ± 0.33 b | 1.33 ± 0.33 a | 0.67 ± 0.33 a |
| 62.5 mL/ha fipronil | 0.67 ± 0.33 a | 0.00 ± 0.00 a | 0.00 ± 0.00 a | 0.33 ± 0.33 a |
| Unsprayed (control) | 1.67 ± 0.33 a | 2.67 ± 0.33 b | 1.33 ± 0.67 a | 1.00 ± 0.58 a |
| Level of significance | P > 0.19 | P < 0.0008 | P > 0.07 | P > 0.71 |

Means between treatments within columns followed by the same letter are not significantly different (P > 0.05); Tukey-Kramer multiple comparison test.
DAT = Days after treatment.

TABLE 13

Efficacy of BC 667 and DAT 511 fungal biopesticides on the number of lacewings per metre in commercial cotton crops at Norwood, near Moree, 2010-11 (2nd spray).

| Treatments | Pre-spray counts 1 Feb. 2011 | 3 DAT 4 Feb. 2011 | 7 DAT 8 Feb. 2011 | 14 DAT 15 Feb. 2011 | 21 DAT 22 Feb. 2011 | 28 DAT 1 Mar. 2011 |
| --- | --- | --- | --- | --- | --- | --- |
| 0.5 L/ha BC 667 | 0.67 ± 0.33a | 2.33 ± 0.33a | 1.33 ± 0.33ab | 1.67 ± 0.33a | 2.67 ± 0.88a | 3.33 ± 0.88a |
| 0.5 L/ha DAT 511 | 0.67 ± 0.33a | 1.33 ± 0.33a | 1.67 ± 0.33ab | 2.67 ± 0.67ab | 3.67 ± 0.33a | 3.67 ± 0.67a |

TABLE 13-continued

Efficacy of BC 667 and DAT 511 fungal biopesticides on the number of lacewings per metre in commercial cotton crops at Norwood, near Moree, 2010-11 (2nd spray).

| Treatments | Pre-spray counts 1 Feb. 2011 | 3 DAT 4 Feb. 2011 | 7 DAT 8 Feb. 2011 | 14 DAT 15 Feb. 2011 | 21 DAT 22 Feb. 2011 | 28 DAT 1 Mar. 2011 |
|---|---|---|---|---|---|---|
| 62.5 mL/ha fipronil | 0.33 ± 0.33a | 0.33 ± 0.33a | 0.67 ± 0.33a | 0.67 ± 0.33a | 1.67 ± 0.33a | 1.33 ± 0.33a |
| Unsprayed (control) | 1.00 ± 0.58a | 1.67 ± 0.33a | 2.33 ± 0.58b | 3.33 ± 0.33b | 3.33 ± 0.88a | 4.00 ± 0.58a |
| Level of significance | $P > 0.71$ | $P > 0.05$ | $P < 0.02$ | $P < 0.03$ | $P > 0.17$ | $P > 0.13$ |

Means between treatments within columns followed by the same letter are not significantly different ($P > 0.05$); Tukey-Kramer multiple comparison test.
DAT = Days after treatment.

TABLE 14

Efficacy of BC 667 and DAT 511 fungal biopesticides on the number of spiders per meter in commercial cotton crops at Norwood, near Moree, 2010-11 (1st spray).

| Treatments | Pre-spray counts 18 Jan. 2011 | 3 DAT 21 Jan. 2011 | 7 DAT 25 Jan. 2011 | 14 DAT 1 Feb. 2011 |
|---|---|---|---|---|
| 0.50 L/ha BC 667 | 10.67 ± 1.20 a | 11.67 ± 2.03 ab | 11.67 ± 2.40 a | 13.67 ± 2.03 a |
| 0.50 L/ha DAT 511 | 9.00 ± 0.58 a | 9.00 ± 2.31 ab | 14.67 ± 0.88 a | 15.67 ± 2.03 a |
| 62.5 mL/ha fipronil | 9.33 ± 1.20 a | 3.33 ± 0.33 a | 4.67 ± 2.03 b | 9.67 ± 1.45 a |
| Unsprayed (control) | 8.67 ± 1.20 a | 13.00 ± 2.08 b | 15.00 ± 2.65 a | 18.00 ± 1.53 a |
| Level of significance | $P > 0.69$ | $P < 0.04$ | $P < 0.04$ | $P > 0.10$ |

Means between treatments within columns followed by the same letter are not significantly different ($P > 0.05$); Tukey-Kramer multiple comparison test.
DAT = Days after treatment.

TABLE 15

Efficacy of BC 667 and DAT 511 fungal biopesticides on the number of spiders per metre in commercial cotton crops at Norwood, near Moree, 2010-11 (2nd spray).

| Treatments | Pre-spray counts 1 Feb. 2011 | 3 DAT 4 Feb. 2011 | 7 DAT 8 Feb. 2011 | 14 DAT 15 Feb. 2011 | 21 DAT 22 Feb. 2011 | 28 DAT 1 Mar. 2011 |
|---|---|---|---|---|---|---|
| 0.5 L/ha BC667 | 13.67 ± 2.03a | 16.33 ± 1.67a | 15.67 ± 2.33a | 22.33 ± 2.40ab | 33.67 ± 0.88ab | 32.33 ± 1.20a |
| 0.5 L/ha DAT 511 | 15.67 ± 2.03a | 16.33 ± 2.33a | 18.33 ± 0.33a | 20.33 ± 2.03ab | 32.00 ± 3.22ab | 31.33 ± 2.40a |
| 62.5 mL/ha fipronil | 9.67 ± 1.45a | 12.00 ± 1.16a | 10.33 ± 2.67a | 16.00 ± 0.58b | 21.00 ± 3.22a | 21.00 ± 3.00a |
| Unsprayed (control) | 18.00 ± 1.53a | 20.00 ± 1.53a | 20.33 ± 2.67a | 23.67 ± 2.85a | 35.00 ± 2.31b | 33.33 ± 2.60a |
| Level of significance | $P > 0.10$ | $P > 0.11$ | $P > 0.10$ | $P < 0.04$ | $P < 0.04$ | $P > 0.05$ |

Means between treatments within columns followed by the same letter are not significantly different ($P > 0.05$); Tukey-Kramer multiple comparison test.
DAT = Days after treatment.

Effect of BC 667 and DAT 511 on Yields of Bollgard Cotton Crops at Norwood

No significant difference was recorded in plots treated with BC 667, DAT 511 and fipronil. However, plots treated with BC 667 and DAT 511 had significantly higher yields than the unsprayed (control) plots (Table 16).

TABLE 16

Cotton yield of commercial cotton crops managed without any treatment, using a commercial synthetic insecticide, or three levels of application of a fungal insecticide at Norwood, near Moree, 2011-12.

| Treatments | Yields (bales/acre) |
| --- | --- |
| 0.50 L/ha BC 667 3.28 | 4.13 ± 0.88 a |
| 0.50 L/ha DAT 511 3.38 | 4.57 ± 0.33 a |
| 62.5 mL/ha fipronil | 4.67 ± 0.63 a |
| Unsprayed (control) | 3.17 ± 0.33 b |
| Level of significance | P < 0.01 |

Means between treatments within columns followed by the same letter are not significantly different (P > 0.05); Tukey-Kramer multiple comparison test.
DAT = Days after treatment.

Example 8

Efficacy of DAT 511 Against *Helicoverpa* Spp. and Predatory Insects (Predatory Beetles, Predatory Bugs, Lacewings and Spiders) on Conventional Cotton Crops This trial was undertaken to identify the optimum rate of application for DAT 511 and optimum time of day for application of fungal sprays to achieve maximum efficacy against *Helicoverpa* spp., sucking pests and beneficial insects. The trial was also used to determine the action threshold for application of DAT 511 to achieve maximum efficacy against *Helicoverpa* spp. and sucking pests in cotton crops.

Method

The trial was conducted on conventional cotton crops at ACRI in Narrabri during the 2011-12 season. Each treatment was 200 m$^2$ in accordance with APVMA Permit 7250.

Treatments evaluated were:
1. 250 mL/ha DAT 511;
2. 500 mL/ha DAT 511;
3. 1.0 L/ha DAT 511;
4. Conventional insecticides (Steward—sprays 1 and 2; Tracer II—spray 3); and
5. Unsprayed (control).

The treatments were arranged in a randomized complete block design with three replicates. The unsprayed plot was left untreated. Foliar application of each treatment was made on 8 Jan. 18 Jan. and 8 Feb. 2012 using knapsack spray equipment fitted with flat fan nozzles to achieve a droplet size of 200 μm. The treatments were applied in the mornings when the temperature was between 20° C. and 25° C. The timing of treatment was based on an economic threshold of 2 larvae per metre, IPM guidelines and recommendations by CottonLogic.

Pre-treatment counts of *Helicoverpa* spp. eggs, very small+small larvae (VS+S=1st-3rd instar), medium+large larvae (M+L=4th-5th instar), predatory beetles, predatory bugs, predatory lacewings and spiders were made by visual inspection of whole cotton plants. Both adults and larvae of predatory insects were counted. Plants were assessed in randomly selected one-metre lengths of row of each treatment replicate (i.e. three metres per treatment). Post-treatment counts were made 3, 7, 14, 21 and 28 DAT. Data were expressed as numbers of individuals of that species counted per metre per treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Density of *Helicoverpa* Spp. Eggs

The number of *Helicoverpa* eggs per metre recorded in plots treated with 250 mL, 500 mL and 1.0 L/ha DAT 511 was the same as the conventional insecticide treated plots but significantly different (P<0.001) to the unsprayed plots (FIG. 16). The results also showed that after two spray applications of DAT 511 (8 and 19 Jan. 2013), the number of *Helicoverpa* spp. eggs recorded in the 1.0 L/ha DAT 511 plots was significantly lower than the 250 and 500 mL/ha DAT 511 and the insecticide treated plots (FIG. 18). However, at 14 DAT (2nd spray) (5 Feb. 2013), the same number of *Helicoverpa* spp. eggs per metre was found in 1.0 L/ha and 500 mL/ha DAT 511, and synthetic insecticide treated plots, but the number of eggs recorded in the 250 mL/ha and the unsprayed plots were significantly higher (P<0.01) (FIG. 16). Overall, the fungus and synthetic insecticide had low ovicidal effect and did not deter *Helicoverpa* spp. to lay eggs on the treated plants.

Density of *Helicoverpa* Spp. Very Small and Small Larvae

Significantly fewer (P<0.0001) *Helicoverpa* spp. very small and small larvae (VS+S) (1st-3rd instar) per metre were found on plots treated with 250 mL, 500 mL and 1.0 L/ha DAT 511, and conventional insecticide than the unsprayed plots (FIG. 17). Nevertheless, the number of *Helicoverpa* spp. VS+S larvae per metre recorded on plots treated with 250 mL/ha DAT 511 was significantly higher (P<0.001) than plots treated with 500 mL and 1.0 L/ha DAT 511, and conventional insecticide from 10 Jan. to 5 Feb. 2012. Thereafter, no significant difference was found among the fungus and conventional insecticide treated plots (FIG. 17). Overall, the 500 mL and 1.0 L/ha DAT 511 rates controlled *Helicoverpa* spp. VS+S larvae similar to the conventional insecticides. The 250 mL/ha DAT 511 rate was not enough to reduce the VS+S larvae population above the commercial threshold of 2.0 larvae per metre (FIG. 17).

Density of *Helicoverpa* Spp. Medium and Large Larvae

The results showed that the number of *Helicoverpa* spp. medium+large larvae per metre was significantly lower (P<0.0001) in plots treated with 250 mL, 500 mL and 1.0 L/ha DAT 511, and conventional insecticide than the unsprayed plots (FIG. 18). Plots treated with 250 mL/ha DAT 511 was significantly higher (P<0.0001) on the 10 Jan. to 22 Jan. 2012 than 500 mL and 1.0 L/ha DAT 511, and conventional insecticide treated plots (FIG. 18). After the second spray application (19 Jan. 2012), the number of *Helicoverpa* spp. medium and large larvae on the 250 mL/ha treated plots declined significantly to be the same as those recorded on the 500 mL, 1.0 L/ha and conventional insecticide treated plots on 7 Feb. 2012 (FIG. 18). Similarly, the number of *Helicoverpa* spp. M+L larvae recorded on the unsprayed plots also declined from four per metre on 7 Feb. 2012 to two per metre on 22 Feb. 2012. The decline in *Helicoverpa* spp. numbers on the unsprayed plots was found to be due to larvae moving from the unsprayed plots which had fewer fruits to the treated plots with high fruit load to avoid starvation.

Density of Predatory Beetles

Predominant predatory beetles identified in the study sites are given in Table 7. The results showed that fungal biopesticides are more selective on predatory beetles than the conventional insecticides (FIG. 19). No significant difference (P>0.05) was found in the number of predatory beetles per metre between DAT 511 treated plots and the unsprayed plots, except plots treated with 1 L/ha DAT 511 which recorded significantly lower (P<0.01) numbers of predatory beetles per metre than the unsprayed plots (FIG. 19). The plots treated with conventional synthetic insecticides had no predatory beetles after the first spray application (8 Jan. 2012). The number of predatory beetles did not recover on the conventional insecticide treated plots until 15 Feb. 2012 and crashed again on 22 Feb. 2012 (FIG. 19). The number of predatory beetles per metre recorded in plots treated with 1.0 L/ha DAT 511 had consistently lower numbers of predatory beetles per metre than the plots treated with 250 and 500 mL/ha DAT 511 and the unsprayed plots (FIG. 19).

Density of Predatory Bugs

Predatory bugs identified in the study are given in Table 7. No significant difference (P>0.05) was found in the number of predatory bugs per metre between DAT 511 treated plots and the unsprayed plots (FIG. 20). However, the number of predatory bugs recorded in the conventional insecticide treated plots was significantly lower (P<0.01) than the unsprayed plots and plots treated with the varying rates of the fungal biopesticide DAT 511 (FIG. 20).

Overall, the synthetic insecticides exterminated the predatory bugs (FIG. 22).

Density of Predatory Lacewings

The predominant lacewings identified from the study plots were *Chrysopa* spp. and *Micromus tasmaniae* (Table 7). No significant difference (P>0.05) in the number of predatory lacewings per metre was found between plots treated with 250 and 500 mL/ha DAT 511 and the unsprayed plots (FIG. 21). In contrast, the number of predatory lacewings per metre recorded on plots treated with 1 L/ha DAT 511 and conventional insecticides were significantly lower (P<0.01) than 250 and 500 mL/ha DAT 511 and the unsprayed plots (FIG. 21). Overall, plots treated with 1.0 L/ha DAT 511 and conventional insecticides consistently had the lowest number of predatory lacewings per metre than the 250 and 500 mL/ha DAT 511, and unsprayed plots (FIG. 21). The results indicated that application of 250 and 500 mL/ha DAT 511 on cotton crops to control pests would have less impact against predatory lacewings than 1.0 L/ha DAT 511 and the conventional insecticides used in this study.

Density of Spiders

Spiders identified from the study plots were *Lycosa* spp., *Oxyopes* spp., *Salticidae* spp. and *Araneus* spp. (Table 7). The number of spiders per metre recorded in the DAT 511 treated plots and unsprayed plots were not significantly different from each other but were significantly higher (P<0.001) than the conventional insecticide treated plots (FIG. 22). The results indicate that application of DAT 511 at lower and higher rates are more selective than the conventional insecticides used in this study (FIG. 22).

Example 9

Efficacy of DAT 511 Against Green Vegetable Bugs, Green Mirids and Apple Dimpling Bugs on Conventional Cotton Crops The purpose of this trial was to evaluate the efficacy of varying rates of DAT 511 on green vegetable bugs (GVB), green mirids and apple dimpling bugs (ADB).

Method

This trial was conducted in an irrigated field of commercial conventional cotton at the Australian Cotton Research Institute (ACRI) farm in Narrabri, NSW, during the 2011-2012 season. The treatments in this trial were as follows:
1. 250 mL/ha DAT 511;
2. 500 mL/ha DAT 511; and
3. 1 L/ha DAT 511.

Results were compared with data from unsprayed conventional cotton crops (negative control) and conventional cotton crops treated with 62.5 mL/ha of fipronil. The population of apple dimpling bugs at the study site was higher than GVB and green mirids, and remained so throughout the season. Therefore the trials were treated and assessed from 8 Jan. to 12 Feb. 2012 for green mirids, 26 Feb. 2012 for GVB and 4 Mar. 2012 for apple dimpling bugs. The treatment plots were arranged in a randomized complete block design with eight replicates per treatment. Each replicated plot measured 16 m (16 rows) wide and 250 m long.

Foliar applications of each treatment were made on 8 Jan. 22 Jan. and 5 Feb. 2012. The decision to apply the treatment was based on the IPM Guidelines and the CottonLogic recommended economic threshold of 0.5 green mirids per metre. Pre-treatment counts were made by visual counting of the numbers of green mirid, green vegetable bug and apple dimpling bug adults and nymphs, as well as predatory beetles, predatory bugs, predatory lacewings and spiders on cotton plants in each treatment. Post-treatment counts were made following the first spray at 7 and 14 DAT, following the second spray at 7 DAT for green mirids and GVB, and up to 28 DAT for the third spray for apple dimpling bugs. All counts were done on a randomly selected one-metre length of row of each treatment replicate (i.e. total of 8 m). Data were expressed as numbers per metre and numbers per metre per sampling date for each treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Density of Green Vegetable Bugs

The number of green vegetable bugs (adults and nymphs) recorded in plots treated with different rates of DAT 511 were not significantly different (P>0.05). However, significantly fewer green vegetable bugs were found in plots treated with DAT 511 relative to the unsprayed plots (P<0.0001) (FIGS. 23 and 24). Overall, approximately 2.34 times as many green vegetable bugs per metre were recorded in the untreated plots than in plots treated with fungal insecticides (FIGS. 23 and 24). Accordingly, the results of this study show that there were less green vegetable bugs per metre recorded on plots treated with DAT 511 relative to unsprayed plot. These result demonstrate that DAT 511 would be effective in controlling green vegetable bugs on cotton crops.

Density of Green Mirids

Significantly fewer (P<0.0001) adult and nymph green mirids were found in plots treated with different rates of DAT 511 and fipronil insecticide than on unsprayed (control) plots (FIGS. 25, 26, 27 and 28). At the first spray application, the number of green mirid adults per metre recorded on plots treated with 500 mL and 1 L/ha DAT 511, and fipronil insecticide was not significantly different (P>0.05) between 8 and 29 Jan. 2012 but was significantly different from plots treated with 250 mL/ha DAT 511 (P<0.01) and unsprayed plots (P<0.0001) (FIGS. 25 and 26). At the second spray application, no adult mirids were found on fungus and fipronil treated plots (FIGS. 25 and 26). Overall, approximately 2.2, 3.8 and 5.6 times as many green mirid adults per metre per sample date were recorded on the unsprayed plots than on plots treated with 250 mL, 500 mL and 1 L/ha DAT 511 respectively (FIGS. 25 and 26).

Similarly, the number of green mirid nymphs per metre recorded on plots treated with 500 mL and 1 L/ha DAT 511, and fipronil insecticide was not significantly different (P>0.05) at the first and second spray application between 8 Jan. and 12 Feb. 2012 (FIG. 28). On 22 Jan. and 12 Feb. 2012, the number of green mirid nymphs recorded on plots treated with 250 mL/ha DAT 511 was significantly higher (P<0.001) than plots treated with 500 mL and 1 L/ha DAT 511, and fipronil but lower (P<0.0001) than the unsprayed plots (FIG. 28). Seven days after the second spray application, no mirid nymphs were found in plots treated with 500 mL and 1.0 L/ha DAT 511, and fipronil compared to 0.50 and 1.50 mirids per metre recorded on the 250 mL/ha DAT 511 treated and unsprayed plots (FIG. 28).

Overall, approximately 2.1, 4.2 and 3.6 times as many green mirid nymphs per metre per sample date were recorded in the unsprayed plots than in plots treated with 250 mL, 500 mL and 1.0 L/ha DAT 511 respectively (FIG. 28). These result demonstrate that DAT 511 would be effective in controlling green mirid adults and nymphs.

Density of Apple Dimpling Bugs

The number of adult and nymph apple dimpling bugs recorded in the 250 mL and 500 mL/ha DAT 511 treated plots was the same as the unsprayed plots and also plots treated with 1.0 L/ha DAT 511 and conventional insecticides (FIGS. 29, 30, 31 and 32). In contrast, the number of apple dimpling bug adults and nymphs recorded in 1.0 L/ha DAT 511 and conventional insecticide treated plots was significantly lower (P<0.05) than the unsprayed plots (FIGS. 29, 30, 31 and 32).

At the first spray application, apple dimpling bug adults per metre on both treated and untreated plots declined after three days. Plots treated with 500 mL and 1 L/ha DAT 511, and conventional insecticides recorded the highest decline from 8 Jan. to 22 Jan. 2012 (FIG. 30). The number of ADB adults increased in the fungus treated plots on 15 Feb. 2012 before it crashed at the end of the study. Both unsprayed and fungus treated plots consistently recorded higher ADB adult numbers per metre compared with the conventional insecticide treated plots (FIGS. 29 and 30). Overall, approximately 1.2, 1.3, and 1.5 times as many ADB adults and 1.0, 1.2 and 1.5 times as many ADB nymphs were recorded on the untreated plots than in plots treated with 250 mL, 500 mL and 1 L/ha DAT 511 respectively (FIGS. 29, 31 and 32).

Example 10

Efficacy of Fungal Biopesticides Against Green Mirids and Beneficial Insects

This trial was undertaken to determine the efficacies of varying rates of DAT 511 that can effectively control sucking pests, especially green mirids, green vegetable bugs and silverleaf whiteflies, in conventional cotton crops.

Method

This trial was conducted on commercial conventional cotton crops on a farm at Norwood (29° 28'S, 149° 50'E) near Moree, NSW, from 28 Feb. to 21 Mar. 2012. The cotton used for the trial was at the early squaring stage, when it was attractive to green mirids (Khan et al. 2004).

The efficacy of the following treatments against green mirids and predatory insects were evaluated:
1. 250 mL/ha DAT 511 spore in oil ($1 \times 10^7$ spores/ml);
2. 500 mL/ha DAT 511 spore in oil ($1 \times 10^7$ spores/ml);
3. 1 L/ha DAT 511 spore in oil ($1 \times 10^7$ spores/ml);
4. 62.5 mL/ha of Fipronil; and
5. Unsprayed (negative control).

The treatment plots were arranged in a randomized complete block design with six replicates per treatment. Each replicated plot measured 40 m wide (40 rows) and 90 m long.

Foliar application of each treatment was made on 28 Feb. (for both green mirids and beneficial insects) and 13 Mar. 2012 (for beneficial insects alone) using a ground spray rig fitted with flat fan nozzles to achieve a droplet size of 200 µm. The treatment was applied in the mornings when temperature was between 20° C. and 28° C. The timing of treatment was based on the IPM Guidelines and recommendations by CottonLogic to use an economic threshold of 0.5 green mirids per metre (Deutscher and Wilson 1999; Khan et al. 2004).

Pre-treatment counts of adult and nymph green mirids, predatory beetles, predatory bugs, predatory lacewings and spiders were made by visual inspection of whole cotton plants. Both adults and nymphs of beneficial insects were counted. Plants were assessed in randomly selected one-metre lengths of row of each treatment replicate (i.e. 6 m per treatment). Post-treatment counts were made 3, 7, 14 and 21 DAT. Data are expressed as numbers of green mirid adults and nymphs counted per metre per treatment.

Data Analysis

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Density of Green Mirids

The number of green mirid adults and nymphs recorded in plots treated with different rates of DAT 511 were not significantly different (P>0.05) from plots treated with fipronil (FIGS. 33, 34, 35 and 36). The number of green mirid adults and nymphs per metre recorded in the unsprayed plot was significantly higher (P<0.001) than the plots treated with DAT 511 fungus and fipronil insecticide (FIGS. 33, 34, 35 and 36). In contrast, plots treated with 250 mL/ha DAT 511 had significantly higher (P<0.05) numbers of green mired adults per metre on 6 and 20 Mar. 2012 than plots treated with higher rates of DAT 511 and fipronil insecticide (FIG. 33). Overall, approximately 1.9, 2.6 and 2.6 times as many green mirid adults and 2.0, 2.8 and 3.6 times as many green mirid nymphs were recorded in the unsprayed, 250 mL, 500 mL and 1.0 L/ha DAT 511 respectively (FIGS. 34 and 35). These result show that DAT 511 would be effective in controlling green mirid adults and nymphs.

Density of Beneficial Insects

Predatory insects were the most common beneficial insects found in the study site and they are listed in Table 7. No significant difference (P>0.05) in the number of predatory bugs, lacewings and spiders was found between DAT 511, fipronil and the unsprayed (control) plots (FIGS. 37, 38, 39 and 40). In contrast, the number of predatory beetles per metre recorded in the fipronil-treated plots on the 3 and 6 Mar. 2012 were significantly lower (P<0.05) than on the unsprayed and DAT 511 treated plots (FIG. 37). This indicates that the fungus was selective against all predatory beetles, predatory bugs, lacewings and spiders but fipronil was selective against predatory bugs, lacewings and spiders and not predatory beetles (FIGS. 37, 38, 39 and 40).

Example 11

Efficacy of Fungal Biopesticides Against Silverleaf Whiteflies (*Bemisia tabaci*)

This trial was undertaken to determine the efficacies of varying rates of application of DAT 511 that can effectively control silverleaf whiteflies in transgenic cotton crops relative to conventional insecticides for this pest.

Method

This trial was conducted on an irrigated Bollgard II® cotton crop on a commercial cotton farm at Norwood near Moree, NSW, in 2011-2012.

The following treatments were evaluated against *Bemisia tabaci* b-type adults and nymphs:
1. 250 mL/ha DAT 511 spore in oil ($1 \times 10^7$ spores/ml);
2. 500 mL/ha DAT 511 spore in oil ($1 \times 10^7$ spores/ml);
3. 1 L/ha DAT 511 spore in oil ($1 \times 10^7$ spores/ml);
4. 500 mL/ha Pyriproxyfen (conventional insecticide); and
5. Unsprayed (control).

The treatment plots were arranged in a randomized complete block design with three replicates per treatment. Each replicated plot measured 40 m wide (40 rows) and 90 m long.

Foliar applications of each treatment were made on 28 Feb. and 20 Mar. 2012. Pre-treatment counts of *B. tabaci* adults and nymphs on the under-surface of leaves of cotton plants in each treatment were made on 28 Feb. 2012 (1st spray) and 20 Mar. 2012 (2nd spray). Post-treatment counts were made 3, 7, 14 and 21 days after treatment. On each sampling date, 20 plants from each replicate were randomly selected and *B. tabaci* adults on one leaf from the 5th node below the terminal of each plant were counted. This was done during early morning hours (9-10 am) by carefully turning the leaf over and counting the number of individual adults present.

In the case of nymphs, one leaf from the 5th node below the terminal of each of the 20 plants was cut, removed and carefully placed individually in a plastic bag. The plastic bags containing the leaves were taken to the laboratory and the *B. tabaci* nymphs were counted under a binocular microscope. Data of both adults and nymphs were expressed as numbers per leaf per treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparison tests were used to separate the means.

Results

Density of Silverleaf Whiteflies (SLW)

Figure 41B:
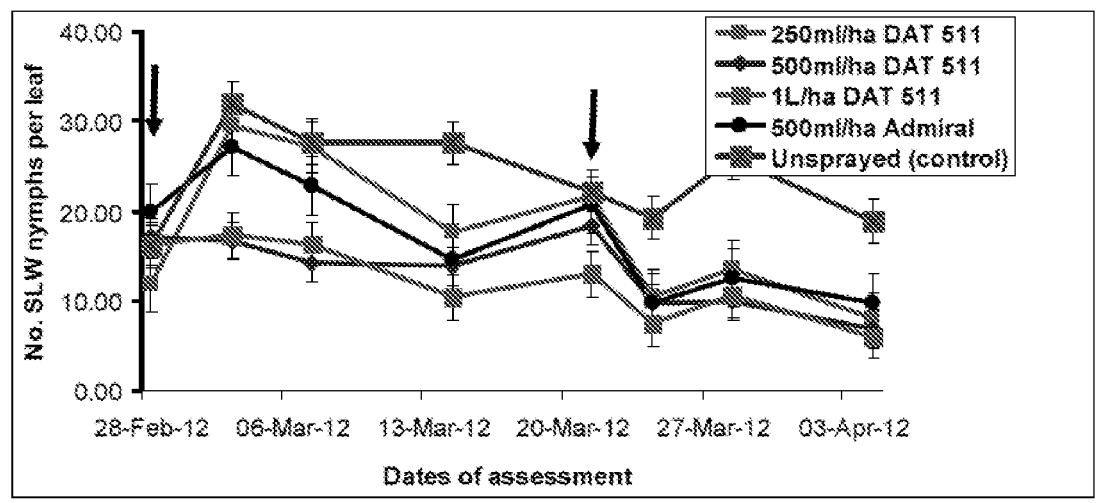

No significant differences were detected in the number of silverleaf whitefly adults and nymphs in plots treated with different rates of DAT 511 and conventional insecticide (Admiral) treated plots (FIGS. 41 A and B). The DAT 511 and Admiral treated plots had fewer ($P<0.001$) SLW adults and nymphs than the unsprayed (FIGS. 41 A and B). Plots treated with 500 mL/ha and 1.0 L/ha DAT 511 consistently recorded fewer SLW nymphs than fipronil treated plots but were not significantly different ($P>0.05$) (FIG. 41B).

Example 12

Efficacy of Fungal Biopesticides Against Green Mirids, Green Vegetable Bugs, Apple Dimpling Bugs and Beneficial Predatory Insects This trial was undertaken to determine the efficacies of varying rates of application of DAT 511 that can effectively control green mirids, green vegetable bugs, apple dimpling bugs and beneficial insects in conventional cotton refuge crops relative to conventional insecticides.

Method

This trial was conducted using commercial conventional cotton refuge crops at Undabri in Goondiwindi (28° 55'S, 150° 31'E) from 14 Feb. to 6 Mar. 2012.

The efficacy of the following treatments against green mirids, green vegetable bugs and predatory insects was assessed:
1. 250 mL/ha DAT 511 spore in oil ($1 \times 10^7$ spores/ml);
2. 500 mL/ha DAT 511 spore in oil ($1 \times 10^7$ spores/ml);
3. 1 L/ha DAT 511 spore in oil ($1 \times 10^7$ spores/ml);
4. 62.5 mL/ha fipronil; and
5. Unsprayed (negative control).

The plots were arranged in a randomized complete block design with three replicates per treatment. Each replicated plot measured 8 m (8 rows) wide and 250 m long.

Foliar applications of each treatment were made on 14 Feb. 2012 using a ground spray rig fitted with flat fan nozzles to achieve a droplet size of 200 µm. All insecticide formulations were water miscible. All treatments were applied using a spray volume of 100 L/ha. The untreated (negative control) plot was left unsprayed and the plot treated with synthetic insecticide received two applications similar to, and on the same date as, the plots treated with the fungus.

For each replicate, visual counts of adults and nymphs of green mirids, green vegetable bugs (GVB), apple dimpling bugs and predatory insects on whole cotton plants were made in a randomly selected 1 m length of row of cotton plants (i.e. 6 m per treatment). Pre-treatment counts were made on 28 Feb. 2012 and post-treatment counts were made 3, 7, 14 and 21 days after treatment. One-metre lengths of cotton rows were randomly selected in each replicate (i.e. a total of 6 m was examined per treatment). The predatory insects were classified as either predatory beetles, bugs, lacewings or spiders. Data were expressed separately for adults and nymphs of green mirids, apple dimpling bugs, predatory beetles, predatory bugs, predatory lacewings and spiders, and data for adults and nymphs were combined for green vegetable bug. Each insect group was expressed both as total numbers of individuals per metre and numbers of individuals per metre per sample date.

Cotton in each treated plot was harvested separately using a four-row picker (John Deere, Model 9965, USA) at the end of the season and the average lint yields (bales/acre) were compared between treatments.

Analysis of Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate means.

Results

Density of Green Mirids

Significantly fewer green mirid adults ($P<0.03$) and nymphs ($P<0.001$) per metre were found on plots treated with DAT 511 and fipronil than on unsprayed plots (FIGS.

42 A and B). No significant differences (P>0.05) were found between DAT 511 and fipronil treated plots, indicating that DAT 511 controlled green mirid adults and nymphs similar to that of fipronil (FIGS. 42 A and B).

Density of Green Vegetable Bugs

No significant differences in the number of green vegetable bugs per metre were found on the fungus and insecticide treated, and unsprayed plots between 17 Feb. (3 DAT) and 21 Feb. (7 DAT) (FIG. 43). On 28 Feb. (14 DAT) and 6 Mar. 2012 (21 DAT), the number of green vegetable bugs recorded on unsprayed plots had significantly higher (P<0.01; 14 DAT), (P<0.05; 21 DAT) green vegetable bugs per metre than plots treated with 500 mL/ha DAT 511, 1 L/ha DAT 511 and fipronil (FIG. 43).

Density of Apple Dimpling Bugs

The results showed that plots treated with different rates of DAT 511 and fipronil had significantly fewer (P<0.01) apple dimpling bug adults per metre than the unsprayed plot when counts were taken at 3, 7, 14 and 21 DAT (17 Feb. to 6 Mar. 2012) (FIG. 44). The number of apple dimpling bug nymphs per metre recorded on plots treated with DAT 511 and fipronil was significantly lower (P<0.05) than the unsprayed plots at 7 DAT (21 Feb. 2012) only, thereafter the number of apple dimpling bug nymphs per metre was the same among treated and unsprayed plots (FIG. 45).

Density of Predatory Insects

Predatory insects identified in the study plots are given in Table 7. The results showed that application of 250 mL/ha, 500 mL/ha and 1.0 L/ha DAT 511 to cotton plants did not significantly affect the number of predatory beetles, predatory lacewings and spiders (FIGS. 46, 48 and 49). However, application of 500 mL and 1.0 L/ha DAT 511 affected the number of predatory bugs per metre recorded on the cotton crops (P<0.001) compared to plots treated with 250 mL/ha DAT 511 and the unsprayed plots (FIG. 47). In contrast, the number of predatory bugs, lacewings and spiders per metre recorded on the fipronil treated plots was significantly lower (P<0.01, P<0.01, P<0.04 and P<0.05 respectively) (FIGS. 47, 48 and 49) than on the unsprayed and DAT 511 treated plots, except for the numbers of predatory beetles per metre which were identical (P>0.05) to the DAT 511 and unsprayed plots (FIG. 46).

Example 13

Efficacy of Fungal Biopesticides Against Silverleaf Whiteflies (*Bemisia tabaci*)

This trial was undertaken to determine the efficacies of varying rates of application of DAT 511 that can effectively control silverleaf whiteflies in transgenic cotton crops relative to conventional insecticides for this pest.

Method

This trial was conducted on an irrigated Bollgard cotton crop on a commercial cotton farm at Cooinda, St George, Queensland, in 2011-2012.

The following treatments were evaluated against *Bemisia tabaci* b-type adults and nymphs:
1. 250 mL/ha DAT 511 spore in oil ($1\times10^7$ spores/ml);
2. 500 mL/ha DAT 511 spore in oil ($1\times10^7$ spores/ml);
3. 1 L/ha DAT 511 spore in oil ($1\times10^7$ spores/ml);
4. 500 mL/ha Pyriproxyfen (conventional insecticide); and
5. Unsprayed (control).

The treatment plots were arranged in a randomized complete block design with three replicates per treatment. Each replicated plot measured 40 m wide (40 rows) and 90 m long.

Foliar applications of each treatment were made on 12 Mar. and 26 Mar. 2012. Pre-treatment counts of *B. tabaci* adults and nymphs on the under-surface of leaves of cotton plants in each treatment were made on 12 Mar. 2012 (1st spray) and 26 Mar. 2012 (2nd spray). Post-treatment counts were made 3, 7, 14 and 21 days after treatment. On each sampling date, 20 plants from each replicate were randomly selected and *B. tabaci* adults on one leaf from the 5th node below the terminal of each plant were counted. This was done during early morning hours (9-10 am) by carefully turning the leaf over and counting the number of individual adults present.

In the case of nymphs, one leaf from the 5th node below the terminal of each of the 20 plants was cut, removed and carefully placed individually in a plastic bag. The plastic bags containing the leaves were taken to the laboratory and the *B. tabaci* nymphs were counted under a binocular microscope. Data of both adults and nymphs were expressed as numbers per leaf per treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer multiple comparisons tests were used to separate the means.

Results

Significantly fewer (P<0.001) silverleaf whitefly adults and nymphs per metre were found in plots treated with DAT 511 and Pyriproxyfen (Admiral) insecticide than on unsprayed plots (FIG. 50). No significant differences (P>0.05) were found between DAT 511 and Pyriproxyfen (Admiral) insecticide treated plots, indicating that the ability of DAT 511 to control silverleaf whitefly populations was similar to that of Pyriproxyfen (Admiral) insecticide, the most common commercial insecticide used in the cotton industry to manage silverleaf whiteflies.

Example 14

Efficacy of Fungal Biopesticides Against Green Mirids and Beneficial Predatory Insects This trial was undertaken to determine the efficacies of varying rates of application of DAT 511 that can effectively control green mirids and beneficial predatory insects in transgenic cotton crops relative to conventional insecticides.

Method

Two separate trials (Experiment 1 in Field 77; Experiment 2 in Field 63) were conducted in Bollgard II cotton crops on a commercial cotton farm at Auscott-Togo near Narrabri, New South Wales from 11 Feb. to 5 Mar. 2013 (Field 77) and 19 Feb. to 6 Mar. 2013 (Field 63). The cotton used for each of the trials was at the late squaring to pod setting and maturation stages which was fairly attractive to green mirids.

In both trials, the efficacy of the following treatments against green mirids and predatory insects was evaluated:
1. 250 mL/ha DAT 511 spore in oil ($1\times10^7$ spores/ml);
2. 500 mL/ha DAT 511 spore in oil ($1\times10^7$ spores/ml);
3. 1 L/ha DAT 511 spore in oil ($1\times10^7$ spores/ml);
4. 62.5 mL/ha of fipronil; and
5. Unsprayed (negative control).

The treatment plots were arranged in a randomized complete block design with six replicates per treatment. Each replicated plot measured 40 m wide (40 rows) and 90 m long.

Foliar application of each treatment was made on 28 Feb. (for both green mirids and beneficial insects) and 13 Mar. 2012 (for beneficial insects alone) using a ground spray rig fitted with flat fan nozzles to achieve a droplet size of 200 µm. The treatment was applied during the mornings when temperatures were between 20° C. and 28° C. The timing of treatment was based on the IPM Guidelines and recommendations by CottonLogic to use an economic threshold of 0.5 green mirids per metre (Deutscher and Wilson 1999; Khan et al. 2004).

Pre-treatment counts of green mirid adults and nymphs, predatory beetles, predatory bugs, predatory lacewings and spiders were made by visual inspection of whole cotton plants. Both adults and nymphs of beneficial insects were counted. Plants were assessed in randomly selected one-metre lengths of row of each replicate (i.e. 6 m per treatment). Post-treatment counts were made 3, 7, 14 and 21 days after treatment. Data are expressed as numbers of green mirid adults and nymphs counted per metre for each treatment.

Data Analysis

All experimental data were analysed using repeated measures ANOVA (Graphpad Instat and Prism Software, Inc. v. 2.03, San Diego, Calif., USA). Treatment and sample dates were the independent variables. Tukey_Kramer multiple comparisons tests were used to separate means.

Results

Experiment 1 (Field 77)

The number of green mirid adults and nymphs recorded in plots treated with different rates of DAT 511 were not significantly different (P>0.05) from plots treated with fipronil and the unsprayed plots at three days after treatment (Table 17). However, at 7, 14 and 21 DAT, the number of green mirid adults and nymphs per metre was significantly lower (P<0.01, P<0.0004 and P<0.007 respectively) in plots treated with 500 mL/ha and 1.0 L/ha DAT 511, and fipronil than the unsprayed plots (Table 17). The number of green mirid adults and nymphs recorded in the 250 mL/ha DAT 511 treated plots was significantly different (P<0.01) at 14 DAT only (Table 17).

Predatory insects identified from the study plots are listed in Table 7. Significantly lower (P<0.01, P<0.004 and P<0.007) number of predatory beetles were found on DAT 511 treated plots than the unsprayed plots, with the exception of plots treated with 250 mL/ha DAT 511 which was not significantly different (P>0.05) from the unsprayed plots (Table 18). In contrast, no significant difference (P>0.05) was found in the number of predatory bugs and lacewings per metre in plots treated with fungus, fipronil and unsprayed (control) plots (Table 19, 20). The number of spiders per metre recorded in the fungus and fipronil treated plots was the same as the unsprayed plots, except at 3 DAT where the fipronil treated plots had significantly fewer (P<0.04) spiders per metre than the unsprayed plots (Table 21). The study showed that DAT 511 is selective on predatory insects.

TABLE 17

Efficacy of DAT 511 fungal biopesticides on the number of green mirid adults and nymphs per meter on commercial Bollgard II cotton crops in Field 77 (Experiment 1) at Auscott-Togo, Narrabri, 2012-13.

| Treatments | No. green mirid adults and nymphs per meter | | | | |
| --- | --- | --- | --- | --- | --- |
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 1.33 ± 0.33 a | 2.00 ± 0.58 a | 1.33 ± 0.33 ab | 1.33 ± 0.33 a | 0.67 ± 0.33 ab |
| 500 mL/ha DAT 511 | 2.33 ± 0.33 a | 1.33 ± 0.33 a | 0.67 ± 0.33 b | 0.67 ± 0.33 a | 0.33 ± 0.33 a |
| 1.0 L/ha DAT 511 | 3.00 ± 1.00 a | 1.33 ± 0.33 a | 0.33 ± 0.33 b | 0.33 ± 0.33 a | 0.33 ± 0.33 a |
| 62.5 mL/ha fipronil | 4.33 ± 0.67 a | 1.33 ± 0.33 a | 0.00 ± 0.00 b | 0.00 ± 0.00 a | 0.00 ± 0.00 a |
| Unsprayed (control) | 1.33 ± 0.33 a | 2.00 ± 0.58 a | 2.67 ± 0.67 a | 3.67 ± 0.33 b | 2.00 ± 0.58 b |
| Level of significance | P > 0.05 | P > 0.69 | P < 0.01 | P < 0.0004 | P < 0.007 |

Means between treatments within columns followed by the same letter are not significantly different (P > 0.05); Tukey-Kramer multiple comparison test.
DAT = Days after treatment.

TABLE 18

Efficacy of DAT 511 fungal biopesticides on the number of predatory beetles per meter on commercial Bollgard II cotton crops in Field 77 (Experiment 1) at Auscott-Togo, Narrabri, 2012-13.

| Treatments | No. predatory beetles per meter | | | | |
| --- | --- | --- | --- | --- | --- |
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 3.00 ± 0.58 a | 3.33 ± 0.88ab | 2.00 ± 0.58 a | 3.67 ± 0.88 a | 3.33 ± 0.33 a |
| 500 mL/ha DAT 511 | 3.33 ± 1.20 a | 3.00 ± 0.58ab | 1.67 ± 0.33 a | 3.67 ± 0.67 a | 3.67 ± 0.67 a |
| 1.0 L/ha DAT 511 | 4.33 ± 0.33 a | 2.67 ± 0.33ab | 2.00 ± 0.58 a | 3.00 ± 0.58 a | 3.33 ± 0.33 a |
| 62.5 mL/ha fipronil | 3.68 ± 0.33 a | 1.33 ± 0.33 a | 1.33 ± 0.33 a | 1.00 ± 0.58 a | 1.33 ± 0.33 b |
| Unsprayed (control) | 4.68 ± 0.67 a | 5.00 ± 1.16 b | 2.67 ± 0.33 a | 3.67 ± 0.88 a | 3.67 ± 0.67 a |
| Level of significance | P > 0.48 | P < 0.01 | P > 0.40 | P > 0.09 | P < 0.0001 |

Means between treatments within columns followed by the same letter are not significantly different (P > 0.05); Tukey-Kramer multiple comparison test.
DAT = Days after treatment.

TABLE 19

Efficacy of DAT 511 fungal biopesticides on the number of predatory bugs per meter on commercial Bollgard II cotton crops in Field 77 (Experiment 1) at Auscott-Togo, Narrabri, 2012-13.

| | No. predatory beetles per meter | | | | |
|---|---|---|---|---|---|
| Treatments | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 0.67 ± 0.33 a | 0.33 ± 0.33 a | 0.33 ± 0.33 a | 1.00 ± 0.58 a | 0.67 ± 0.33 a |
| 500 mL/ha DAT 511 | 0.33 ± 0.33 a | 0.00 ± 0.33 a | 0.33 ± 0.33 a | 1.33 ± 0.33 a | 0.33 ± 0.33 a |
| 1.0 L/ha DAT 511 | 0.33 ± 0.33 a | 0.00 ± 0.00 a | 0.33 ± 0.33 a | 0.33 ± 0.33 a | 0.33 ± 0.33 a |
| 62.5 mL/ha fipronil | 0.33 ± 0.33 a | 0.33 ± 0.00 a | 0.00 ± 0.00 a | 0.00 ± 0.00 a | 0.67 ± 0.33 a |
| Unsprayed (control) | 1.33 ± 0.33 a | 0.33 ± 0.33 a | 0.67 ± 0.33 a | 1.00 ± 0.58 a | 1.33 ± 0.67 a |
| Level of significance | $P > 0.07$ | $P > 0.46$ | $P > 0.31$ | $P > 0.29$ | $P > 0.13$ |

Means between treatments within columns followed by the same letter are not significantly different ($P > 0.05$); Tukey-Kramer multiple comparison test.
DAT = Days after treatment.

TABLE 20

Efficacy of DAT 511 fungal biopesticides on the number of predatory lacewings per meter on commercial Bollgard II cotton crops in Field 77 (Experiment 1) at Auscott-Togo in Narrabri, 2012-13.

| | No. predatory lacewings per meter | | | | |
|---|---|---|---|---|---|
| Treatments | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 0.00 ± 0.00 a | 0.33 ± 0.33 a | 0.33 ± 0.33 a | 0.67 ± 0.33 a | 0.33 ± 0.33 a |
| 500 mL/ha DAT 511 | 0.00 ± 0.00 a | 0.33 ± 0.33 a | 0.00 ± 0.00 a | 0.67 ± 0.33 a | 0.33 ± 0.33 a |
| 1.0 L/ha DAT 511 | 0.00 ± 0.00 a | 0.00 ± 0.00 a | 0.00 ± 0.00 a | 0.33 ± 0.33 a | 0.33 ± 0.33 a |
| 62.5 mL/ha fipronil | 0.00 ± 0.00 a | 0.00 ± 0.00 a | 0.00 ± 0.00 a | 0.33 ± 0.33 a | 0.33 ± 0.33 a |
| Unsprayed (control) | 0.33 ± 0.33 a | 0.33 ± 0.33 a | 0.00 ± 0.00 a | 1.00 ± 0.58 a | 0.33 ± 0.33 a |
| Level of significance | $P > 0.46$ | $P > 0.46$ | $P > 0.31$ | $P > 0.71$ | $P > 0.99$ |

Means between treatments within columns followed by the same letter are not significantly different ($P > 0.05$); Tukey-Kramer multiple comparison test.
DAT = Days after treatment.

TABLE 21

Efficacy of DAT 511 fungal biopesticides on the number of spiders per meter on commercial Bollgard II cotton crops in Field 77 (Experiment 1) at Auscott-Togo, Narrabri, 2012-13.

| | No. spiders per meter | | | | |
|---|---|---|---|---|---|
| Treatments | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 10.33 ± 3.76a | 10.33 ± 2.60 ab | 7.33 ± 1.76 a | 12.00 ± 2.52a | 9.33 ± 2.19 a |
| 500 mL/ha DAT 511 | 15.67 ± 2.19a | 10.00 ± 0.58 ab | 6.67 ± 0.33 a | 16.67 ± 3.33a | 8.67 ± 1.86 a |
| 1.0 L/ha DAT 511 | 10.67 ± 1.76a | 10.67 ± 0.88 ab | 6.00 ± 0.58 a | 13.33 ± 3.33a | 12.67 ± 1.33 a |
| 62.5 mL/ha fipronil | 11.67 ± 1.67a | 5.00 ± 1.73 a | 5.33 ± 1.86 a | 9.33 ± 0.67a | 8.67 ± 0.88 a |
| Unsprayed (control) | 8.00 ± 2.00a | 17.00 ± 3.00 b | 9.33 ± 2.85 a | 14.00 ± 3.06a | 10.67 ± 0.67 a |
| Level of significance | $P > 0.34$ | $P < 0.04$ | $P > 0.55$ | $P > 0.32$ | $P > 0.26$ |

Means between treatments within columns followed by the same letter are not significantly different ($P > 0.05$); Tukey-Kramer multiple comparison test.
DAT = Days after treatment.

Experiment 2 (Field 63)

Significantly fewer ($P<0.02$ and $P<0.004$) green mirid adults and nymphs per metre were found on plots treated with DAT 511 and fipronil than on unsprayed plots at seven and 14 DAT (Table 22). The number of green mirid adults and nymphs was the same in all treatments at three and 21 DAT (Table 21).

Application of DAT 511 fungus to cotton plants did not have a significant negative effect against predatory beetles, bugs and lacewings (Tables 23, 24 and 25). A similar trend was found between the fungus treated and unsprayed plots (Table 26). The number of spiders per metre recorded on the fipronil treated plots was the same as the fungus and unsprayed plots at 3, 14 and 21 DAT but was significantly fewer ($P<0.005$) than the fungus treated and unsprayed plots at 7 DAT (Table 26).

TABLE 22

Efficacy of DAT 511 fungal biopesticides on the number of green mirid adults and nymphs per meter on commercial Bollgard II cotton crops in Field 63 (Experiment 2) at Auscott-Togo, Narrabri, 2012-13.

| Treatments | No. green mirid adults and nymphs per meter | | | | |
|---|---|---|---|---|---|
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 2.33 ± 0.67 a | 1.67 ± 0.67 a | 0.67 ± 0.33 ab | 1.00 ± 0.58ab | 0.00 ± 0.00 a |
| 500 mL/ha DAT 511 | 3.00 ± 0.58 a | 0.67 ± 0.33 a | 0.33 ± 0.33 ab | 0.33 ± 0.33 a | 0.00 ± 0.00 a |
| 1.0 L/ha DAT 511 | 3.67 ± 0.88 a | 0.33 ± 0.33 a | 0.00 ± 0.00 a | 0.33 ± 0.33 a | 0.00 ± 0.00 a |
| 62.5 mL/ha fipronil | 1.67 ± 0.33 a | 0.33 ± 0.33 a | 0.00 ± 0.00 a | 0.33 ± 0.33 a | 0.00 ± 0.00 a |
| Unsprayed (control) | 1.67 ± 0.33 a | 3.00 ± 1.00 a | 2.00 ± 0.57 b | 1.67 ± 0.33 b | 1.00 ± 0.58 a |
| Level of significance | $P > 0.08$ | $P > 0.09$ | $P < 0.02$ | $P < 0.004$ | $P > 0.09$ |

Means between treatments within columns followed by the same letter are not significantly different ($P > 0.05$); Tukey-Kramer multiple comparison test.
DAT = Days after treatment.

TABLE 23

Efficacy of DAT 511 fungal biopesticides on the number of predatory beetles per meter on commercial Bollgard II cotton crops in Field 63 (Experiment 2) at Auscott-Togo, Narrabri, 2012-13.

| Treatments | No. predatory beetles per meter | | | | |
|---|---|---|---|---|---|
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 3.67 ± 0.33 a | 3.00 ± 1.00 a | 2.67 ± 0.67 a | 1.33 ± 0.33 a | 2.00 ± 0.58 a |
| 500 mL/ha DAT 511 | 3.00 ± 0.58 a | 3.33 ± 0.33 a | 2.00 ± 0.58 a | 1.00 ± 0.58 a | 2.33 ± 0.33 a |
| 1.0 L/ha DAT 511 | 7.00 ± 0.58 b | 2.67 ± 0.33 a | 1.33 ± 0.33 a | 0.67 ± 0.33 a | 1.33 ± 0.67 a |
| 62.5 mL/ha fipronil | 5.67 ± 0.67ab | 2.67 ± 0.33 a | 2.33 ± 0.33 a | 0.67 ± 0.33 a | 1.67 ± 0.33 a |
| Unsprayed (control) | 5.00 ± 1.00ab | 5.67 ± 1.20 a | 2.67 ± 0.33 a | 2.67 ± 0.33 a | 2.33 ± 0.33 a |
| Level of significance | $P < 0.01$ | $P > 0.12$ | $P > 0.41$ | $P > 0.42$ | $P > 0.42$ |

Means between treatments within columns followed by the same letter are not significantly different ($P > 0.05$); Tukey-Kramer multiple comparison test.
DAT = Days after treatment.

TABLE 24

Efficacy of DAT 511 fungal biopesticides on the number of predatory bugs per meter on commercial Bollgard II cotton crops in Field 63 (Experiment 2) at Auscott-Togo, Narrabri, 2012-13.

| Treatments | No. predatory bugs per meter | | | | |
|---|---|---|---|---|---|
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 0.00 ± 0.00 a | 0.00 ± 0.00 a | 0.67 ± 0.33 a | 0.33 ± 0.33 a | 0.67 ± 0.33 a |
| 500 mL/ha DAT 511 | 0.67 ± 0.33 a | 0.00 ± 0.00 a | 0.67 ± 0.33 a | 0.33 ± 0.33 a | 0.33 ± 0.33 a |
| 1.0 L/ha DAT 511 | 0.00 ± 0.00 a | 0.00 ± 0.00 a | 0.67 ± 0.33 a | 0.67 ± 0.33 a | 0.00 ± 0.00 a |
| 62.5 mL/ha fipronil | 0.00 ± 0.00 a | 0.00 ± 0.00 a | 0.33 ± 0.33 a | 0.00 ± 0.00 a | 0.00 ± 0.00 a |
| Unsprayed (control) | 0.67 ± 0.33 a | 0.00 ± 0.00 a | 0.33 ± 0.33 a | 0.67 ± 0.33 a | 0.67 ± 0.33 a |
| Level of significance | $P > 0.05$ | $P > 0.46$ | $P > 0.46$ | $P > 0.23$ | $P > 0.13$ |

Means between treatments within columns followed by the same letter are not significantly different ($P > 0.05$); Tukey-Kramer multiple comparison test.
DAT = Days after treatment.

TABLE 25

Efficacy of DAT 511 fungal biopesticides on the number of predatory lacewings per meter on commercial Bollgard II cotton crops in Field 63 (Experiment 2) at Auscott-Togo, Narrabri, 2012-13.

| Treatments | No. predatory lacewings per meter | | | | |
|---|---|---|---|---|---|
| | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 0.67 ± 0.33 a | 0.67 ± 0.33 a | 0.00 ± 0.00 a | 0.00 ± 0.00 a | 0.33 ± 0.33 a |
| 500 mL/ha DAT 511 | 0.33 ± 0.33 a | 0.33 ± 0.33 a | 0.00 ± 0.00 a | 0.00 ± 0.00 a | 0.33 ± 0.33 a |
| 1.0 L/ha DAT 511 | 0.33 ± 0.33 a | 0.33 ± 0.33 a | 0.00 ± 0.00 a | 0.00 ± 0.00 a | 0.00 ± 0.00 a |

TABLE 25-continued

Efficacy of DAT 511 fungal biopesticides on the number of predatory lacewings per meter on commercial Bollgard II cotton crops in Field 63 (Experiment 2) at Auscott-Togo, Narrabri, 2012-13.

| | No. predatory lacewings per meter | | | | |
|---|---|---|---|---|---|
| Treatments | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 62.5 mL/ha fipronil | 0.67 ± 0.33 a | 0.00 ± 0.00 a | 0.00 ± 0.00 a | 0.00 ± 0.00 a | 0.00 ± 0.00 a |
| Unsprayed (control) | 1.33 ± 0.33 a | 1.00 ± 0.33 a | 0.00 ± 0.00 a | 0.33 ± 0.33 a | 0.33 ± 0.33 a |
| Level of significance | P > 0.36 | P > 0.41 | P = 0 | P > 0.71 | P > 0.46 |

Means between treatments within columns followed by the same letter are not significantly different (P > 0.05); Tukey-Kramer multiple comparison test.
DAT = Days after treatment.

TABLE 26

Efficacy of DAT 511 fungal biopesticides on the number of spiders per meter on commercial Bollgard II cotton crops in Field 63 (Experiment 2) at Auscott-Togo, Narrabri, 2012-13.

| | No. spiders per meter | | | | |
|---|---|---|---|---|---|
| Treatments | Pre-spray counts 11 Feb. 2013 | 3 DAT 14 Feb. 2013 | 7 DAT 18 Feb. 2013 | 14 DAT 25 Feb. 2013 | 21 DAT 4 Mar. 2013 |
| 250 mL/ha DAT 511 | 10.00 ± 0.58a | 5.33 ± 1.76 a | 7.33 ± 1.45a | 3.00 ± 0.58a | 3.00 ± 1.00 a |
| 500 mL/ha DAT 511 | 8.33 ± 0.33a | 7.00 ± 2.08 a | 10.67 ± 0.67a | 3.67 ± 1.45a | 2.67 ± 0.88 a |
| 1.0 L/ha DAT 511 | 9.00 ± 0.58a | 8.67 ± 1.33 a | 6.33 ± 0.67a | 2.00 ± 0.58a | 2.67 ± 0.67 a |
| 62.5 mL/ha fipronil | 11.67 ± 1.61 a | 7.33 ± 1.45 a | 4.33 ± 0.67a | 1.33 ± 0.33a | 3.67 ± 0.33 a |
| Unsprayed (control) | 11.67 ± 1.67a | 6.33 ± 0.88 a | 10.33 ± 0.33a | 2.33 ± 1.33a | 4.67 ± 0.67 a |
| Level of significance | P > 0.23 | P > 0.64 | P < 0.005 | P > 0.53 | P > 0.29 |

Means between treatments within columns followed by the same letter are not significantly different (P > 0.05); Tukey-Kramer multiple comparison test.
DAT = Days after treatment.

Example 14

Environmental Fate after Application of BC 667 and DAT 511 in Irrigated and Dryland Cotton Crops As part of the preliminary trial conducted at ACRI near Narrabri to determine the efficacy of DAT511 and BC667 fungus against *Helicoverpa* spp., sucking pests and beneficial bugs on conventional and transgenic cotton crops (discussed previously), a concurrent study was undertaken to determine the environmental fate of the fungicidal biopesticide following their application to irrigated and dryland cotton crops.

Method

Field Sampling of Soil and Leaves 20 g soil and 5 leaf samples were collected from each replicate (3 replicates per treatment) of the unsprayed plots, 500 mL/ha BC 667 and 500 mL/ha DAT 511 treated plots at 4, 7, 14 and 20 days after treatment at each study site.

On each sampling date, 20 g soil from each treatment replicate was randomly collected using a shovel and carefully placed individually in a labelled plastic bag and placed into a cooler. In addition, 5 leaf samples were randomly selected from the 3rd-5th node below the terminal of each treated plant and carefully placed individually in a labelled plastic bag and then placed in a separate cooler containing ice blocks. The coolers containing the soil and leaf samples were brought to the laboratory at ACRI and placed in a refrigerator set at 4° C.

The soil and leaf samples were put in two separate coolers and sent to Becker Underwood Pty Ltd in Somersby near Sydney for spore analysis. Samples were labelled 'Unsprayed', 'BC 667' and 'DAT 511' for days 4, 7, 14 and 20 for both soil and leaves. Samples were maintained at 4° C. prior to experimentation in Becker Underwood laboratories.

Soil Analysis 11 g of soil from each sample was weighed and added to a sterile flask containing 99 mL deionised water and surfactant (dilution $10^0$).

The flask was shaken for 15 minutes on a wrist shaker to achieve a homogeneous solution.

1 mL of solution was then further diluted in 99 mL of deionised water and surfactant (dilution $10^{-2}$).

A sample of the $10^{-2}$ dilution was then viewed using microscopy and a Fuchs-Rosenthal Haemocytometer. Conidia were enumerated from random grids of known volume and counts were calculated per gram of soil. The $10^0$ dilution was not counted because the solution was too turbid.

Leaf Analysis

A circular leaf section of diameter 7.5 cm (area 44.2 $cm^2$) was removed from each sample and added to a sterile flask containing 99 mL deionised water and surfactant (dilution 100).

The flask was shaken for 15 minutes on a wrist shaker to achieve a homogeneous solution.

1 mL of solution was then further diluted in 99 mL of deionised water and surfactant (dilution $10^{-2}$).

A sample of both the 100 and $10^{-2}$ dilution were then viewed using microscopy and a Fuchs-Rosenthal Haemocytometer. Conidia were enumerated from random grids of known volume and counts were calculated per $cm^3$ of leaves.

Results

Conidia of *Metarhizium* spp. DAT511 and *Beauveria* spp. BC667 were found not to exist above detectable levels (>1×10$^3$ conidia/g) in soil from all treatment areas at all times.

On leaves there were conidia existing at 4 days after fungus treatment at detectable levels. BC667 conidia were measured at 2.83×10$^3$ per cm$^2$ from the BC667 treatment. DAT511 conidia were measured at 5.66×10$^3$ per cm$^2$.

Example 15

Environmental Fate after Application of DAT 511 in Irrigated and Dryland Cotton Crops As part of trials conducted at (i) ACRI near Narrabri, (ii) Norwood near Moree, (iii) Undabri near Goondiwindi and (iv) Cooinda in St George, to determine the efficacy of DAT511 fungus against *Helicoverpa* spp., sucking pests and beneficial bugs on conventional and transgenic cotton crops (discussed previously in Example 2-13), a concurrent study was undertaken to determine the environmental fate of the fungicidal biopesticide following their application to irrigated and dryland cotton crops.

Method
Field Sampling of Soil and Leaves

Soil and leaf samples were taken before and after spraying from both the unsprayed and DAT 511 plots in irrigated and dryland crops for analysis of residual fungal spores. Samples were taken from 4 treatments labelled 'Unsprayed', '250 mL/ha', '500 mL/ha' and '1.0 L/ha' at pre-spray, 3-4 days after treatment, 7 DAT and 14 DAT for both soil and leaves. Pre-spray samples from 500 mL/ha and 1.0 L/ha were omitted to minimise unnecessary duplication of treatment samples.

On each sampling date, 20 grams of soil from each treatment replicate was randomly collected using a shovel and carefully placed individually in a labelled plastic bag and into a cooler. In addition, 5 leaf samples were randomly selected from the 3rd-5th node below the terminal of each treated cotton plant and carefully placed individually in a labelled plastic bag and into a separate cooler containing ice blocks. The cooler containing the soil and leaf samples were brought to the laboratory at ACRI and placed in a refrigerator set at 4° C. and then sent to Becker Underwood Pty Ltd in Somersby near Sydney for laboratory analysis.

Soil Analysis

Eleven grams of soil from each sample was weighed and added to a sterile flask containing 99 mL deionised water and surfactant (dilution 10:1). The flask was shaken for 15 minutes on a wrist shaker to achieve a homogeneous solution. This solution was then further diluted to 10$^{-2}$ and 10$^{-3}$. Dilutions were shaken by hand and 100 μL aliquots were aseptically added to and spread over *Metarhizium*-selective media plates for each dilution 10$^{-1}$, 10$^{-2}$ and 10$^{-3}$. Inoculated plates were then incubated at 26° C. for a period of 14 days. Sporulating DAT 511 *Metarhizium* colonies were then differentiated with the aid of microscopy and enumerated with CFU (Colony Forming Unit) counts per gram of soil calculated.

Leaf Analysis

Leaf samples were labelled identically to soil. Samples contained a number of treated leaves. A circular leaf section of diameter 7.5 cm (area 44.2 cm$^2$) was removed from a leaf from each sample and added to a sterile flask containing 99 mL deionised water and surfactant (dilution 10$^0$). The flask was shaken for 15 minutes on a wrist shaker to achieve a homogeneous solution. One mL of solution was then further diluted in 9 mL of deionised water and surfactant (dilution 10$^{-1}$). A sample of the 10$^0$ dilution was then viewed using microscopy and an improved Fuchs-Rosenthal Haemocytometer. The conidia were enumerated from random grids of known volume and enumerated as average leaf haemocytometer conidia per cm$^3$ leaf.

Results

The results from soil and leaves show a defined relationship between detected microbial residues and treatment application rate. Residues were not detected in the unsprayed treatments therefore detected residues from leaves and soil was resultant from the applied biopesticide (DAT 511).

Soil Sample Analysis

The data in FIG. 53 shows that soil microbial residues are very minor at treatment rates of 250 mL/ha and 500 mL/ha. Except for two plots at the Goondiwindi site, residues are also very minor for the 1.0 L/ha rate.

Leaf Sample Analysis

The data in FIG. 54 shows that conidia levels from leaves decreased dramatically between 3 days after treatment (DAT) and 14 DAT and nil CFUs were recovered from plating out. This demonstrates that viable conidia do not persist on treated leaves at detectable levels three days after treatment. UV light is a likely factor.

Example 16

Geographical Distribution of DAT 511 and BC 667 Fungal Isolates in Cotton Growing Areas)

Most biological control agents (BCAs) such as entomopathogenic fungi are persistent. Therefore registration agents or risk assessors of these BCAs generally require information about the natural background levels of the indigenous species (preferably the same species and the same strain) that are to be commercialised. In general, background levels of indigenous BCAs may follow the population dynamics of the insect host population. The increase in the host population is usually followed closely by an increase in levels of the pathogen. Fluctuation in the background levels also depend on a range of other factors including climate, season, soil type, biotype (such as forest or arable field), crop type and agronomic practices.

It was therefore the purpose of this study to provide information about the natural background levels of indigenous fungal isolates in different cotton growing regions in Australia.

Method
Soil Sample Collection

Samples were taken from Brookstead, Goondiwindi (Queensland), Moree and Narrabri (NSW) representing some of the major cotton growing regions in Australia. In each study site, 20 g of soil was taken from two different land uses (viz, arable and pasture). The samples were randomly collected using a shovel and carefully placed individually in a labelled plastic bag and into a cooler. The cooler containing the soil samples were brought to the laboratory and placed in a refrigerator set at 4° C. The samples were then sent to Becker Underwood Pty Ltd laboratory in Somersby for soil analysis and identification of pathogens present in the soils.

Soil Analysis

Eleven grams of soil from each sample was weighed and added to a sterile flask containing 99 mL deionised water and surfactant (dilution 10$^{-1}$). Dilutions were shaken by hand and 100 μL aliquots were aseptically added to and spread over *Metarhizium* and *Beauveria* selective media plates for each dilution $10^{-1}$, $10^{-2}$ and $10^{-3}$. Inoculated plates were then incubated at 26° C. for a period of 14 days. Sporulating DAT 511 *Metarhizium* spp. colonies were then differentiated with the aid of microscopy and enumerated with CFU (Colony Forming Unit) counts per gram of soil calculated. *Metarhizium* spp. and *Beauveria* spp. were also differentiated and enumerated through microscopy with CFU counts per gram of soil calculated.

Results

Soil Analysis

Across all sample sites there were no DAT 511 and BC 667 CFUs detected (FIG. 53). The level of CFUs of *Metarhizium* spp. and *Beauveria* spp. detected were minor and varied with no distinct pattern discernible. For *Metarhizium* spp. the highest detected CFU level measured was 1800 CFU/g soil at the Goondiwindi pasture site. For *Beauveria* spp. the highest detected CFU level measured was 1800 CFU/g soil at the Brookstead, Moree and Goondiwindi pasture sites.

Example 17

Effect of Rainfall on the Persistence of DAT 511 Spores on Cotton Leaves after Application Persistence of DAT 511 spores on the foliage of treated cotton plants after application could ensure that pests not treated with the initial application, especially green mirid 1st-2nd instar nymphs hatching from eggs that were embedded in stems and leaves, come into contact with inoculum from sporulating cadavers. This will cause secondary infection and provide control of the pests. However, rain can wash away DAT 511 spores from treated cotton plants. Therefore, determination of the persistence of DAT 511 spores on treated cotton plant leaves and stems after rainfall events is important in identifying the quantity of spores remaining on treated plants after rain.

It was the purpose of this study to determine the effect of a range of rainfall patterns on the quantity of DAT 511 spores remaining on leaves of treated cotton plants after application.

Method

This study was conducted in a commercial cotton crop at Auscott-Togo, Narrabri. Potted cotton plants at peak squaring stages were used for the study.

Treatment

The treatments evaluated were plants treated with:
1. 250 mL/ha DAT 511 spore in oil ($1\times10^7$ spores/ml);
2. 500 mL/ha DAT 511 spore in oil ($1\times10^7$ spores/ml);
3. 1 L/ha DAT 511 spore in oil ($1\times10^7$ spores/ml); and
4. Unsprayed (control).

In each treatment, 10 potted cotton plants were sprayed and left to dry for one hour under field conditions. When dry, the treated cotton plants were placed on the hills of furrows of commercial Bollgard II cotton crops irrigated with an Overhead Linear Move Irrigator system. The treatments were replicated four times in a randomized complete block design. The unsprayed plants were not subjected to overhead irrigation.

The overhead spray system used in Auscott delivers on average an equivalent of 20 mm/day/ha in one pass. Therefore, to achieve 40 and 60 mm rainfall on the treated plants, the potted plants received 2 and 3 passes of the overhead irrigation (spray) systems. Thus plants in each treatment were subjected to the following irrigation (rainfall) regimes 0 (unsprayed), 20 mm (1 pass of the overhead spray system), 40 mm (2 passes) and 60 mm (3 passes).

Sampling

After each pass of the overhead spray system, five leaves were randomly selected from each treatment and control from the $3^{rd}$-$5^{th}$ node below the terminal of each treated plant, dried for 30 minutes before being carefully placed individually in a labelled plastic bag and into a separate cooler containing ice blocks. The coolers containing the leaf samples were brought to the laboratory and placed in a refrigerator set at 4° C.

Leaf Analysis

Leaf samples were labelled based on DAT 511 treatment rates and the quantity of rainfall received. A circular leaf section of diameter 7.5 cm (area 44.2 cm$^2$) was removed from a leaf from each sample and added to a sterile flask containing 99 mL deionised water and surfactant (dilution $10^0$). The flask was shaken for 15 minutes on a wrist shaker to achieve a homogeneous solution. One mL of solution was then further diluted in 9 mL of deionised water and surfactant (dilution $10^{-1}$). A sample of the $10^0$ dilution was then viewed using microscopy and an improved Fuchs-Rosenthal Haemocytometer. The conidia were enumerated from random grids of known volume and enumerated as average leaf haemocytometer conidia per cm$^3$.

Results

The exposure of DAT 511 spores on treated potted cotton plants to increasing rainfall resulted in a rapid decline of spores on the leaves of the cotton plants (FIG. 54). The quantity of spores (CFU/leaf) on leaves of unsprayed plants and plants treated with 250 mL/ha, 500 mL/ha and 1.0 L/ha DAT 511 before overhead irrigation was 0, 346.7, 500, and 580 CFU/leaf (FIG. 54). When plants treated with 250 mL/ha DAT 511 were subjected to 20, 40 and 60 mm of rain it resulted in 49.0%, 68.0% and 98.9% reduction of leaf spores. Similar trends was obtained when plants were treated with 500 mL/ha and 1.0 L/ha DAT 511. In general, 20 mm of rain washed off about 50% of spores on the treated cotton plants. Forty mm rain washed 50-68% of spores off leaves which will require farmers to repeat the spray application. The quantity of spores (CFU/leaf) on treated plants after 60 mm of rainfall were 4, 11.3 and 17.3 for application rates of 250 mL/ha, 500 mL/ha and 1.0 L/ha respectively (FIG. 54).

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Functionally-equivalent products, compositions and methods are clearly within the scope of the disclosure, as described herein.

The invention claimed is:

1. A composition comprising:
   (i) an isolated or purified strain of *Metarhizium* spp., which has been deposited with the National Measurement Institute under accession number V15/001452, or an isolated or purified spore thereof; and
   (ii) an oil.

2. The composition according to claim 1, wherein the composition comprises:
   (i) the strain of *Metarhizium* spp. or the spore thereof in oil;
   (ii) spores of the strain of *Metarhizium* spp. in the form of a dry powder suspended in the oil; or
   (iii) spores of the strain of *Metarhizium* spp. suspended in an oil-in-water emulsion.

3. A seed or plant propagation material treated with the composition according to claim 1.

4. The seed or plant propagation material according to claim 3, wherein the seed or propagation material is from:
   (i) a plant selected from the group consisting of a cotton plant, a grain crop plant, a cereal crop plant, an oil-seed plant, a fruit-bearing plant, a vegetable-bearing plant, a nut-bearing plant, a flowering plant, a turf plant, a pasture plant, a vine plant, and a legume-bearing plant;
   (ii) a cereal crop plant selected from wheat, maize, corn, rice, oats, rye, barley, millet and sorghum;
   (iii) a cotton plant;
   (iv) a transgenic plant;
   (v) a transgenic cotton plant; or
   (vi) a transgenic Bt cotton.

5. A composition comprising:
   (a) an isolated or purified strain of *Metarhizium* spp., which has been deposited with the National Measurement Institute under accession number V15/001452 suspended in an oil-in-water emulsion; or
   (b) an isolated or purified spore suspended in an oil-in-water emulsion, wherein the spore is a spore of a strain of *Metarhizium* spp., which has been deposited with the National Measurement Institute under accession number V15/001452.

6. A method of controlling one or more invertebrate pests, said method comprising contacting the invertebrate pest with the composition according to claim 1.

7. A method of protecting a plant, plant propagation material and/or animal from one or more invertebrate pests, said method comprising contacting the plant, plant propagation material, soil or other growth medium surrounding roots of the plant, the animal and/or the habitat or breeding ground of the invertebrate pest, with the composition according to claim 1.

8. The method according to claim 7, wherein the strain of *Metarhizium* spp. is provided in the form of reproductively viable spores.

9. The method according to claim 7, wherein the invertebrate pest is a plant pest.

10. The method according to claim 9, wherein the plant pest:
    (i) is an insect or an arachnid;
    (ii) belongs to an order selected from Lepidoptera, Coleoptera, Hemiptera, Thysanoptera and Acarina;
    (iii) is soft-bodied; or
    (iv) is selected from *Helicoveipa* spp., mirids, wireworm, cutworms, apple dimpling bugs, aphids, green vegetable bug, boll weevil, Rutherglen bug, nematodes, thrips, mites, silverleaf whitefly, bollworm, lesser army worm, light brown apple moths, cluster caterpillars, cotton loopers, cotton tipworm, cotton leaf perforators, broken backed bugs, shield bugs, cotton seed bugs, flea beetles, stink bugs, jassids, mealybugs, locust, fruit fly and pale cotton stainer.

11. The method according to claim 9, wherein:
    (i) the plant is a cotton plant;
    (ii) the plant is a transgenic plant;
    (iii) the plant is a transgenic cotton plant; or
    (iv) the plant is a transgenic Bt cotton.

12. The method according to claim 7, wherein the invertebrate pest is an animal pest.

13. The method of claim 12, wherein the animal pest is selected from ticks, lice, flies and fleas.

14. The method according to claim 7, wherein the composition is applied to a plant or its surrounding, a plant propagation material, an animal and/or a breeding ground or habitat of the invertebrate pest in conjunction with an additional substance having insecticidal or pesticidal activity.

15. A method of improving crop yield for a plant variety, said method comprising treating at least (i) one plant and/or its surrounding, (ii) a propagation material from which the plant is to grow, or (iii) a breeding ground or habitat of a pest of the plant with the composition according to claim 1.

* * * * *

SEQUENCE LISTING

<160> NUMBER OF SEQ ID NOS: 1

<210> SEQ ID NO 1
<211> LENGTH: 529
<212> TYPE: DNA
<213> ORGANISM: Metarhizium anisopliae

<400> SEQUENCE: 1

```
cgattggccg cggttcactc cacccctgtg attataccte taattgttgc ttcggcggga        60
cttcgcgccc gccggggacc caaaccttct gaatttttta ataagtatct tctgagtggt       120
taaaaaaatg aatcaaaact ttcaacaacg gatctcttgg ttctggcatc gatgaagaac       180
gcagcgaaat gcgataagta atgtgaattg cagaattcag tgaatcatcg aatctttgaa       240
cgcacattgc gcccgtcagt attctggcgg gcatgcctgt tcgagcgtca ttacgcccct       300
caagtcccct gtggacttgg tgttggggat cggcgaggct ggttttccag cacagccgtc       360
ccttaaatta attggcggtc tcgccgtggc cctcctctgc gcagtagtaa aacactcgca       420
acaggagccc ggcgcggtcc actgccgtaa aaccccccaa cttttatag ttgacctcga       480 atcaggtagg actaccgct gaacttaagc atatcaataa gcggaggaa                    529
```